(12) United States Patent (10) Patent No.: US 8,354,423 B2
Cassayre et al. (45) Date of Patent: Jan. 15, 2013

(54) INSECTICIDAL SPIRONINDANE DERIVATIVES

(75) Inventors: Jérôme Cassayre, Basel (CH); Louis-Pierre Molleyres, Basel (CH); Peter Maienfisch, Basel (CH); Fredrik Cederbaum, Basel (CH)

(73) Assignee: Syngenta Crop Protection LLC, Greensboro, NC (US)

( * ) Notice: Subject to any disclaimer, the term of this patent is extended or adjusted under 35 U.S.C. 154(b) by 987 days.

(21) Appl. No.: 10/581,177

(22) PCT Filed: Dec. 9, 2004

(86) PCT No.: PCT/IB2004/004108
§ 371 (c)(1),
(2), (4) Date: Aug. 28, 2008

(87) PCT Pub. No.: WO2005/058836
PCT Pub. Date: Jun. 30, 2005

(65) Prior Publication Data
US 2008/0306101 A1    Dec. 11, 2008

(30) Foreign Application Priority Data
Dec. 12, 2003 (GB) .................................. 0328906.3

(51) Int. Cl.
*C07D 401/04* (2006.01)
*A61K 31/438* (2006.01)
(52) U.S. Cl. ............... 514/278; 546/16; 546/17; 546/18
(58) Field of Classification Search .................... 546/16, 546/17, 18; 514/278
See application file for complete search history.

(56) References Cited

U.S. PATENT DOCUMENTS

| | | | |
|---|---|---|---|
| 5,434,158 A | 7/1995 | Shah | |
| 5,536,716 A | 7/1996 | Chen et al. | |
| 5,962,462 A | 10/1999 | Mills et al. | |

FOREIGN PATENT DOCUMENTS

| | | |
|---|---|---|
| CH | 565 153 A5 | 8/1975 |
| GB | 1421208 | 1/1976 |
| GB | 1423851 | 2/1976 |
| WO | 9417045 A | 8/1994 |
| WO | 9808835 A | 3/1998 |
| WO | 9825604 A | 6/1998 |
| WO | 9909984 A | 3/1999 |
| WO | 9914193 A | 3/1999 |
| WO | 9964002 A | 12/1999 |
| WO | 01/60796 A1 | 8/2001 |
| WO | 02/085354 A1 | 10/2002 |

OTHER PUBLICATIONS

Dorwald F. A. Side Reactions in Organic Synthesis, 2005, Wiley: VCH, Weinheim p. IX of Preface.*
English translation of Japanese Office Action (Appln. No. 2006-543659, filed Dec. 9, 2004) pp. 1-5.

* cited by examiner

*Primary Examiner* — Rita Desai
(74) *Attorney, Agent, or Firm* — R. Kody Jones

(57) ABSTRACT

An insecticidal compound of formula I wherein X is O or $NR^{11}$ where $R^{11}$ is hydrogen, optionally substituted alkyl, optionally substituted aryl or optionally substituted heteroaryl; Y is a single bond, C=O, C=S or $S(O)_m$ where m is 0, 1 or 2; $R^1$, $R^2$, $R^3$, $R^4$, $R^8$ and Ra are specified organic groups and p is 0, 1, 2, 3, 4, 5 or 6; q is 0, 1, 2, 3, 4, 5 or 6 provided that p+q is 1, 2, 3, 4, 5 or 6; or salts or N-oxides thereof; compositions containing them and their using in controlling insects, acarines, nematodes or molluscs.

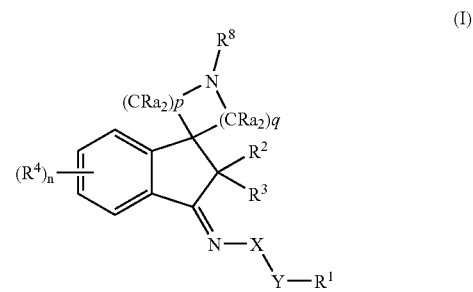

17 Claims, No Drawings

INSECTICIDAL SPIROINDANE DERIVATIVES

The present invention relates to spiroindane derivatives, to processes for preparing them, to insecticidal, acaricidal, molluscicidal and nematicidal compositions comprising them and to methods of using them to combat and control insect, acarine, mollusc and nematode pests.

Spiroindanes with pharmaceutical properties are disclosed in for example WO9808835, WO 9825604, WO 9417045, U.S. Pat. No. 5,434,158, GB1421208 and GB1423851. It has now surprisingly been found that certain spiroindanes have insecticidal properties.

The present invention therefore provides a compound of formula (I):

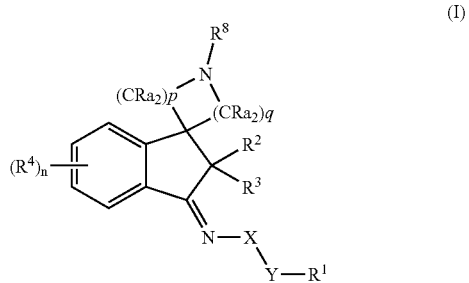

wherein X is O or $NR^{11}$ where $R^{11}$ is hydrogen, optionally substituted alkyl, optionally substituted aryl or optionally substituted heteroaryl;

Y is a single bond, C=O, C=S or $S(O)_m$ where m is 0, 1 or 2;

$R^1$ is hydrogen, optionally substituted alkyl, optionally substituted alkoxycarbonyl, optionally substituted alkylcarbonyl, aminocarbonyl, optionally substituted alkylaminocarbonyl, optionally substituted dialkylaminocarbonyl, optionally substituted aryl, optionally substituted heteroaryl, optionally substituted alkoxy, optionally substituted aryloxy, optionally substituted heteroaryloxy, optionally substituted heterocyclyloxy, cyano, optionally substituted alkenyl, optionally substituted alkynyl, optionally substituted cycloalkyl, optionally substituted cycloalkenyl, formyl, optionally substituted heterocyclyl, optionally substituted alkylthio, NO or $NR^{13}R^{14}$ where $R^{13}$ and $R^{14}$ are independently hydrogen, $COR^{15}$, optionally substituted alkyl, optionally substituted aryl, optionally substituted heteroaryl, optionally substituted heterocyclyl or $R^{13}$ and $R^{14}$ together with the N atom to which they are attached form a group —N=C($R^{16}$)—$N^{17}R^{18}$; $R^{15}$ is H, optionally substituted alkyl, optionally substituted alkoxy, optionally substituted aryl, optionally substituted aryloxy optionally substituted heteroaryl, optionally substituted heteroaryloxy or $NR^{19}R^{20}$; $R^{16}$, $R^{17}$ and $R^{18}$ are each independently H or lower alkyl; $R^{19}$ and $R^{20}$ are independently optionally substituted alkyl, optionally substituted aryl or optionally substituted heteroaryl;

$R^2$ and $R^3$ are independently hydrogen, halogen, cyano, optionally substituted alkyl, optionally substituted alkoxy or optionally substituted aryl;

each $R^4$ is independently halogen, nitro, cyano, optionally substituted $C_{1-8}$ alkyl, optionally substituted $C_{2-6}$ alkenyl, optionally substituted $C_{2-6}$ alkynyl, optionally substituted alkoxycarbonyl, optionally substituted alkylcarbonyl, optionally substituted alkylaminocarbonyl, optionally substituted dialkylaminocarbonyl, optionally substituted $C_{3-7}$ cycloalkyl, optionally substituted aryl, optionally substituted heteroaryl, optionally substituted heterocyclyl, optionally substituted alkoxy, optionally substituted aryloxy, optionally substituted heteroaryloxy, optionally substituted alkylthio or $R^{21}R^{22}N$ where $R^{21}$ and $R^{22}$ are, independently, hydrogen, $C_{1-8}$ alkyl, $C_{3-7}$ cycloalkyl, $C_{3-6}$ alkenyl, $C_{3-6}$ alkynyl, $C_{3-7}$ cycloalkyl($C_{1-4}$)alkyl, $C_{2-6}$ haloalkyl, $C_{1-6}$ alkoxy($C_{1-6}$)alkyl, $C_{1-6}$ alkoxycarbonyl or $R^{21}$ and $R^{22}$ together with the N atom to which they are attached form a five, six or seven-membered heterocyclic ring which may contain one or two further heteroatoms selected from O, N or S and which may be optionally substituted by one or two $C_{1-6}$ alkyl groups, or 2 adjacent groups $R^4$ together with the carbon atoms to which they are attached form a 4, 5, 6, or 7 membered carbocyclic or heterocyclic ring which may be optionally substituted by halogen; n is 0, 1, 2, 3 or 4;

each Ra is independently hydrogen, halogen, hydroxy, cyano, optionally substituted $C_{1-8}$ alkyl, optionally substituted $C_{2-6}$ alkenyl, optionally substituted $C_{2-6}$ alkynyl, optionally substituted alkoxycarbonyl, optionally substituted alkylcarbonyl, optionally substituted alkylaminocarbonyl, optionally substituted dialkylaminocarbonyl, optionally substituted $C_{3-7}$ cycloalkyl, optionally substituted aryl, optionally substituted heteroaryl, optionally substituted heterocyclyl, optionally substituted alkoxy, optionally substituted aryloxy, optionally substituted heteroaryloxy, optionally substituted alkylthio, optionally substituted arylthio or $R^{23}R^{24}N$ where $R^{23}$ and $R^{24}$ are, independently, hydrogen, $C_{1-8}$ alkyl, $C_{3-7}$ cycloalkyl, $C_{3-6}$ alkenyl, $C_{3-6}$ alkynyl, $C_{3-7}$ cycloalkyl($C_{1-4}$)alkyl, $C_{2-6}$ haloalkyl, $C_{1-6}$ alkoxy($C_{1-6}$)alkyl, $C_{1-6}$ alkoxycarbonyl or $R^{23}$ and $R^{24}$ together with the N atom to which they are attached form a five, six or seven-membered heterocyclic ring which may contain one or two further heteroatoms selected from O, N or S and which may be optionally substituted by one or two $C_{1-6}$ alkyl groups, or two Ra groups attached to the same carbon atom are =O or two Ra groups attached to adjacent carbon atoms form a bond, or two Ra groups together with the carbon atom to which they are attached form a three- to seven-membered ring, that may be saturated or unsaturated, and that may contain one or two hetero atoms selected from the group consisting of N, O and S, and which may be optionally substituted by one or two $C_{1-6}$ alkyl groups; or two Ra groups together form a group —$CH_2$—, —CH=CH— or —$CH_2CH_2$; p is 0, 1, 2, 3, 4, 5 or 6; q is 0, 1, 2, 3, 4, 5 or 6 provided that p+q is 1, 2, 3, 4, 5 or 6;

$R^8$ is optionally substituted alkyl, optionally substituted alkenyl, optionally substituted alkynyl, optionally substituted cycloalkyl, optionally substituted aryl, optionally substituted alkoxy, optionally substituted aryloxy, optionally substituted alkoxycarbonyl, optionally substituted alkylcarbonyl or optionally substituted alkenylcarbonyl; or salts or N-oxides thereof.

The compounds of formula (I) may exist in different geometric or optical isomers or tautomeric forms. This invention covers all such isomers and tautomers and mixtures thereof in all proportions as well as isotopic forms such as deuterated compounds.

Each alkyl moiety either alone or as part of a larger group (such as alkoxy, alkoxycarbonyl, alkylcarbonyl, alkylaminocarbonyl, dialkylaminocarbonyl) is a straight or branched chain and is, for example, methyl, ethyl, n-propyl, n-butyl, n-pentyl, n-hexyl, iso-propyl, n-butyl, sec-butyl, iso-butyl, tert-butyl or neo-pentyl. The alkyl groups are suitably $C_1$ to $C_{12}$ alkyl groups, but are preferably $C_1$-$C_{10}$, more preferably $C_1$-$C_8$, even more preferably preferably $C_1$-$C_6$ and most preferably $C_1$-$C_4$ alkyl groups.

When present, the optional substituents on an alkyl moiety (alone or as part of a larger group such as alkoxy, alkoxycarbonyl, alkylcarbonyl, alkylaminocarbonyl, dialkylaminocarbonyl) include one or more of halogen, nitro, cyano, NCS—, $C_{3-7}$ cycloalkyl (itself optionally substituted with $C_{1-6}$ alkyl or halogen), $C_{5-7}$ cycloalkenyl (itself optionally substituted with $C_{1-6}$ alkyl or halogen), hydroxy, $C_{1-10}$ alkoxy, $C_{1-10}$ alkoxy($C_{1-10}$)alkoxy, tri($C_{1-4}$)alkylsilyl($C_{1-6}$)alkoxy, $C_{1-6}$ alkoxycarbonyl($C_{1-10}$)alkoxy, $C_{1-10}$ haloalkoxy, aryl($C_{1-4}$)-alkoxy (where the aryl group is optionally substituted), $C_{3-7}$ cycloalkyloxy (where the cycloalkyl group is optionally substituted with $C_{1-6}$ alkyl or halogen), $C_{2-10}$ alkenyloxy, $C_{2-10}$ alkynyloxy, SH, $C_{1-10}$ alkylthio, $C_{1-10}$ haloalkylthio, aryl($C_{1-4}$)alkylthio (where the aryl group is optionally substituted), $C_{3-7}$ cycloalkylthio (where the cycloalkyl group is optionally substituted with $C_{1-6}$ alkyl or halogen), tri($C_{1-4}$)alkylsilyl($C_{1-6}$)alkylthio, arylthio (where the aryl group is optionally substituted), $C_{1-6}$ alkylsulfonyl, $C_{1-6}$ haloalkylsulfonyl, $C_{1-6}$ alkylsulfinyl, $C_{1-6}$ haloalkylsulfinyl, arylsulfonyl (where the aryl group may be optionally substituted), tri($C_{1-4}$)alkylsilyl, aryldi($C_{1-4}$)alkylsilyl, ($C_{1-4}$)alkyldiarylsilyl, triarylsilyl, $C_{1-10}$ alkylcarbonyl, $HO_2C$, $C_{1-10}$ alkoxycarbonyl, aminocarbonyl, $C_{1-6}$ alkylaminocarbonyl, di($C_{1-6}$ alkyl)aminocarbonyl, N—($C_{1-3}$ alkyl)-N—($C_{1-3}$ alkoxy)aminocarbonyl, $C_{1-6}$ alkylcarbonyloxy, arylcarbonyloxy (where the aryl group is optionally substituted), di($C_{1-6}$)alkylaminocarbonyloxy, oximes such as =NOalkyl, =NOhaloalkyl and =NOaryl (itself optionally substituted), aryl (itself optionally substituted), heteroaryl (itself optionally substituted), heterocyclyl (itself optionally substituted with $C_{1-6}$ alkyl or halogen), aryloxy (where the aryl group is optionally substituted), heteroaryloxy, (where the heteroaryl group is optionally substituted), heterocyclyloxy (where the heterocyclyl group is optionally substituted with $C_{1-6}$ alkyl or halogen), amino, $C_{1-6}$ alkylamino, di($C_{1-6}$)alkylamino, $C_{1-6}$ alkylcarbonylamino, N—($C_{1-6}$)alkylcarbonyl-N—($C_{1-6}$)alkylamino, $C_{2-6}$ alkenylcarbonyl, $C_{2-6}$ alkynylcarbonyl, $C_{3-6}$ alkenyloxycarbonyl, $C_{3-6}$ alkynyloxycarbonyl, aryloxycarbonyl (where the aryl group is optionally substituted) and arylcarbonyl (where the aryl group is optionally substituted).

Alkenyl and alkynyl moieties can be in the form of straight or branched chains, and the alkenyl moieties, where appropriate, can be of either the (E)- or (Z)-configuration. Examples are vinyl, allyl and propargyl.

When present, the optional substituents on alkenyl or alkynyl include those optional substituents given above for an alkyl moiety.

In the context of this specification acyl is optionally substituted $C_{1-6}$ alkylcarbonyl (for example acetyl), optionally substituted $C_{2-6}$ alkenylcarbonyl, optionally substituted $C_{2-6}$ alkynylcarbonyl, optionally substituted arylcarbonyl (for example benzoyl) or optionally substituted heteroarylcarbonyl.

Halogen is fluorine, chlorine, bromine or iodine.

Haloalkyl groups are alkyl groups which are substituted with one or more of the same or different halogen atoms and are, for example, $CF_3$, $CF_2Cl$, $CF_3CH_2$ or $CHF_2CH_2$.

In the context of the present specification the terms "aryl" and "aromatic ring system" refer to ring systems which may be mono-, bi- or tricyclic. Examples of such rings include phenyl, naphthalenyl, anthracenyl, indenyl or phenanthrenyl. A preferred aryl group is phenyl. In addition, the terms "heteroaryl", "heteroaromatic ring" or "heteroaromatic ring system" refer to an aromatic ring system containing at least one heteroatom and consisting either of a single ring or of two or more fused rings. Preferably, single rings will contain up to three and bicyclic systems up to four heteroatoms which will preferably be chosen from nitrogen, oxygen and sulphur. Examples of such groups include furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole quinolinyl, isoquinolinyl, cinnolinyl, phthalazinyl, quinazolinyl, quinoxalinyl, naphthyridinyl, benzotriazinyl, purinyl, pteridinyl and indolizinyl. Preferred examples of heteroaromatic radicals include pyridyl, pyrimidyl, triazinyl, thienyl, furyl, oxazolyl, isoxazolyl, 2,1,3-benzoxadiazole and thiazolyl.

The terms heterocycle and heterocyclyl refer to a non-aromatic ring containing up to 10 atoms including one or more (preferably one or two) heteroatoms selected from O, S and N. Examples of such rings include 1,3-dioxolane, tetrahydrofuran and morpholine.

When present, the optional substituents on heterocyclyl include $C_{1-6}$ alkyl and $C_{1-6}$ haloalkyl as well as those optional substituents given above for an alkyl moiety.

Cycloalkyl includes cyclopropyl, cyclopentyl and cyclohexyl.

Cycloalkenyl includes cyclopentenyl and cyclohexenyl.

When present, the optional substituents on cycloalkyl or cycloalkenyl include $C_{1-3}$ alkyl as well as those optional substituents given above for an alkyl moiety.

Carbocyclic rings include aryl, cycloalkyl and cycloalkenyl groups.

When present, the optional substituents on aryl or heteroaryl are selected independently, from halogen, nitro, cyano, NCS—, $C_{1-6}$ alkyl, $C_{1-6}$ haloalkyl, $C_{1-6}$ alkoxy-($C_{1-6}$) alkyl, $C_{2-6}$ alkenyl, $C_{2-6}$ haloalkenyl, $C_{2-6}$ alkynyl, $C_{3-7}$ cycloalkyl (itself optionally substituted with $C_{1-6}$ alkyl or halogen), $C_{5-7}$ cycloalkenyl (itself optionally substituted with $C_{1-6}$ alkyl or halogen), hydroxy, $C_{1-10}$ alkoxy, $C_{1-10}$ alkoxy($C_{1-10}$)alkoxy, tri($C_{1-4}$)alkyl-silyl($C_{1-6}$)alkoxy, $C_{1-6}$ alkoxycarbonyl($C_{1-10}$)alkoxy, $C_{1-10}$ haloalkoxy, aryl($C_{1-4}$)alkoxy (where the aryl group is optionally substituted with halogen or $C_{1-6}$ alkyl), $C_{3-7}$ cycloalkyloxy (where the cycloalkyl group is optionally substituted with $C_{1-6}$ alkyl or halogen), $C_{2-10}$ alkenyloxy, $C_{2-10}$ alkynyloxy, SH, $C_{1-10}$ alkylthio, $C_{1-10}$ haloalkylthio, aryl($C_{1-4}$)alkylthio $C_{3-7}$ cycloalkylthio (where the cycloalkyl group is optionally substituted with $C_{1-6}$ alkyl or halogen), tri($C_{1-4}$)-alkylsilyl($C_{1-6}$)alkylthio, arylthio, $C_{1-6}$ alkylsulfonyl, $C_{1-6}$ haloalkylsulfonyl, $C_{1-6}$ alkylsulfinyl, $C_{1-6}$ haloalkylsulfinyl, arylsulfonyl, tri($C_{1-4}$)alkylsilyl, aryldi($C_{1-4}$)-alkylsilyl, ($C_{1-4}$)alkyldiarylsilyl, triarylsilyl, $C_{1-10}$ alkylcarbonyl, $HO_2C$, $C_{1-10}$ alkoxycarbonyl, aminocarbonyl, $C_{1-6}$ alkylaminocarbonyl, di($C_{1-6}$ alkyl)-aminocarbonyl, N—($C_{1-3}$ alkyl)-N—($C_{1-3}$ alkoxy)aminocarbonyl, $C_{1-6}$ alkylcarbonyloxy, arylcarbonyloxy, di($C_{1-6}$)alkylamino-carbonyloxy, aryl (itself optionally substituted with $C_{1-6}$ alkyl or halogen), heteroaryl (itself optionally substituted with $C_{1-6}$ alkyl or halogen), heterocyclyl (itself optionally substituted with $C_{1-6}$ alkyl or halogen), aryloxy (where the aryl group is optionally substituted with $C_{1-6}$ alkyl or halogen), heteroaryloxy (where the heteroaryl group is optionally substituted with $C_{1-6}$ alkyl or halogen), heterocyclyloxy (where the heterocyclyl group is optionally substituted with $C_{1-6}$ alkyl or halogen), amino, $C_{1-6}$ alkylamino, di($C_{1-6}$)alkylamino, $C_{1-6}$ alkylcarbonylamino, N—($C_{1-6}$)alkylcarbonyl-N—($C_{1-6}$)alkylamino, arylcarbonyl, (where the aryl group is itself optionally substituted with halogen or $C_{1-6}$ alkyl) or two adjacent positions on an aryl or heteroaryl system may be cyclised to form a 5, 6 or 7 membered carbocyclic or heterocyclic ring, itself optionally substituted with halogen or $C_{1-6}$ alkyl. Further substituents for aryl or heteroaryl include aryl carbonyl amino (where the aryl group is substituted by $C_{1-6}$ alkyl or halogen), ($C_{1-6}$)alkyloxycarbonylamino ($C_{1-6}$)alkyloxycarbonyl-N—($C_{1-6}$)alkylamino, aryloxycarbonylamino (where the aryl group is substituted by $C_{1-6}$ alkyl or halogen), aryloxycarbonyl-N—($C_{1-6}$)alkylamino, (where the aryl group is substituted by $C_{1-6}$ alkyl or halogen), arylsulphonylamino (where the aryl group is substituted by $C_{1-6}$ alkyl or halogen), arylsulphonyl-N—($C_{1-6}$)alkylamino (where the aryl group is substituted by $C_{1-6}$ alkyl or halogen), aryl-N—($C_{1-6}$)alkylamino (where the aryl group is substituted by $C_{1-6}$ alkyl or halogen), arylamino (where the aryl group is substituted by $C_{1-6}$ alkyl or halogen), heteroaryl amino (where the heteroaryl group is substituted by $C_{1-6}$ alkyl or halogen), heterocyclylamino (where the heterocyclyl group is substituted by $C_{1-6}$ alkyl or halogen), aminocarbonylamino, $C_{1-6}$ alkylaminocarbonyl amino, di($C_{1-6}$)alkylaminocarbonyl amino, arylaminocarbonyl amino where the aryl group is substituted by $C_{1-6}$ alkyl or halogen), aryl-N—($C_{1-6}$)alkylaminocarbonylamino where the aryl group is substituted by $C_{1-6}$ alkyl or halogen), $C_{1-6}$ alkylaminocarbonyl-N—($C_{1-6}$)alkyl amino, di($C_{1-6}$)alkylaminocarbonyl-N—($C_{1-6}$)alkyl amino, arylaminocarbonyl-N—($C_{1-6}$)alkyl amino where the aryl group is substituted by $C_{1-6}$ alkyl or halogen) and aryl-N—($C_{1-6}$)alkylaminocarbonyl-N—($C_{1-6}$)alkyl amino where the aryl group is substituted by $C_{1-6}$ alkyl or halogen).

For substituted phenyl moieties, heterocyclyl and heteroaryl groups it is preferred that one or more substituents are independently selected from halogen, $C_{1-6}$ alkyl, $C_{1-6}$ haloalkyl, $C_{1-6}$ alkoxy($C_{1-6}$)alkyl, $C_{1-6}$ alkoxy, $C_{1-6}$ haloalkoxy, $C_{1-6}$ alkylthio, $C_{1-6}$ haloalkylthio, $C_{1-6}$ alkylsulfinyl, $C_{1-6}$ haloalkylsulfinyl, $C_{1-6}$ alkylsulfonyl, $C_{1-6}$ haloalkylsulfonyl, $C_{2-6}$ alkenyl, $C_{2-6}$ haloalkenyl, $C_{2-6}$ alkynyl, $C_{3-7}$ cycloalkyl, nitro, cyano, $CO_2H$, $C_{1-6}$ alkylcarbonyl, $C_{1-6}$ alkoxycarbonyl, $R^{25}R^{26}N$ or $R^{27}R^{28}NC(O)$; wherein $R^{25}$, $R^{26}$, $R^{27}$ and $R^{28}$ are, independently, hydrogen or $C_{1-6}$ alkyl. Further preferred substituents are aryl and heteroaryl groups.

Haloalkenyl groups are alkenyl groups which are substituted with one or more of the same or different halogen atoms.

It is to be understood that dialkylamino substituents include those where the dialkyl groups together with the N atom to which they are attached form a five, six or seven-membered heterocyclic ring which may contain one or two further heteroatoms selected from O, N or S and which is optionally substituted by one or two independently selected ($C_{1-6}$)alkyl groups. When heterocyclic rings are formed by joining two groups on an N atom, the resulting rings are suitably pyrrolidine, piperidine, thiomorpholine and morpholine each of which may be substituted by one or two independently selected ($C_{1-6}$) alkyl groups.

Preferably the optional substituents on an alkyl moiety include one or more of halogen, nitro, cyano, $HO_2C$, $C_{1-10}$ alkoxy (itself optionally substituted by $C_{1-10}$ alkoxy), aryl ($C_{1-4}$)alkoxy, $C_{1-10}$ alkylthio, $C_{1-10}$ alkylcarbonyl, $C_{1-10}$ alkoxycarbonyl, $C_{1-6}$ alkylaminocarbonyl, di($C_{1-6}$ alkyl)aminocarbonyl, ($C_{1-6}$)alkylcarbonyloxy, optionally substituted phenyl, heteroaryl, aryloxy, arylcarbonyloxy, heteroaryloxy, heterocyclyl, heterocyclyloxy, $C_{3-7}$ cycloalkyl (itself optionally substituted with ($C_{1-6}$)alkyl or halogen), $C_{3-7}$ cycloalkyloxy, $C_{5-7}$ cycloalkenyl, $C_{1-6}$ alkylsulfonyl, $C_{1-6}$ alkylsulfinyl, tri($C_{1-4}$)alkylsilyl, tri($C_{1-4}$)alkylsilyl($C_{1-6}$)alkoxy, aryldi($C_{1-4}$)alkylsilyl, ($C_{1-4}$)alkyldiarylsilyl and triarylsilyl.

Preferably the optional substituents on alkenyl or alkynyl include one or more of halogen, aryl and $C_{3-7}$ cycloalkyl.

A preferred optional substituent for heterocyclyl is $C_{1-6}$ alkyl.

Preferably the optional substituents for cycloalkyl include halogen, cyano and $C_{1-3}$ alkyl.

Preferably the optional substituents for cycloalkenyl include $C_{1-3}$ alkyl, halogen and cyano.

X is preferably $NR^{11}$.

$R^{11}$ is preferably hydrogen or $C_{1-6}$ alkyl, most preferably hydrogen.

Preferably Y is a single bond, C=O or $S(O)_m$ where m is 0, 1 or 2.

More preferably Y is a single bond, C=O or $SO_2$.

Yet more preferably Y is a single bond or C=O.

Most preferably Y is C=O.

Preferably $R^1$ is hydrogen, $C_{1-6}$ alkyl, $C_{1-6}$ cyanoalkyl, $C_{1-6}$ haloalkyl, $C_{3-7}$ cycloalkyl($C_{1-4}$)alkyl, $C_{1-6}$ alkoxy($C_{1-6}$)alkyl, heteroaryl($C_{1-6}$)alkyl (wherein the heteroaryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the heteroaryl system may be cyclised to form a 5, 6 or 7 membered carbocyclic or heterocyclic ring, itself optionally substituted with halogen), aryl($C_{1-6}$)alkyl (wherein the aryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the aryl system may be cyclised to form a 5, 6 or 7 membered carbocyclic or heterocyclic ring, itself optionally substituted with halogen), $C_{1-6}$ alkylcarbonylamino($C_{1-6}$)alkyl, aryl (which may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the aryl system may be cyclised to form a 5, 6 or 7 membered carbocyclic or heterocyclic ring, itself optionally substituted with halogen), heteroaryl (which may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the heteroaryl system may be cyclised to form a 5, 6 or 7 membered carbocyclic or heterocyclic ring, itself optionally substituted with halogen), $C_{1-6}$ alkoxy, $C_{1-6}$ haloalkoxy, phenoxy (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryloxy (optionally substituted by halo, nitro, cyano, $C_{1-6}$ alkyl, $C_{1-6}$ haloalkyl, $C_{1-6}$ alkoxy or $C_{1-6}$ haloalkoxy), heterocyclyloxy (optionally substituted by halo, $C_{1-6}$ alkyl, $C_{1-6}$ haloalkyl, $C_{1-6}$ alkoxy or $C_{1-6}$ haloalkoxy), cyano, $C_{2-6}$ alkenyl, $C_{2-6}$ alkynyl, $C_{3-6}$ cycloalkyl, $C_{5-7}$ cycloalkenyl, heterocyclyl (optionally substituted by halo, nitro, cyano, $C_{1-6}$ alkyl, $C_{1-6}$ haloalkyl, $C_{1-6}$ alkoxy or $C_{1-6}$ haloalkoxy), $C_{1-6}$ alkylthio, $C_{1-6}$ haloalkylthio or $NR^{13}R^{14}$ where $R^{13}$ and $R^{14}$ are independently hydrogen, $C_{1-6}$ alkyl, $C_{1-6}$ haloalkyl, $C_{1-6}$ alkoxy($C_{1-6}$)alkyl, phenyl (which may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino, dialkylamino or $C_{1-4}$ alkoxycarbonyl), phenyl($C_{1-6}$)alkyl (wherein the phenyl group may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino, dialkylamino, $C_{1-6}$ alkylsulfonyl, $C_{1-6}$ alkoxycarbonyl, or two adjacent positions on the phenyl ring may be cyclised to form a 5, 6 or 7 membered carbocyclic or heterocyclic ring, itself optionally substituted with halogen), heteroaryl ($C_{1-6}$) alkyl (wherein the heteroaryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the heteroaryl system may be cyclised to form a 5, 6 or 7 membered carbocyclic or heterocyclic ring, itself optionally substituted with halogen) or heteroaryl (which may be optionally substituted by halo, nitro, cyano, $C_{1-6}$ alkyl, $C_{1-6}$ haloalkyl, $C_{1-6}$ alkoxy or $C_{1-6}$ haloalkoxy, $C_{1-4}$ alkoxycarbonyl $C_{1-6}$ alkylcarbonylamino, phenyloxycarbonylamino (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), amino, $C_{1-6}$ alkylamino or phenylamino (wherein the phenyl group is optionally substituted halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino)).

More preferably $R^1$ is $C_{1-6}$ alkyl, $C_{1-6}$ haloalkyl, $C_{1-6}$ alkoxy($C_{1-6}$)alkyl, heteroaryl($C_{1-3}$)alkyl (wherein the heteroaryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkoxycarbonyl, or two adjacent positions on the heteroaryl system may be cyclised to form a 5, 6 or 7 membered carbocyclic or heterocyclic ring, itself optionally substituted with halogen), phenyl($C_{1-3}$)alkyl (wherein the phenyl group may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino, dialkylamino, $C_{1-6}$ alkylsulfonyl, $C_{1-6}$ alkoxycarbonyl, or two adjacent positions on the phenyl ring may be cyclised to form a 5, 6 or 7 membered carbocyclic or heterocyclic ring, itself optionally substituted with halogen), phenyl (which may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino, dialkylamino, $C_{1-6}$ alkylsulfonyl, $C_{1-6}$ alkoxycarbonyl, or two adjacent positions on the phenyl ring may be cyclised to form a 5, 6 or 7 membered carbocyclic or heterocyclic ring, itself optionally substituted with halogen), heteroaryl (which may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkoxycarbonyl, or two adjacent positions on the heteroaryl system may be cyclised to form a 5, 6 or 7 membered carbocyclic or heterocyclic ring, itself optionally substituted with halogen), $C_{1-6}$ alkoxy, $C_{1-6}$ haloalkoxy, $C_{2-6}$ alkenyl, heterocyclyl (optionally substituted by halo, cyano, $C_{1-6}$ alkyl, $C_{1-6}$ haloalkyl, $C_{1-6}$ alkoxy or $C_{1-6}$ haloalkoxy), $C_{1-6}$ alkylthio, $C_{1-6}$ haloalkylthio or $NR^{13}R^{14}$ where $R^{13}$ and $R^{14}$ are independently hydrogen, $C_{1-6}$ alkyl or $C_{1-6}$ haloalkyl, $C_{1-6}$ alkoxy($C_{1-6}$)alkyl, $C_{2-6}$ alkylcarbonyl, phenylcarbonyl, (where the phenyl is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), phenyl($C_{1-3}$)alkyl (wherein the phenyl group may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino, dialkylamino, $C_{1-6}$ alkylsulfonyl, $C_{1-6}$ alkoxycarbonyl, or two adjacent positions on the phenyl ring may be cyclised to form a 5, 6 or 7 membered carbocyclic or heterocyclic ring, itself optionally substituted with halogen) or heteroaryl($C_{1-3}$)alkyl (wherein the heteroaryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the heteroaryl system may be cyclised to form a 5, 6 or 7 membered carbocyclic or heterocyclic ring, itself optionally substituted with halogen).

Even more preferably $R^1$ is $C_{1-6}$ alkyl, $C_{1-6}$ haloalkyl, heteroaryl($C_{1-3}$)alkyl (wherein the heteroaryl group may be optionally substituted by halo, cyano, $C_{1-6}$ alkyl, $C_{1-6}$ haloalkyl and where the heteroaryl group is a thiazole, pyridine, pyrimidine, pyrazine or pyridazine ring), heteroaryl (optionally substituted by halo, cyano, $C_{1-6}$ alkyl, $C_{1-6}$ haloalkyl and where the heteroaryl group is a pyridine, pyrimidine, 2,1,3-benzoxadiazole, pyrazine or pyridazine ring), $C_{1-6}$ alkoxy, $C_{1-6}$ alkoxy($C_{1-6}$)alkyl, $C_{1-6}$ alkylamino, $C_{1-6}$ alkoxy($C_{1-6}$)alkylamino or heteroaryl($C_{1-3}$)alkylamino (wherein the heteroaryl group may be optionally substituted by halo, cyano, $C_{1-6}$ alkyl, $C_{1-6}$ haloalkyl and where the heteroaryl group is a thiazole, pyridine, pyrimidine, pyrazine or pyridazine ring).

Most preferably $R^1$ is pyridyl (optionally substituted by halo, $C_{1-3}$ alkyl or $C_{1-3}$ haloalkyl) especially halo-substituted pyridyl.

It is preferred that $R^2$ and $R^3$ are independently hydrogen, $C_{1-6}$ alkyl, $C_{1-6}$ haloalkyl, $C_{1-6}$ alkoxy or cyano.

More preferably $R^2$ and $R^3$ are independently hydrogen, halogen, $C_{1-2}$ alkyl, $C_{1-2}$ haloalkyl, $C_{1-2}$ alkoxy, cyano.

Even more preferably $R^2$ and $R^3$ are independently hydrogen or $C_{1-4}$ alkyl.

Yet more preferably $R^2$ and $R^3$ are independently hydrogen or methyl.

Most preferably $R^2$ and $R^3$ are both hydrogen.

Preferably each $R^4$ is independently halogen, cyano, $C_{1-8}$ alkyl, $C_{1-8}$ haloalkyl, $C_{1-6}$ cyanoalkyl, $C_{1-6}$ alkoxy($C_{1-6}$) alkyl, $C_{3-7}$ cycloalkyl($C_{1-6}$)alkyl, $C_{5-6}$ cycloalkenyl($C_{1-6}$) alkyl, $C_{3-6}$ alkenyloxy($C_{1-6}$)alkyl, $C_{3-6}$ alkynyloxy($C_{1-6}$) alkyl, aryloxy($C_{1-6}$)alkyl, $C_{1-6}$ carboxyalkyl, $C_{1-6}$ alkylcarbonyl($C_{1-6}$)alkyl, $C_{2-6}$ alkenylcarbonyl($C_{1-6}$)alkyl, $C_{2-6}$ alkynylcarbonyl($C_{1-6}$)-alkyl, $C_{1-6}$ alkoxycarbonyl($C_{1-6}$) alkyl, $C_{3-6}$ alkenyloxycarbonyl($C_{1-6}$)alkyl, $C_{3-6}$ alkynyloxycarbonyl($C_{1-6}$)alkyl, aryloxycarbonyl($C_{1-6}$)alkyl, $C_{1-6}$ alkylthio($C_{1-6}$)alkyl, $C_{1-6}$ alkylsulfinyl($C_{1-6}$)alkyl, $C_{1-6}$ alkylsulfonyl($C_{1-6}$)alkyl, aminocarbonyl($C_{1-6}$)alkyl, $C_{1-6}$ alkylaminocarbonyl($C_{1-6}$)alkyl, di($C_{1-6}$)alkylaminocarbonyl ($C_{1-6}$)alkyl, phenyl($C_{1-4}$)alkyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl($C_{1-4}$)alkyl (wherein the heteroaryl group is optionally substituted by halo, nitro, cyano, $C_{1-6}$ alkyl, $C_{1-6}$ haloalkyl, $C_{1-6}$ alkoxy or $C_{1-6}$ haloalkoxy), heterocyclyl($C_{1-4}$)alkyl (wherein the heterocyclyl group is optionally substituted by halo, nitro, cyano, $C_{1-6}$ alkyl, $C_{1-6}$ haloalkyl, $C_{1-6}$ alkoxy or $C_{1-6}$ haloalkoxy), $C_{2-6}$ alkenyl, aminocarbonyl($C_{2-6}$)alkenyl, $C_{1-6}$ alkylaminocarbonyl($C_{2-6}$)alkenyl, di($C_{1-6}$)alkylaminocarbonyl($C_{2-6}$)alkenyl, phenyl($C_{2-4}$)-alkenyl, (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), $C_{2-6}$ alkynyl, trimethylsilyl($C_{2-6}$)alkynyl, aminocarbonyl($C_{2-6}$)alkynyl, $C_{1-6}$ alkylaminocarbonyl($C_{2-6}$) alkynyl, di($C_{1-6}$)alkylaminocarbonyl($C_{2-6}$)alkynyl, $C_{1-6}$ alkoxycarbonyl, $C_{3-7}$ cycloalkyl, $C_{3-7}$ halocycloalkyl, $C_{3-7}$ cyanocycloalkyl, $C_{1-3}$ alkyl($C_{3-7}$)-cycloalkyl, $C_{1-3}$ alkyl($C_{3-7}$)halocycloalkyl, phenyl (optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl (optionally substituted by halo, nitro, cyano, $C_{1-6}$ alkyl, $C_{1-6}$ haloalkyl, $C_{1-6}$ alkoxy or $C_{1-6}$ haloalkoxy), heterocyclyl (wherein the heterocyclyl group is optionally substituted by halo, nitro, cyano, $C_{1-6}$ alkyl, $C_{1-6}$ haloalkyl, $C_{1-6}$ alkoxy or $C_{1-6}$ haloalkoxy), or 2 adjacent groups $R^4$ together with the carbon atoms to which they are attached form a 4, 5, 6 or 7 membered carbocyclic or heterocyclic ring which may be optionally substituted by halogen, $C_{1-8}$ alkoxy, $C_{1-6}$ haloalkoxy, phenoxy (optionally substituted by halo, nitro, cyano, $C_{1-6}$ alkyl, $C_{1-6}$ haloalkyl, $C_{1-6}$ alkoxy or $C_{1-6}$ haloalkoxy), heteroaryloxy (optionally substituted by halo, nitro, cyano, $C_{1-6}$ alkyl, $C_{1-6}$ haloalkyl, $C_{1-6}$ alkoxy or $C_{1-6}$ haloalkoxy), $C_{1-8}$ alkylthio or $R^{19}R^{20}N$ where $R^{19}$ and $R^{20}$ are, independently, hydrogen, $C_{1-8}$ alkyl, $C_{3-7}$ cycloalkyl, $C_{3-6}$ alkenyl, $C_{3-6}$ alkynyl, $C_{2-6}$ haloalkyl, $C_{1-6}$ alkoxycarbonyl or $R^{19}$ and $R^{20}$ together with the N atom to which they are attached form a five, six or seven-membered heterocyclic ring which may contain one or two further heteroatoms selected from O, N or S and which may be optionally substituted by one or two $C_{1-6}$ alkyl groups; n is 0, 1, 2 or 3.

More preferably each $R^4$ is independently halogen, cyano, $C_{1-8}$ alkyl, $C_{1-8}$ haloalkyl, $C_{1-8}$ cyanoalkyl, $C_{1-6}$ alkoxy($C_{1-6}$)alkyl, $C_{2-6}$ alkynyl, trimethylsilyl($C_{2-6}$)allynyl, $C_{1-6}$ alkoxycarbonyl, $C_{3-7}$ cycloalkyl, $C_{1-3}$ alkyl ($C_{3-7}$) cycloalkyl, phenyl (optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heterocyclyl (optionally substituted by halo, nitro, cyano, $C_{1-6}$ alkyl, $C_{1-6}$ haloalkyl, $C_{1-6}$ alkoxy or $C_{1-6}$ haloalkoxy), $C_{1-8}$ alkoxy, $C_{1-6}$ haloalkoxy, phenoxy (optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryloxy (optionally substituted by halo, nitro, cyano, $C_{1-3}$ alkyl, $C_{1-3}$ haloalkyl, $C_{1-3}$ alkoxy or $C_{1-3}$ haloalkoxy), di($C_{1-8}$)alkylamino, or 2 adjacent groups $R^4$ together with the carbon atoms to which they are attached form a 4, 5, 6 or 7 membered carbocyclic or heterocyclic ring which may be optionally substituted by halogen; n is 0, 1, 2 or 3.

Even more preferably each $R^4$ is independently halogen, cyano, $C_{1-8}$ alkyl, $C_{1-8}$ haloalkyl, $C_{1-8}$ cyanoalkyl, $C_{1-6}$ alkoxy($C_{1-6}$)alkyl, $C_{2-6}$ alkynyl, heterocyclyl (optionally substituted by $C_{1-6}$ alkyl), $C_{1-8}$ alkoxy, $C_{1-6}$ haloalkoxy, phenoxy (optionally substituted by halo, cyano, $C_{1-3}$ alkyl or $C_{1-3}$ haloalkyl), heteroaryloxy (optionally substituted by halo, cyano, $C_{1-3}$ alkyl or $C_{1-3}$ haloalkyl), di($C_{1-8}$)alkylamino or 2 adjacent groups $R^4$ together with the carbon atoms to which they are attached form a 4, 5, 6 or 7 membered carbocyclic or heterocyclic ring which may be optionally substituted by halogen; n is 0, 1, 2 or 3.

Yet more preferably each $R^4$ is independently fluoro, chloro, bromo, cyano, $C_{1-4}$ alkyl, $C_{1-4}$ haloalkyl, $C_{1-4}$ cyanoalkyl or $C_{1-3}$ alkoxy($C_{1-3}$)alkyl; n is 0, 1 or 2.

Most preferably each $R^4$ is independently fluoro, chloro, bromo, $C_{1-4}$ alkyl or $C_{1-4}$ haloalkyl; n is 1 or 2.

Preferably $R^8$ is $C_{1-10}$ alkyl, $C_{1-10}$ haloalkyl, aryl($C_{1-6}$) alkyl (wherein the aryl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl($C_{1-6}$)alkyl (wherein the heteroaryl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), arylcarbonyl-($C_{1-6}$)alkyl (wherein the aryl group may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino and the alkyl group may be optionally substituted by aryl), $C_{2-8}$ alkenyl, $C_{2-8}$ haloalkenyl, aryl($C_{2-6}$)-alkenyl (wherein the aryl group is optionally substituted halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino, $C_{1-6}$ alkoxycarbonyl, or two adjacent substituents can cyclise to form a 5, 6 or 7 membered carbocyclic or heterocyclic ring), heteroaryl($C_{2-6}$)-alkenyl (wherein the heteroaryl group is optionally substituted halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino, $C_{1-6}$ alkoxycarbonyl, or two adjacent substituents can cyclise to form a 5, 6 or 7 membered carbocyclic or heterocyclic ring), $C_{2-6}$ alkynyl, phenyl($C_{2-6}$)alkynyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), $C_{3-7}$ cycloalkyl, $C_{1-6}$ alkoxycarbonyl, $C_{1-6}$ alkylcarbonyl, $C_{1-6}$ haloalkylcarbonyl or aryl($C_{2-6}$)alkenylcarbonyl (wherein the aryl group may be optionally substituted halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), or $—C(R^{51})(R^{52})—[CR^{53}=CR^{54}]z-R^{55}$ where z is 1 or 2, $R^{51}$ and $R^{52}$ are each independently H, halo or $C_{1-2}$ alkyl, $R^{53}$ and $R^{54}$ are each independently H, halogen, $C_{1-4}$ alkyl or $C_{1-4}$ haloalkyl and $R^{55}$ is optionally substituted aryl or optionally substituted heteroaryl.

More preferably $R^8$ is phenyl($C_{1-4}$)alkyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl($C_{1-6}$)alkyl (wherein the heteroaryl group is optionally substituted halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), phenyl ($C_{2-6}$)alkenyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl($C_{2-6}$)alkenyl (wherein the heteroaryl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino) or phenyl($C_{2-6}$)alkynyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino, or $—C(R^{51})(R^{52})—[CR^{53}=CR^{54}]z-R^{55}$ where z is 1 or 2, $R^{51}$ and $R^{52}$ are each independently H, halo or $C_{1-2}$ alkyl, $R^{53}$ and $R^{54}$ are each independently H, halogen, $C_{1-4}$ alkyl or $C_{1-4}$ haloalkyl and $R^{55}$ is optionally substituted aryl or optionally substituted heteroaryl.

Most preferably $R^8$ is —C($R^{51}$)($R^{52}$)—[C$R^{53}$=C$R^{54}$]z-$R^{55}$ where z is 1 or 2, preferably 1, $R^{51}$ and $R^{52}$ are each independently H, halo or $C_{1-2}$ alkyl, $R^{53}$ and $R^{54}$ are each independently H, halogen, $C_{1-4}$ alkyl or $C_{1-4}$ haloalkyl and $R^{55}$ is phenyl substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino or heteroaryl substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino.

$R^{51}$ and $R^{52}$ are preferably hydrogen.

$R^{53}$ and $R^{54}$ are preferably hydrogen or halogen, especially hydrogen. $R^{55}$ is preferably phenyl substituted with one to three substituents selected from halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino.

Preferably each Ra is independently hydrogen, halo, cyano, $C_{1-3}$ alkyl, hydroxy or two Ra groups together with the carbon atom to which they are attached form a carbonyl group More preferably each Ra is independently hydrogen, fluoro, methyl, hydroxy or two Ra groups together with the carbon atom to which they are attached form a carbonyl group Most preferably each Ra is hydrogen.

Preferably p is 1, 2 or 3 and q is 1, 2 or 3 and p+q is 2 or 3.

More preferably p is 1 or 2 and q is 2.

Most preferably p and q are both 2.

The compounds in Tables I to LXX below illustrate the compounds of the invention.

Table I provides 782 compounds of formula Ia

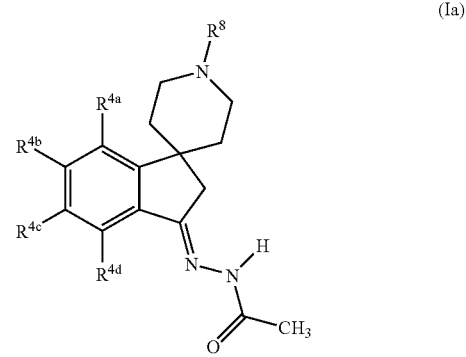

(Ia)

wherein the values of $R^8$, $R^{4a}$, $R^{4b}$, $R^{4c}$ and $R^{4d}$ are given in Table 1

TABLE 1

| Compound No | $R^8$ | $R^{4a}$ | $R^{4b}$ | $R^{4c}$ | $R^{4d}$ |
|---|---|---|---|---|---|
| I-1 | 4-chlorobenzyl | H | H | H | H |
| I-2 | Cinnamyl | H | H | H | H |
| I-3 | 4-chlorocinnamyl | H | H | H | H |
| I-4 | 4-fluorocinnamyl | H | H | H | H |
| I-5 | 4-bromocinnamyl | H | H | H | H |
| I-6 | 4-trifluoromethylcinnamyl | H | H | H | H |
| I-7 | 4-trifluoromethoxycinnamyl | H | H | H | H |
| I-8 | 4-pentafluoroethoxycinnamyl | H | H | H | H |
| I-9 | 4-methoxycinnamyl | H | H | H | H |
| I-10 | 4-ethoxycinnamyl | H | H | H | H |
| I-11 | 4-cyanocinnamyl | H | H | H | H |
| I-12 | 3-(6-chloro-pyridin-3-yl)-allyl | H | H | H | H |
| I-13 | 3-(4-chlorophenyl)-but-2-enyl | H | H | H | H |
| I-14 | 3-(4-chlorophenyl)-3-fluoro-allyl | H | H | H | H |
| I-15 | 3-chloro-4-fluoro-cinnamyl | H | H | H | H |
| I-16 | 3,5-dichloro-cinnamyl | H | H | H | H |
| I-17 | 5-phenyl-penta-2,4-dienyl | H | H | H | H |
| I-18 | 4-isopropyloxycarbonylamino-cinnamyl | H | H | H | H |
| I-19 | 3-naphthalen-2-yl-allyl | H | H | H | H |
| I-20 | 3-(5-trifluoromethyl-pyridin-2-yl)-allyl | H | H | H | H |
| I-21 | 3-(5-chloro-pyridin-2-yl)-allyl | H | H | H | H |
| I-22 | 3-pyridin-4-yl-allyl | H | H | H | H |
| I-23 | 3-(2-Chloro-pyridin-4-yl)-allyl | H | H | H | H |
| I-24 | 4-chlorobenzyl | H | F | H | H |
| I-25 | Cinnamyl | H | F | H | H |
| I-26 | 4-chlorocinnamyl | H | F | H | H |
| I-27 | 4-fluorocinnamyl | H | F | H | H |
| I-28 | 4-bromocinnamyl | H | F | H | H |
| I-29 | 4-trifluoromethylcinnamyl | H | F | H | H |
| I-30 | 4-trifluoromethoxycinnamyl | H | F | H | H |
| I-31 | 4-pentafluoroethoxycinnamyl | H | F | H | H |
| I-32 | 4-methoxycinnamyl | H | F | H | H |
| I-33 | 4-ethoxycinnamyl | H | F | H | H |
| I-34 | 4-cyanocinnamyl | H | F | H | H |
| I-35 | 3-(6-chloro-pyridin-3-yl)-allyl | H | F | H | H |
| I-36 | 3-(4-chlorophenyl)-but-2-enyl | H | F | H | H |
| I-37 | 3-(4-chlorophenyl)-3-fluoro-allyl | H | F | H | H |
| I-38 | 3-chloro-4-fluoro-cinnamyl | H | F | H | H |
| I-39 | 3,5-dichloro-cinnamyl | H | F | H | H |
| I-40 | 5-phenyl-penta-2,4-dienyl | H | F | H | H |
| I-41 | 4-isopropyloxycarbonylamino-cinnamyl | H | F | H | H |
| I-42 | 3-naphthalen-2-yl-allyl | H | F | H | H |
| I-43 | 3-(5-trifluoromethyl-pyridin-2-yl)-allyl | H | F | H | H |
| I-44 | 3-(5-chloro-pyridin-2-yl)-allyl | H | F | H | H |
| I-45 | 3-pyridin-4-yl-allyl | H | F | H | H |
| I-46 | 3-(2-Chloro-pyridin-4-yl)-allyl | H | F | H | H |

TABLE 1-continued

| Compound No | R⁸ | R⁴ᵃ | R⁴ᵇ | R⁴ᶜ | R⁴ᵈ |
|---|---|---|---|---|---|
| I-47 | 4-chlorobenzyl | H | Cl | H | H |
| I-48 | Cinnamyl | H | Cl | H | H |
| I-49 | 4-chlorocinnamyl | H | Cl | H | H |
| I-50 | 4-fluorocinnamyl | H | Cl | H | H |
| I-51 | 4-bromocinnamyl | H | Cl | H | H |
| I-52 | 4-trifluoromethylcinnamyl | H | Cl | H | H |
| I-53 | 4-trifluoromethoxycinnamyl | H | Cl | H | H |
| I-54 | 4-pentafluoroethoxycinnamyl | H | Cl | H | H |
| I-55 | 4-methoxycinnamyl | H | Cl | H | H |
| I-56 | 4-ethoxycinnamyl | H | Cl | H | H |
| I-57 | 4-cyanocinnamyl | H | Cl | H | H |
| I-58 | 3-(6-chloro-pyridin-3-yl)-allyl | H | Cl | H | H |
| I-59 | 3-(4-chlorophenyl)-but-2-enyl | H | Cl | H | H |
| I-60 | 3-(4-chlorophenyl)-3-fluoro-allyl | H | Cl | H | H |
| I-61 | 3-chloro-4-fluoro-cinnamyl | H | Cl | H | H |
| I-62 | 3,5-dichloro-cinnamyl | H | Cl | H | H |
| I-63 | 5-phenyl-penta-2,4-dienyl | H | Cl | H | H |
| I-64 | 4-isopropyloxycarbonylamino-cinnamyl | H | Cl | H | H |
| I-65 | 3-naphthalen-2-yl-allyl | H | Cl | H | H |
| I-66 | 3-(5-trifluoromethyl-pyridin-2-yl)-allyl | H | Cl | H | H |
| I-67 | 3-(5-chloro-pyridin-2-yl)-allyl | H | Cl | H | H |
| I-68 | 3-pyridin-4-yl-allyl | H | Cl | H | H |
| I-69 | 3-(2-Chloro-pyridin-4-yl)-allyl | H | Cl | H | H |
| I-70 | 4-chlorobenzyl | H | Br | H | H |
| I-71 | Cinnamyl | H | Br | H | H |
| I-72 | 4-chlorocinnamyl | H | Br | H | H |
| I-73 | 4-fluorocinnamyl | H | Br | H | H |
| I-74 | 4-bromocinnamyl | H | Br | H | H |
| I-75 | 4-trifluoromethylcinnamyl | H | Br | H | H |
| I-76 | 4-trifluoromethoxycinnamyl | H | Br | H | H |
| I-77 | 4-pentafluoroethoxycinnamyl | H | Br | H | H |
| I-78 | 4-methoxycinnamyl | H | Br | H | H |
| I-79 | 4-ethoxycinnamyl | H | Br | H | H |
| I-80 | 4-cyanocinnamyl | H | Br | H | H |
| I-81 | 3-(6-chloro-pyridin-3-yl)-allyl | H | Br | H | H |
| I-82 | 3-(4-chlorophenyl)-but-2-enyl | H | Br | H | H |
| I-83 | 3-(4-chlorophenyl)-3-fluoro-allyl | H | Br | H | H |
| I-84 | 3-chloro-4-fluoro-cinnamyl | H | Br | H | H |
| I-85 | 3,5-dichloro-cinnamyl | H | Br | H | H |
| I-86 | 5-phenyl-penta-2,4-dienyl | H | Br | H | H |
| I-87 | 4-isopropyloxycarbonylamino-cinnamyl | H | Br | H | H |
| I-88 | 3-naphthalen-2-yl-allyl | H | Br | H | H |
| I-89 | 3-(5-trifluoromethyl-pyridin-2-yl)-allyl | H | Br | H | H |
| I-90 | 3-(5-chloro-pyridin-2-yl)-allyl | H | Br | H | H |
| I-91 | 3-pyridin-4-yl-allyl | H | Br | H | H |
| I-92 | 3-(2-Chloro-pyridin-4-yl)-allyl | H | Br | H | H |
| I-93 | 4-chlorobenzyl | H | CN | H | H |
| I-94 | Cinnamyl | H | CN | H | H |
| I-95 | 4-chlorocinnamyl | H | CN | H | H |
| I-96 | 4-fluorocinnamyl | H | CN | H | H |
| I-97 | 4-bromocinnamyl | H | CN | H | H |
| I-98 | 4-trifluoromethylcinnamyl | H | CN | H | H |
| I-99 | 4-trifluoromethoxycinnamyl | H | CN | H | H |
| I-100 | 4-pentafluoroethoxycinnamyl | H | CN | H | H |
| I-101 | 4-methoxycinnamyl | H | CN | H | H |
| I-102 | 4-ethoxycinnamyl | H | CN | H | H |
| I-103 | 4-cyanocinnamyl | H | CN | H | H |
| I-104 | 3-(6-chloro-pyridin-3-yl)-allyl | H | CN | H | H |
| I-105 | 3-(4-chlorophenyl)-but-2-enyl | H | CN | H | H |
| I-106 | 3-(4-chlorophenyl)-3-fluoro-allyl | H | CN | H | H |
| I-107 | 3-chloro-4-fluoro-cinnamyl | H | CN | H | H |
| I-108 | 3,5-dichloro-cinnamyl | H | CN | H | H |
| I-109 | 5-phenyl-penta-2,4-dienyl | H | CN | H | H |
| I-110 | 4-isopropyloxycarbonylamino-cinnamyl | H | CN | H | H |
| I-111 | 3-naphthalen-2-yl-allyl | H | CN | H | H |
| I-112 | 3-(5-trifluoromethyl-pyridin-2-yl)-allyl | H | CN | H | H |
| I-113 | 3-(5-chloro-pyridin-2-yl)-allyl | H | CN | H | H |
| I-114 | 3-pyridin-4-yl-allyl | H | CN | H | H |
| I-115 | 3-(2-Chloro-pyridin-4-yl)-allyl | H | CN | H | H |
| I-116 | 4-chlorobenzyl | H | OMe | H | H |
| I-117 | Cinnamyl | H | OMe | H | H |
| I-118 | 4-chlorocinnamyl | H | OMe | H | H |
| I-119 | 4-fluorocinnamyl | H | OMe | H | H |
| I-120 | 4-bromocinnamyl | H | OMe | H | H |
| I-121 | 4-trifluoromethylcinnamyl | H | OMe | H | H |
| I-122 | 4-trifluoromethoxycinnamyl | H | OMe | H | H |
| I-123 | 4-pentafluoroethoxycinnamyl | H | OMe | H | H |
| I-124 | 4-methoxycinnamyl | H | OMe | H | H |

TABLE 1-continued

| Compound No | R[8] | R[4a] | R[4b] | R[4c] | R[4d] |
|---|---|---|---|---|---|
| I-125 | 4-ethoxycinnamyl | H | OMe | H | H |
| I-126 | 4-cyanocinnamyl | H | OMe | H | H |
| I-127 | 3-(6-chloro-pyridin-3-yl)-allyl | H | OMe | H | H |
| I-128 | 3-(4-chlorophenyl)-but-2-enyl | H | OMe | H | H |
| I-129 | 3-(4-chlorophenyl)-3-fluoro-allyl | H | OMe | H | H |
| I-130 | 3-chloro-4-fluoro-cinnamyl | H | OMe | H | H |
| I-131 | 3,5-dichloro-cinnamyl | H | OMe | H | H |
| I-132 | 5-phenyl-penta-2,4-dienyl | H | OMe | H | H |
| I-133 | 4-isopropyloxycarbonylamino-cinnamyl | H | OMe | H | H |
| I-134 | 3-naphthalen-2-yl-allyl | H | OMe | H | H |
| I-135 | 3-(5-trifluoromethyl-pyridin-2-yl)-allyl | H | OMe | H | H |
| I-136 | 3-(5-chloro-pyridin-2-yl)-allyl | H | OMe | H | H |
| I-137 | 3-pyridin-4-yl-allyl | H | OMe | H | H |
| I-138 | 3-(2-Chloro-pyridin-4-yl)-allyl | H | OMe | H | H |
| I-139 | 4-chlorobenzyl | H | $OCF_3$ | H | H |
| I-140 | Cinnamyl | H | $OCF_3$ | H | H |
| I-141 | 4-chlorocinnamyl | H | $OCF_3$ | H | H |
| I-142 | 4-fluorocinnamyl | H | $OCF_3$ | H | H |
| I-143 | 4-bromocinnamyl | H | $OCF_3$ | H | H |
| I-144 | 4-trifluoromethylcinnamyl | H | $OCF_3$ | H | H |
| I-145 | 4-trifluoromethoxycinnamyl | H | $OCF_3$ | H | H |
| I-146 | 4-pentafluoroethoxycinnamyl | H | $OCF_3$ | H | H |
| I-147 | 4-methoxycinnamyl | H | $OCF_3$ | H | H |
| I-148 | 4-ethoxycinnamyl | H | $OCF_3$ | H | H |
| I-149 | 4-cyanocinnamyl | H | $OCF_3$ | H | H |
| I-150 | 3-(6-chloro-pyridin-3-yl)-allyl | H | $OCF_3$ | H | H |
| I-151 | 3-(4-chlorophenyl)-but-2-enyl | H | $OCF_3$ | H | H |
| I-152 | 3-(4-chlorophenyl)-3-fluoro-allyl | H | $OCF_3$ | H | H |
| I-153 | 3-chloro-4-fluoro-cinnamyl | H | $OCF_3$ | H | H |
| I-154 | 3,5-dichloro-cinnamyl | H | $OCF_3$ | H | H |
| I-155 | 5-phenyl-penta-2,4-dienyl | H | $OCF_3$ | H | H |
| I-156 | 4-isopropyloxycarbonylamino-cinnamyl | H | $OCF_3$ | H | H |
| I-157 | 3-naphthalen-2-yl-allyl | H | $OCF_3$ | H | H |
| I-158 | 3-(5-trifluoromethyl-pyridin-2-yl)-allyl | H | $OCF_3$ | H | H |
| I-159 | 3-(5-chloro-pyridin-2-yl)-allyl | H | $OCF_3$ | H | H |
| I-160 | 3-pyridin-4-yl-allyl | H | $OCF_3$ | H | H |
| I-161 | 3-(2-Chloro-pyridin-4-yl)-allyl | H | $OCF_3$ | H | H |
| I-162 | 4-chlorobenzyl | H | $CH_3$ | H | H |
| I-163 | Cinnamyl | H | $CH_3$ | H | H |
| I-164 | 4-chlorocinnamyl | H | $CH_3$ | H | H |
| I-165 | 4-fluorocinnamyl | H | $CH_3$ | H | H |
| I-166 | 4-bromocinnamyl | H | $CH_3$ | H | H |
| I-167 | 4-trifluoromethylcinnamyl | H | $CH_3$ | H | H |
| I-168 | 4-trifluoromethoxycinnamyl | H | $CH_3$ | H | H |
| I-169 | 4-pentafluoroethoxycinnamyl | H | $CH_3$ | H | H |
| I-170 | 4-methoxycinnamyl | H | $CH_3$ | H | H |
| I-171 | 4-ethoxycinnamyl | H | $CH_3$ | H | H |
| I-172 | 4-cyanocinnamyl | H | $CH_3$ | H | H |
| I-173 | 3-(6-chloro-pyridin-3-yl)-allyl | H | $CH_3$ | H | H |
| I-174 | 3-(4-chlorophenyl)-but-2-enyl | H | $CH_3$ | H | H |
| I-175 | 3-(4-chlorophenyl)-3-fluoro-allyl | H | $CH_3$ | H | H |
| I-176 | 3-chloro-4-fluoro-cinnamyl | H | $CH_3$ | H | H |
| I-177 | 3,5-dichloro-cinnamyl | H | $CH_3$ | H | H |
| I-178 | 5-phenyl-penta-2,4-dienyl | H | $CH_3$ | H | H |
| I-179 | 4-isopropyloxycarbonylamino-cinnamyl | H | $CH_3$ | H | H |
| I-180 | 3-naphthalen-2-yl-allyl | H | $CH_3$ | H | H |
| I-181 | 3-(5-trifluoromethyl-pyridin-2-yl)-allyl | H | $CH_3$ | H | H |
| I-182 | 3-(5-chloro-pyridin-2-yl)-allyl | H | $CH_3$ | H | H |
| I-183 | 3-pyridin-4-yl-allyl | H | $CH_3$ | H | H |
| I-184 | 3-(2-Chloro-pyridin-4-yl)-allyl | H | $CH_3$ | H | H |
| I-185 | 4-chlorobenzyl | H | $CF_3$ | H | H |
| I-186 | Cinnamyl | H | $CF_3$ | H | H |
| I-187 | 4-chlorocinnamyl | H | $CF_3$ | H | H |
| I-188 | 4-fluorocinnamyl | H | $CF_3$ | H | H |
| I-189 | 4-bromocinnamyl | H | $CF_3$ | H | H |
| I-190 | 4-trifluoromethylcinnamyl | H | $CF_3$ | H | H |
| I-191 | 4-trifluoromethoxycinnamyl | H | $CF_3$ | H | H |
| I-192 | 4-pentafluoroethoxycinnamyl | H | $CF_3$ | H | H |
| I-193 | 4-methoxycinnamyl | H | $CF_3$ | H | H |
| I-194 | 4-ethoxycinnamyl | H | $CF_3$ | H | H |
| I-195 | 4-cyanocinnamyl | H | $CF_3$ | H | H |
| I-196 | 3-(6-chloro-pyridin-3-yl)-allyl | H | $CF_3$ | H | H |
| I-197 | 3-(4-chlorophenyl)-but-2-enyl | H | $CF_3$ | H | H |
| I-198 | 3-(4-chlorophenyl)-3-fluoro-allyl | H | $CF_3$ | H | H |
| I-199 | 3-chloro-4-fluoro-cinnamyl | H | $CF_3$ | H | H |
| I-200 | 3,5-dichloro-cinnamyl | H | $CF_3$ | H | H |
| I-201 | 5-phenyl-penta-2,4-dienyl | H | $CF_3$ | H | H |
| I-202 | 4-isopropyloxycarbonylamino-cinnamyl | H | $CF_3$ | H | H |

TABLE 1-continued

| Compound No | R$^8$ | R$^{4a}$ | R$^{4b}$ | R$^{4c}$ | R$^{4d}$ |
|---|---|---|---|---|---|
| I-203 | 3-naphthalen-2-yl-allyl | H | CF$_3$ | H | H |
| I-204 | 3-(5-trifluoromethyl-pyridin-2-yl)-allyl | H | CF$_3$ | H | H |
| I-205 | 3-(5-chloro-pyridin-2-yl)-allyl | H | CF$_3$ | H | H |
| I-206 | 3-pyridin-4-yl-allyl | H | CF$_3$ | H | H |
| I-207 | 3-(2-Chloro-pyridin-4-yl)-allyl | H | CF$_3$ | H | H |
| I-208 | 4-chlorobenzyl | H | H | Cl | H |
| I-209 | Cinnamyl | H | H | Cl | H |
| I-210 | 4-chlorocinnamyl | H | H | Cl | H |
| I-211 | 4-fluorocinnamyl | H | H | Cl | H |
| I-212 | 4-bromocinnamyl | H | H | Cl | H |
| I-213 | 4-trifluoromethylcinnamyl | H | H | Cl | H |
| I-214 | 4-trifluoromethoxycinnamyl | H | H | Cl | H |
| I-215 | 4-pentafluoroethoxycinnamyl | H | H | Cl | H |
| I-216 | 4-methoxycinnamyl | H | H | Cl | H |
| I-217 | 4-ethoxycinnamyl | H | H | Cl | H |
| I-218 | 4-cyanocinnamyl | H | H | Cl | H |
| I-219 | 3-(6-chloro-pyridin-3-yl)-allyl | H | H | Cl | H |
| I-220 | 3-(4-chlorophenyl)-but-2-enyl | H | H | Cl | H |
| I-221 | 3-(4-chlorophenyl)-3-fluoro-allyl | H | H | Cl | H |
| I-222 | 3-chloro-4-fluoro-cinnamyl | H | H | Cl | H |
| I-223 | 3,5-dichloro-cinnamyl | H | H | Cl | H |
| I-224 | 5-phenyl-penta-2,4-dienyl | H | H | Cl | H |
| I-225 | 4-isopropyloxycarbonylamino-cinnamyl | H | H | Cl | H |
| I-226 | 3-naphthalen-2-yl-allyl | H | H | Cl | H |
| I-227 | 3-(5-trifluoromethyl-pyridin-2-yl)-allyl | H | H | Cl | H |
| I-228 | 3-(5-chloro-pyridin-2-yl)-allyl | H | H | Cl | H |
| I-229 | 3-pyridin-4-yl-allyl | H | H | Cl | H |
| I-230 | 3-(2-Chloro-pyridin-4-yl)-allyl | H | H | Cl | H |
| I-231 | 4-chlorobenzyl | H | H | F | H |
| I-232 | Cinnamyl | H | H | F | H |
| I-233 | 4-chlorocinnamyl | H | H | F | H |
| I-234 | 4-fluorocinnamyl | H | H | F | H |
| I-235 | 4-bromocinnamyl | H | H | F | H |
| I-236 | 4-trifluoromethylcinnamyl | H | H | F | H |
| I-237 | 4-trifluoromethoxycinnamyl | H | H | F | H |
| I-238 | 4-pentafluoroethoxycinnamyl | H | H | F | H |
| I-239 | 4-methoxycinnamyl | H | H | F | H |
| I-240 | 4-ethoxycinnamyl | H | H | F | H |
| I-241 | 4-cyanocinnamyl | H | H | F | H |
| I-242 | 3-(6-chloro-pyridin-3-yl)-allyl | H | H | F | H |
| I-243 | 3-(4-chlorophenyl)-but-2-enyl | H | H | F | H |
| I-244 | 3-(4-chlorophenyl)-3-fluoro-allyl | H | H | F | H |
| I-245 | 3-chloro-4-fluoro-cinnamyl | H | H | F | H |
| I-246 | 3,5-dichloro-cinnamyl | H | H | F | H |
| I-247 | 5-phenyl-penta-2,4-dienyl | H | H | F | H |
| I-248 | 4-isopropyloxycarbonylamino-cinnamyl | H | H | F | H |
| I-249 | 3-naphthalen-2-yl-allyl | H | H | F | H |
| I-250 | 3-(5-trifluoromethyl-pyridin-2-yl)-allyl | H | H | F | H |
| I-251 | 3-(5-chloro-pyridin-2-yl)-allyl | H | H | F | H |
| I-252 | 3-pyridin-4-yl-allyl | H | H | F | H |
| I-253 | 3-(2-Chloro-pyridin-4-yl)-allyl | H | H | F | H |
| I-254 | 4-chlorobenzyl | H | H | Br | H |
| I-255 | Cinnamyl | H | H | Br | H |
| I-256 | 4-chlorocinnamyl | H | H | Br | H |
| I-257 | 4-fluorocinnamyl | H | H | Br | H |
| I-258 | 4-bromocinnamyl | H | H | Br | H |
| I-259 | 4-trifluoromethylcinnamyl | H | H | Br | H |
| I-260 | 4-trifluoromethoxycinnamyl | H | H | Br | H |
| I-261 | 4-pentafluoroethoxycinnamyl | H | H | Br | H |
| I-262 | 4-methoxycinnamyl | H | H | Br | H |
| I-263 | 4-ethoxycinnamyl | H | H | Br | H |
| I-264 | 4-cyanocinnamyl | H | H | Br | H |
| I-265 | 3-(6-chloro-pyridin-3-yl)-allyl | H | H | Br | H |
| I-266 | 3-(4-chlorophenyl)-but-2-enyl | H | H | Br | H |
| I-267 | 3-(4-chlorophenyl)-3-fluoro-allyl | H | H | Br | H |
| I-268 | 3-chloro-4-fluoro-cinnamyl | H | H | Br | H |
| I-269 | 3,5-dichloro-cinnamyl | H | H | Br | H |
| I-270 | 5-phenyl-penta-2,4-dienyl | H | H | Br | H |
| I-271 | 4-isopropyloxycarbonylamino-cinnamyl | H | H | Br | H |
| I-272 | 3-naphthalen-2-yl-allyl | H | H | Br | H |
| I-273 | 3-(5-trifluoromethyl-pyridin-2-yl)-allyl | H | H | Br | H |
| I-274 | 3-(5-chloro-pyridin-2-yl)-allyl | H | H | Br | H |
| I-275 | 3-pyridin-4-yl-allyl | H | H | Br | H |
| I-276 | 3-(2-Chloro-pyridin-4-yl)-allyl | H | H | Br | H |
| I-277 | 4-chlorobenzyl | H | H | OCF$_3$ | H |
| I-278 | Cinnamyl | H | H | OCF$_3$ | H |
| I-279 | 4-chlorocinnamyl | H | H | OCF$_3$ | H |
| I-280 | 4-fluorocinnamyl | H | H | OCF$_3$ | H |

TABLE 1-continued

| Compound No | R⁸ | R⁴ᵃ | R⁴ᵇ | R⁴ᶜ | R⁴ᵈ |
|---|---|---|---|---|---|
| I-281 | 4-bromocinnamyl | H | H | OCF₃ | H |
| I-282 | 4-trifluoromethylcinnamyl | H | H | OCF₃ | H |
| I-283 | 4-trifluoromethoxycinnamyl | H | H | OCF₃ | H |
| I-284 | 4-pentafluoroethoxycinnamyl | H | H | OCF₃ | H |
| I-285 | 4-methoxycinnamyl | H | H | OCF₃ | H |
| I-286 | 4-ethoxycinnamyl | H | H | OCF₃ | H |
| I-287 | 4-cyanocinnamyl | H | H | OCF₃ | H |
| I-288 | 3-(6-chloro-pyridin-3-yl)-allyl | H | H | OCF₃ | H |
| I-289 | 3-(4-chlorophenyl)-but-2-enyl | H | H | OCF₃ | H |
| I-290 | 3-(4-chlorophenyl)-3-fluoro-allyl | H | H | OCF₃ | H |
| I-291 | 3-chloro-4-fluoro-cinnamyl | H | H | OCF₃ | H |
| I-292 | 3,5-dichloro-cinnamyl | H | H | OCF₃ | H |
| I-293 | 5-phenyl-penta-2,4-dienyl | H | H | OCF₃ | H |
| I-294 | 4-isopropyloxycarbonylamino-cinnamyl | H | H | OCF₃ | H |
| I-295 | 3-naphthalen-2-yl-allyl | H | H | OCF₃ | H |
| I-296 | 3-(5-trifluoromethyl-pyridin-2-yl)-allyl | H | H | OCF₃ | H |
| I-297 | 3-(5-chloro-pyridin-2-yl)-allyl | H | H | OCF₃ | H |
| I-298 | 3-pyridin-4-yl-allyl | H | H | OCF₃ | H |
| I-299 | 3-(2-Chloro-pyridin-4-yl)-allyl | H | H | OCF₃ | H |
| I-300 | 4-chlorobenzyl | H | H | CH₃ | H |
| I-301 | Cinnamyl | H | H | CH₃ | H |
| I-302 | 4-chlorocinnamyl | H | H | CH₃ | H |
| I-303 | 4-fluorocinnamyl | H | H | CH₃ | H |
| I-304 | 4-bromocinnamyl | H | H | CH₃ | H |
| I-305 | 4-trifluoromethylcinnamyl | H | H | CH₃ | H |
| I-306 | 4-trifluoromethoxycinnamyl | H | H | CH₃ | H |
| I-307 | 4-pentafluoroethoxycinnamyl | H | H | CH₃ | H |
| I-308 | 4-methoxycinnamyl | H | H | CH₃ | H |
| I-309 | 4-ethoxycinnamyl | H | H | CH₃ | H |
| I-310 | 4-cyanocinnamyl | H | H | CH₃ | H |
| I-311 | 3-(6-chloro-pyridin-3-yl)-allyl | H | H | CH₃ | H |
| I-312 | 3-(4-chlorophenyl)-but-2-enyl | H | H | CH₃ | H |
| I-313 | 3-(4-chlorophenyl)-3-fluoro-allyl | H | H | CH₃ | H |
| I-314 | 3-chloro-4-fluoro-cinnamyl | H | H | CH₃ | H |
| I-315 | 3,5-dichloro-cinnamyl | H | H | CH₃ | H |
| I-316 | 5-phenyl-penta-2,4-dienyl | H | H | CH₃ | H |
| I-317 | 4-isopropyloxycarbonylamino-cinnamyl | H | H | CH₃ | H |
| I-318 | 3-naphthalen-2-yl-allyl | H | H | CH₃ | H |
| I-319 | 3-(5-trifluoromethyl-pyridin-2-yl)-allyl | H | H | CH₃ | H |
| I-320 | 3-(5-chloro-pyridin-2-yl)-allyl | H | H | CH₃ | H |
| I-321 | 3-pyridin-4-yl-allyl | H | H | CH₃ | H |
| I-322 | 3-(2-Chloro-pyridin-4-yl)-allyl | H | H | CH₃ | H |
| I-323 | 4-chlorobenzyl | H | H | CF₃ | H |
| I-324 | Cinnamyl | H | H | CF₃ | H |
| I-325 | 4-chlorocinnamyl | H | H | CF₃ | H |
| I-326 | 4-fluorocinnamyl | H | H | CF₃ | H |
| I-327 | 4-bromocinnamyl | H | H | CF₃ | H |
| I-328 | 4-trifluoromethylcinnamyl | H | H | CF₃ | H |
| I-329 | 4-trifluoromethoxycinnamyl | H | H | CF₃ | H |
| I-330 | 4-pentafluoroethoxycinnamyl | H | H | CF₃ | H |
| I-331 | 4-methoxycinnamyl | H | H | CF₃ | H |
| I-332 | 4-ethoxycinnamyl | H | H | CF₃ | H |
| I-333 | 4-cyanocinnamyl | H | H | CF₃ | H |
| I-334 | 3-(6-chloro-pyridin-3-yl)-allyl | H | H | CF₃ | H |
| I-335 | 3-(4-chlorophenyl)-but-2-enyl | H | H | CF₃ | H |
| I-336 | 3-(4-chlorophenyl)-3-fluoro-allyl | H | H | CF₃ | H |
| I-337 | 3-chloro-4-fluoro-cinnamyl | H | H | CF₃ | H |
| I-338 | 3,5-dichloro-cinnamyl | H | H | CF₃ | H |
| I-339 | 5-phenyl-penta-2,4-dienyl | H | H | CF₃ | H |
| I-340 | 4-isopropyloxycarbonylamino-cinnamyl | H | H | CF₃ | H |
| I-341 | 3-naphthalen-2-yl-allyl | H | H | CF₃ | H |
| I-342 | 3-(5-trifluoromethyl-pyridin-2-yl)-allyl | H | H | CF₃ | H |
| I-343 | 3-(5-chloro-pyridin-2-yl)-allyl | H | H | CF₃ | H |
| I-344 | 3-pyridin-4-yl-allyl | H | H | CF₃ | H |
| I-345 | 3-(2-Chloro-pyridin-4-yl)-allyl | H | H | CF₃ | H |
| I-346 | 4-chlorobenzyl | F | H | H | H |
| I-347 | Cinnamyl | F | H | H | H |
| I-348 | 4-chlorocinnamyl | F | H | H | H |
| I-349 | 4-fluorocinnamyl | F | H | H | H |
| I-350 | 4-bromocinnamyl | F | H | H | H |
| I-351 | 4-trifluoromethylcinnamyl | F | H | H | H |
| I-352 | 4-trifluoromethoxycinnamyl | F | H | H | H |
| I-353 | 4-pentafluoroethoxycinnamyl | F | H | H | H |
| I-354 | 4-methoxycinnamyl | F | H | H | H |
| I-355 | 4-ethoxycinnamyl | F | H | H | H |
| I-356 | 4-cyanocinnamyl | F | H | H | H |
| I-357 | 3-(6-chloro-pyridin-3-yl)-allyl | F | H | H | H |
| I-358 | 3-(4-chlorophenyl)-but-2-enyl | F | H | H | H |

TABLE 1-continued

| Compound No | R⁸ | R⁴ᵃ | R⁴ᵇ | R⁴ᶜ | R⁴ᵈ |
|---|---|---|---|---|---|
| I-359 | 3-(4-chlorophenyl)-3-fluoro-allyl | F | H | H | H |
| I-360 | 3-chloro-4-fluoro-cinnamyl | F | H | H | H |
| I-361 | 3,5-dichloro-cinnamyl | F | H | H | H |
| I-362 | 5-phenyl-penta-2,4-dienyl | F | H | H | H |
| I-363 | 4-isopropyloxycarbonylamino-cinnamyl | F | H | H | H |
| I-364 | 3-naphthalen-2-yl-allyl | F | H | H | H |
| I-365 | 3-(5-trifluoromethyl-pyridin-2-yl)-allyl | F | H | H | H |
| I-366 | 3-(5-chloro-pyridin-2-yl)-allyl | F | H | H | H |
| I-367 | 3-pyridin-4-yl-allyl | F | H | H | H |
| I-368 | 3-(2-Chloro-pyridin-4-yl)-allyl | F | H | H | H |
| I-369 | 4-chlorobenzyl | Cl | H | H | H |
| I-370 | Cinnamyl | Cl | H | H | H |
| I-371 | 4-chlorocinnamyl | Cl | H | H | H |
| I-372 | 4-fluorocinnamyl | Cl | H | H | H |
| I-373 | 4-bromocinnamyl | Cl | H | H | H |
| I-374 | 4-trifluoromethylcinnamyl | Cl | H | H | H |
| I-375 | 4-trifluoromethoxycinnamyl | Cl | H | H | H |
| I-376 | 4-pentafluoroethoxycinnamyl | Cl | H | H | H |
| I-377 | 4-methoxycinnamyl | Cl | H | H | H |
| I-378 | 4-ethoxycinnamyl | Cl | H | H | H |
| I-379 | 4-cyanocinnamyl | Cl | H | H | H |
| I-380 | 3-(6-chloro-pyridin-3-yl)-allyl | Cl | H | H | H |
| I-381 | 3-(4-chlorophenyl)-but-2-enyl | Cl | H | H | H |
| I-382 | 3-(4-chlorophenyl)-3-fluoro-allyl | Cl | H | H | H |
| I-383 | 3-chloro-4-fluoro-cinnamyl | Cl | H | H | H |
| I-384 | 3,5-dichloro-cinnamyl | Cl | H | H | H |
| I-385 | 5-phenyl-penta-2,4-dienyl | Cl | H | H | H |
| I-386 | 4-isopropyloxycarbonylamino-cinnamyl | Cl | H | H | H |
| I-387 | 3-naphthalen-2-yl-allyl | Cl | H | H | H |
| I-388 | 3-(5-trifluoromethyl-pyridin-2-yl)-allyl | Cl | H | H | H |
| I-389 | 3-(5-chloro-pyridin-2-yl)-allyl | Cl | H | H | H |
| I-390 | 3-pyridin-4-yl-allyl | Cl | H | H | H |
| I-391 | 3-(2-Chloro-pyridin-4-yl)-allyl | Cl | H | H | H |
| I-392 | 4-chlorobenzyl | Br | H | H | H |
| I-393 | Cinnamyl | Br | H | H | H |
| I-394 | 4-chlorocinnamyl | Br | H | H | H |
| I-395 | 4-fluorocinnamyl | Br | H | H | H |
| I-396 | 4-bromocinnamyl | Br | H | H | H |
| I-397 | 4-trifluoromethylcinnamyl | Br | H | H | H |
| I-398 | 4-trifluoromethoxycinnamyl | Br | H | H | H |
| I-399 | 4-pentafluoroethoxycinnamyl | Br | H | H | H |
| I-400 | 4-methoxycinnamyl | Br | H | H | H |
| I-401 | 4-ethoxycinnamyl | Br | H | H | H |
| I-402 | 4-cyanocinnamyl | Br | H | H | H |
| I-403 | 3-(6-chloro-pyridin-3-yl)-allyl | Br | H | H | H |
| I-404 | 3-(4-chlorophenyl)-but-2-enyl | Br | H | H | H |
| I-405 | 3-(4-chlorophenyl)-3-fluoro-allyl | Br | H | H | H |
| I-406 | 3-chloro-4-fluoro-cinnamyl | Br | H | H | H |
| I-407 | 3,5-dichloro-cinnamyl | Br | H | H | H |
| I-408 | 5-phenyl-penta-2,4-dienyl | Br | H | H | H |
| I-409 | 4-isopropyloxycarbonylamino-cinnamyl | Br | H | H | H |
| I-410 | 3-naphthalen-2-yl-allyl | Br | H | H | H |
| I-411 | 3-(5-trifluoromethyl-pyridin-2-yl)-allyl | Br | H | H | H |
| I-412 | 3-(5-chloro-pyridin-2-yl)-allyl | Br | H | H | H |
| I-413 | 3-pyridin-4-yl-allyl | Br | H | H | H |
| I-414 | 3-(2-Chloro-pyridin-4-yl)-allyl | Br | H | H | H |
| I-415 | 4-chlorobenzyl | $CF_3$ | H | H | H |
| I-416 | Cinnamyl | $CF_3$ | H | H | H |
| I-417 | 4-chlorocinnamyl | $CF_3$ | H | H | H |
| I-418 | 4-fluorocinnamyl | $CF_3$ | H | H | H |
| I-419 | 4-bromocinnamyl | $CF_3$ | H | H | H |
| I-420 | 4-trifluoromethylcinnamyl | $CF_3$ | H | H | H |
| I-421 | 4-trifluoromethoxycinnamyl | $CF_3$ | H | H | H |
| I-422 | 4-pentafluoroethoxycinnamyl | $CF_3$ | H | H | H |
| I-423 | 4-methoxycinnamyl | $CF_3$ | H | H | H |
| I-424 | 4-ethoxycinnamyl | $CF_3$ | H | H | H |
| I-425 | 4-cyanocinnamyl | $CF_3$ | H | H | H |
| I-426 | 3-(6-chloro-pyridin-3-yl)-allyl | $CF_3$ | H | H | H |
| I-427 | 3-(4-chlorophenyl)-but-2-enyl | $CF_3$ | H | H | H |
| I-428 | 3-(4-chlorophenyl)-3-fluoro-allyl | $CF_3$ | H | H | H |
| I-429 | 3-chloro-4-fluoro-cinnamyl | $CF_3$ | H | H | H |
| I-430 | 3,5-dichloro-cinnamyl | $CF_3$ | H | H | H |
| I-431 | 5-phenyl-penta-2,4-dienyl | $CF_3$ | H | H | H |
| I-432 | 4-isopropyloxycarbonylamino-cinnamyl | $CF_3$ | H | H | H |
| I-433 | 3-naphthalen-2-yl-allyl | $CF_3$ | H | H | H |
| I-434 | 3-(5-trifluoromethyl-pyridin-2-yl)-allyl | $CF_3$ | H | H | H |
| I-435 | 3-(5-chloro-pyridin-2-yl)-allyl | $CF_3$ | H | H | H |
| I-436 | 3-pyridin-4-yl-allyl | $CF_3$ | H | H | H |

TABLE 1-continued

| Compound No | R⁸ | R⁴ᵃ | R⁴ᵇ | R⁴ᶜ | R⁴ᵈ |
|---|---|---|---|---|---|
| I-437 | 3-(2-Chloro-pyridin-4-yl)-allyl | CF₃ | H | H | H |
| I-438 | 4-chlorobenzyl | H | H | H | F |
| I-439 | Cinnamyl | H | H | H | F |
| I-440 | 4-chlorocinnamyl | H | H | H | F |
| I-441 | 4-fluorocinnamyl | H | H | H | F |
| I-442 | 4-bromocinnamyl | H | H | H | F |
| I-443 | 4-trifluoromethylcinnamyl | H | H | H | F |
| I-444 | 4-trifluoromethoxycinnamyl | H | H | H | F |
| I-445 | 4-pentafluoroethoxycinnamyl | H | H | H | F |
| I-446 | 4-methoxycinnamyl | H | H | H | F |
| I-447 | 4-ethoxycinnamyl | H | H | H | F |
| I-448 | 4-cyanocinnamyl | H | H | H | F |
| I-449 | 3-(6-chloro-pyridin-3-yl)-allyl | H | H | H | F |
| I-450 | 3-(4-chlorophenyl)-but-2-enyl | H | H | H | F |
| I-451 | 3-(4-chlorophenyl)-3-fluoro-allyl | H | H | H | F |
| I-452 | 3-chloro-4-fluoro-cinnamyl | H | H | H | F |
| I-453 | 3,5-dichloro-cinnamyl | H | H | H | F |
| I-454 | 5-phenyl-penta-2,4-dienyl | H | H | H | F |
| I-455 | 4-isopropyloxycarbonylamino-cinnamyl | H | H | H | F |
| I-456 | 3-naphthalen-2-yl-allyl | H | H | H | F |
| I-457 | 3-(5-trifluoromethyl-pyridin-2-yl)-allyl | H | H | H | F |
| I-458 | 3-(5-chloro-pyridin-2-yl)-allyl | H | H | H | F |
| I-459 | 3-pyridin-4-yl-allyl | H | H | H | F |
| I-460 | 3-(2-Chloro-pyridin-4-yl)-allyl | H | H | H | F |
| I-461 | 4-chlorobenzyl | H | H | H | Cl |
| I-462 | Cinnamyl | H | H | H | Cl |
| I-463 | 4-chlorocinnamyl | H | H | H | Cl |
| I-464 | 4-fluorocinnamyl | H | H | H | Cl |
| I-465 | 4-bromocinnamyl | H | H | H | Cl |
| I-466 | 4-trifluoromethylcinnamyl | H | H | H | Cl |
| I-467 | 4-trifluoromethoxycinnamyl | H | H | H | Cl |
| I-468 | 4-pentafluoroethoxycinnamyl | H | H | H | Cl |
| I-469 | 4-methoxycinnamyl | H | H | H | Cl |
| I-470 | 4-ethoxycinnamyl | H | H | H | Cl |
| I-471 | 4-cyanocinnamyl | H | H | H | Cl |
| I-472 | 3-(6-chloro-pyridin-3-yl)-allyl | H | H | H | Cl |
| I-473 | 3-(4-chlorophenyl)-but-2-enyl | H | H | H | Cl |
| I-474 | 3-(4-chlorophenyl)-3-fluoro-allyl | H | H | H | Cl |
| I-475 | 3-chloro-4-fluoro-cinnamyl | H | H | H | Cl |
| I-476 | 3,5-dichloro-cinnamyl | H | H | H | Cl |
| I-477 | 5-phenyl-penta-2,4-dienyl | H | H | H | Cl |
| I-478 | 4-isopropyloxycarbonylamino-cinnamyl | H | H | H | Cl |
| I-479 | 3-naphthalen-2-yl-allyl | H | H | H | Cl |
| I-480 | 3-(5-trifluoromethyl-pyridin-2-yl)-allyl | H | H | H | Cl |
| I-481 | 3-(5-chloro-pyridin-2-yl)-allyl | H | H | H | Cl |
| I-482 | 3-pyridin-4-yl-allyl | H | H | H | Cl |
| I-483 | 3-(2-Chloro-pyridin-4-yl)-allyl | H | H | H | Cl |
| I-484 | 4-chlorobenzyl | H | F | F | H |
| I-485 | Cinnamyl | H | F | F | H |
| I-486 | 4-chlorocinnamyl | H | F | F | H |
| I-487 | 4-fluorocinnamyl | H | F | F | H |
| I-488 | 4-bromocinnamyl | H | F | F | H |
| I-489 | 4-trifluoromethylcinnamyl | H | F | F | H |
| I-490 | 4-trifluoromethoxycinnamyl | H | F | F | H |
| I-491 | 4-pentafluoroethoxycinnamyl | H | F | F | H |
| I-492 | 4-methoxycinnamyl | H | F | F | H |
| I-493 | 4-ethoxycinnamyl | H | F | F | H |
| I-494 | 4-cyanocinnamyl | H | F | F | H |
| I-495 | 3-(6-chloro-pyridin-3-yl)-allyl | H | F | F | H |
| I-496 | 3-(4-chlorophenyl)-but-2-enyl | H | F | F | H |
| I-497 | 3-(4-chlorophenyl)-3-fluoro-allyl | H | F | F | H |
| I-498 | 3-chloro-4-fluoro-cinnamyl | H | F | F | H |
| I-499 | 3,5-dichloro-cinnamyl | H | F | F | H |
| I-500 | 5-phenyl-penta-2,4-dienyl | H | F | F | H |
| I-501 | 4-isopropyloxycarbonylamino-cinnamyl | H | F | F | H |
| I-502 | 3-naphthalen-2-yl-allyl | H | F | F | H |
| I-503 | 3-(5-trifluoromethyl-pyridin-2-yl)-allyl | H | F | F | H |
| I-504 | 3-(5-chloro-pyridin-2-yl)-allyl | H | F | F | H |
| I-505 | 3-pyridin-4-yl-allyl | H | F | F | H |
| I-506 | 3-(2-Chloro-pyridin-4-yl)-allyl | H | F | F | H |
| I-507 | 4-chlorobenzyl | H | F | Cl | H |
| I-508 | Cinnamyl | H | F | Cl | H |
| I-509 | 4-chlorocinnamyl | H | F | Cl | H |
| I-510 | 4-fluorocinnamyl | H | F | Cl | H |
| I-511 | 4-bromocinnamyl | H | F | Cl | H |
| I-512 | 4-trifluoromethylcinnamyl | H | F | Cl | H |
| I-513 | 4-trifluoromethoxycinnamyl | H | F | Cl | H |
| I-514 | 4-pentafluoroethoxycinnamyl | H | F | Cl | H |

TABLE 1-continued

| Compound No | R⁸ | R^{4a} | R^{4b} | R^{4c} | R^{4d} |
|---|---|---|---|---|---|
| I-515 | 4-methoxycinnamyl | H | F | Cl | H |
| I-516 | 4-ethoxycinnamyl | H | F | Cl | H |
| I-517 | 4-cyanocinnamyl | H | F | Cl | H |
| I-518 | 3-(6-chloro-pyridin-3-yl)-allyl | H | F | Cl | H |
| I-519 | 3-(4-chlorophenyl)-but-2-enyl | H | F | Cl | H |
| I-520 | 3-(4-chlorophenyl)-3-fluoro-allyl | H | F | Cl | H |
| I-521 | 3-chloro-4-fluoro-cinnamyl | H | F | Cl | H |
| I-522 | 3,5-dichloro-cinnamyl | H | F | Cl | H |
| I-523 | 5-phenyl-penta-2,4-dienyl | H | F | Cl | H |
| I-524 | 4-isopropyloxycarbonylamino-cinnamyl | H | F | Cl | H |
| I-525 | 3-naphthalen-2-yl-allyl | H | F | Cl | H |
| I-526 | 3-(5-trifluoromethyl-pyridin-2-yl)-allyl | H | F | Cl | H |
| I-527 | 3-(5-chloro-pyridin-2-yl)-allyl | H | F | Cl | H |
| I-528 | 3-pyridin-4-yl-allyl | H | F | Cl | H |
| I-529 | 3-(2-Chloro-pyridin-4-yl)-allyl | H | F | Cl | H |
| I-530 | 4-chlorobenzyl | H | Cl | F | H |
| I-531 | Cinnamyl | H | Cl | F | H |
| I-532 | 4-chlorocinnamyl | H | Cl | F | H |
| I-533 | 4-fluorocinnamyl | H | Cl | F | H |
| I-534 | 4-bromocinnamyl | H | Cl | F | H |
| I-535 | 4-trifluoromethylcinnamyl | H | Cl | F | H |
| I-536 | 4-trifluoromethoxycinnamyl | H | Cl | F | H |
| I-537 | 4-pentafluoroethoxycinnamyl | H | Cl | F | H |
| I-538 | 4-methoxycinnamyl | H | Cl | F | H |
| I-539 | 4-ethoxycinnamyl | H | Cl | F | H |
| I-540 | 4-cyanocinnamyl | H | Cl | F | H |
| I-541 | 3-(6-chloro-pyridin-3-yl)-allyl | H | Cl | F | H |
| I-542 | 3-(4-chlorophenyl)-but-2-enyl | H | Cl | F | H |
| I-543 | 3-(4-chlorophenyl)-3-fluoro-allyl | H | Cl | F | H |
| I-544 | 3-chloro-4-fluoro-cinnamyl | H | Cl | F | H |
| I-545 | 3,5-dichloro-cinnamyl | H | Cl | F | H |
| I-546 | 5-phenyl-penta-2,4-dienyl | H | Cl | F | H |
| I-547 | 4-isopropyloxycarbonylamino-cinnamyl | H | Cl | F | H |
| I-548 | 3-naphthalen-2-yl-allyl | H | Cl | F | H |
| I-549 | 3-(5-trifluoromethyl-pyridin-2-yl)-allyl | H | Cl | F | H |
| I-550 | 3-(5-chloro-pyridin-2-yl)-allyl | H | Cl | F | H |
| I-551 | 3-pyridin-4-yl-allyl | H | Cl | F | H |
| I-552 | 3-(2-Chloro-pyridin-4-yl)-allyl | H | Cl | F | H |
| I-553 | 4-chlorobenzyl | H | Cl | Cl | H |
| I-554 | Cinnamyl | H | Cl | Cl | H |
| I-555 | 4-chlorocinnamyl | H | Cl | Cl | H |
| I-556 | 4-fluorocinnamyl | H | Cl | Cl | H |
| I-557 | 4-bromocinnamyl | H | Cl | Cl | H |
| I-558 | 4-trifluoromethylcinnamyl | H | Cl | Cl | H |
| I-559 | 4-trifluoromethoxycinnamyl | H | Cl | Cl | H |
| I-560 | 4-pentafluoroethoxycinnamyl | H | Cl | Cl | H |
| I-561 | 4-methoxycinnamyl | H | Cl | Cl | H |
| I-562 | 4-ethoxycinnamyl | H | Cl | Cl | H |
| I-563 | 4-cyanocinnamyl | H | Cl | Cl | H |
| I-564 | 3-(6-chloro-pyridin-3-yl)-allyl | H | Cl | Cl | H |
| I-565 | 3-(4-chlorophenyl)-but-2-enyl | H | Cl | Cl | H |
| I-566 | 3-(4-chlorophenyl)-3-fluoro-allyl | H | Cl | Cl | H |
| I-567 | 3-chloro-4-fluoro-cinnamyl | H | Cl | Cl | H |
| I-568 | 3,5-dichloro-cinnamyl | H | Cl | Cl | H |
| I-569 | 5-phenyl-penta-2,4-dienyl | H | Cl | Cl | H |
| I-570 | 4-isopropyloxycarbonylamino-cinnamyl | H | Cl | Cl | H |
| I-571 | 3-naphthalen-2-yl-allyl | H | Cl | Cl | H |
| I-572 | 3-(5-trifluoromethyl-pyridin-2-yl)-allyl | H | Cl | Cl | H |
| I-573 | 3-(5-chloro-pyridin-2-yl)-allyl | H | Cl | Cl | H |
| I-574 | 3-pyridin-4-yl-allyl | H | Cl | Cl | H |
| I-575 | 3-(2-Chloro-pyridin-4-yl)-allyl | H | Cl | Cl | H |
| I-576 | 4-chlorobenzyl | H | —OCF₂O— | | H |
| I-577 | Cinnamyl | H | —OCF₂O— | | H |
| I-578 | 4-chlorocinnamyl | H | —OCF₂O— | | H |
| I-579 | 4-fluorocinnamyl | H | —OCF₂O— | | H |
| I-580 | 4-bromocinnamyl | H | —OCF₂O— | | H |
| I-581 | 4-trifluoromethylcinnamyl | H | —OCF₂O— | | H |
| I-582 | 4-trifluoromethoxycinnamyl | H | —OCF₂O— | | H |
| I-583 | 4-pentafluoroethoxycinnamyl | H | —OCF₂O— | | H |
| I-584 | 4-methoxycinnamyl | H | —OCF₂O— | | H |
| I-585 | 4-ethoxycinnamyl | H | —OCF₂O— | | H |
| I-586 | 4-cyanocinnamyl | H | —OCF₂O— | | H |
| I-587 | 3-(6-chloro-pyridin-3-yl)-allyl | H | —OCF₂O— | | H |
| I-588 | 3-(4-chlorophenyl)-but-2-enyl | H | —OCF₂O— | | H |
| I-589 | 3-(4-chlorophenyl)-3-fluoro-allyl | H | —OCF₂O— | | H |
| I-590 | 3-chloro-4-fluoro-cinnamyl | H | —OCF₂O— | | H |
| I-591 | 3,5-dichloro-cinnamyl | H | —OCF₂O— | | H |
| I-592 | 5-phenyl-penta-2,4-dienyl | H | —OCF₂O— | | H |

TABLE 1-continued

| Compound No | R⁸ | R⁴ᵃ | R⁴ᵇ | R⁴ᶜ | R⁴ᵈ |
|---|---|---|---|---|---|
| I-593 | 4-isopropyloxycarbonylamino-cinnamyl | H | —OCF₂O— | | H |
| I-594 | 3-naphthalen-2-yl-allyl | H | —OCF₂O— | | H |
| I-595 | 3-(5-trifluoromethyl-pyridin-2-yl)-allyl | H | —OCF₂O— | | H |
| I-596 | 3-(5-chloro-pyridin-2-yl)-allyl | H | —OCF₂O— | | H |
| I-597 | 3-pyridin-4-yl-allyl | H | —OCF₂O— | | H |
| I-598 | 3-(2-Chloro-pyridin-4-yl)-allyl | H | —OCF₂O— | | H |
| I-599 | 4-chlorobenzyl | H | —C₄H₄— | | H |
| I-600 | Cinnamyl | H | —C₄H₄— | | H |
| I-601 | 4-chlorocinnamyl | H | —C₄H₄— | | H |
| I-602 | 4-fluorocinnamyl | H | —C₄H₄— | | H |
| I-603 | 4-bromocinnamyl | H | —C₄H₄— | | H |
| I-604 | 4-trifluoromethylcinnamyl | H | —C₄H₄— | | H |
| I-605 | 4-trifluoromethoxycinnamyl | H | —C₄H₄— | | H |
| I-606 | 4-pentafluoroethoxycinnamyl | H | —C₄H₄— | | H |
| I-607 | 4-methoxycinnamyl | H | —C₄H₄— | | H |
| I-608 | 4-ethoxycinnamyl | H | —C₄H₄— | | H |
| I-609 | 4-cyanocinnamyl | H | —C₄H₄— | | H |
| I-610 | 3-(6-chloro-pyridin-3-yl)-allyl | H | —C₄H₄— | | H |
| I-611 | 3-(4-chlorophenyl)-but-2-enyl | H | —C₄H₄— | | H |
| I-612 | 3-(4-chlorophenyl)-3-fluoro-allyl | H | —C₄H₄— | | H |
| I-613 | 3-chloro-4-fluoro-cinnamyl | H | —C₄H₄— | | H |
| I-614 | 3,5-dichloro-cinnamyl | H | —C₄H₄— | | H |
| I-615 | 5-phenyl-penta-2,4-dienyl | H | —C₄H₄— | | H |
| I-616 | 4-isopropyloxycarbonylamino-cinnamyl | H | —C₄H₄— | | H |
| I-617 | 3-naphthalen-2-yl-allyl | H | —C₄H₄— | | H |
| I-618 | 3-(5-trifluoromethyl-pyridin-2-yl)-allyl | H | —C₄H₄— | | H |
| I-619 | 3-(5-chloro-pyridin-2-yl)-allyl | H | —C₄H₄— | | H |
| I-620 | 3-pyridin-4-yl-allyl | H | —C₄H₄— | | H |
| I-621 | 3-(2-Chloro-pyridin-4-yl)-allyl | H | —C₄H₄— | | H |
| I-622 | 4-chlorobenzyl | Cl | H | Cl | H |
| I-623 | Cinnamyl | Cl | H | Cl | H |
| I-624 | 4-chlorocinnamyl | Cl | H | Cl | H |
| I-625 | 4-fluorocinnamyl | Cl | H | Cl | H |
| I-626 | 4-bromocinnamyl | Cl | H | Cl | H |
| I-627 | 4-trifluoromethylcinnamyl | Cl | H | Cl | H |
| I-628 | 4-trifluoromethoxycinnamyl | Cl | H | Cl | H |
| I-629 | 4-pentafluoroethoxycinnamyl | Cl | H | Cl | H |
| I-630 | 4-methoxycinnamyl | Cl | H | Cl | H |
| I-631 | 4-ethoxycinnamyl | Cl | H | Cl | H |
| I-632 | 4-cyanocinnamyl | Cl | H | Cl | H |
| I-633 | 3-(6-chloro-pyridin-3-yl)-allyl | Cl | H | Cl | H |
| I-634 | 3-(4-chlorophenyl)-but-2-enyl | Cl | H | Cl | H |
| I-635 | 3-(4-chlorophenyl)-3-fluoro-allyl | Cl | H | Cl | H |
| I-636 | 3-chloro-4-fluoro-cinnamyl | Cl | H | Cl | H |
| I-637 | 3,5-dichloro-cinnamyl | Cl | H | Cl | H |
| I-638 | 5-phenyl-penta-2,4-dienyl | Cl | H | Cl | H |
| I-639 | 4-isopropyloxycarbonylamino-cinnamyl | Cl | H | Cl | H |
| I-640 | 3-naphthalen-2-yl-allyl | Cl | H | Cl | H |
| I-641 | 3-(5-trifluoromethyl-pyridin-2-yl)-allyl | Cl | H | Cl | H |
| I-642 | 3-(5-chloro-pyridin-2-yl)-allyl | Cl | H | Cl | H |
| I-643 | 3-pyridin-4-yl-allyl | Cl | H | Cl | H |
| I-644 | 3-(2-Chloro-pyridin-4-yl)-allyl | Cl | H | Cl | H |
| I-645 | 4-chlorobenzyl | Cl | Cl | H | H |
| I-646 | Cinnamyl | Cl | Cl | H | H |
| I-647 | 4-chlorocinnamyl | Cl | Cl | H | H |
| I-648 | 4-fluorocinnamyl | Cl | Cl | H | H |
| I-649 | 4-bromocinnamyl | Cl | Cl | H | H |
| I-650 | 4-trifluoromethylcinnamyl | Cl | Cl | H | H |
| I-651 | 4-trifluoromethoxycinnamyl | Cl | Cl | H | H |
| I-652 | 4-pentafluoroethoxycinnamyl | Cl | Cl | H | H |
| I-653 | 4-methoxycinnamyl | Cl | Cl | H | H |
| I-654 | 4-ethoxycinnamyl | Cl | Cl | H | H |
| I-655 | 4-cyanocinnamyl | Cl | Cl | H | H |
| I-656 | 3-(6-chloro-pyridin-3-yl)-allyl | Cl | Cl | H | H |
| I-657 | 3-(4-chlorophenyl)-but-2-enyl | Cl | Cl | H | H |
| I-658 | 3-(4-chlorophenyl)-3-fluoro-allyl | Cl | Cl | H | H |
| I-659 | 3-chloro-4-fluoro-cinnamyl | Cl | Cl | H | H |
| I-660 | 3,5-dichloro-cinnamyl | Cl | Cl | H | H |
| I-661 | 5-phenyl-penta-2,4-dienyl | Cl | Cl | H | H |
| I-662 | 4-isopropyloxycarbonylamino-cinnamyl | Cl | Cl | H | H |
| I-663 | 3-naphthalen-2-yl-allyl | Cl | Cl | H | H |
| I-664 | 3-(5-trifluoromethyl-pyridin-2-yl)-allyl | Cl | Cl | H | H |
| I-665 | 3-(5-chloro-pyridin-2-yl)-allyl | Cl | Cl | H | H |
| I-666 | 3-pyridin-4-yl-allyl | Cl | Cl | H | H |
| I-667 | 3-(2-Chloro-pyridin-4-yl)-allyl | Cl | Cl | H | H |
| I-668 | 4-chlorobenzyl | H | Cl | H | Cl |
| I-669 | Cinnamyl | H | Cl | H | Cl |
| I-670 | 4-chlorocinnamyl | H | Cl | H | Cl |

TABLE 1-continued

| Compound No | $R^8$ | $R^{4a}$ | $R^{4b}$ | $R^{4c}$ | $R^{4d}$ |
|---|---|---|---|---|---|
| I-671 | 4-fluorocinnamyl | H | Cl | H | Cl |
| I-672 | 4-bromocinnamyl | H | Cl | H | Cl |
| I-673 | 4-trifluoromethylcinnamyl | H | Cl | H | Cl |
| I-674 | 4-trifluoromethoxycinnamyl | H | Cl | H | Cl |
| I-675 | 4-pentafluoroethoxycinnamyl | H | Cl | H | Cl |
| I-676 | 4-methoxycinnamyl | H | Cl | H | Cl |
| I-677 | 4-ethoxycinnamyl | H | Cl | H | Cl |
| I-678 | 4-cyanocinnamyl | H | Cl | H | Cl |
| I-679 | 3-(6-chloro-pyridin-3-yl)-allyl | H | Cl | H | Cl |
| I-680 | 3-(4-chlorophenyl)-but-2-enyl | H | Cl | H | Cl |
| I-681 | 3-(4-chlorophenyl)-3-fluoro-allyl | H | Cl | H | Cl |
| I-682 | 3-chloro-4-fluoro-cinnamyl | H | Cl | H | Cl |
| I-683 | 3,5-dichloro-cinnamyl | H | Cl | H | Cl |
| I-684 | 5-phenyl-penta-2,4-dienyl | H | Cl | H | Cl |
| I-685 | 4-isopropyloxycarbonylamino-cinnamyl | H | Cl | H | Cl |
| I-686 | 3-naphthalen-2-yl-allyl | H | Cl | H | Cl |
| I-687 | 3-(5-trifluoromethyl-pyridin-2-yl)-allyl | H | Cl | H | Cl |
| I-688 | 3-(5-chloro-pyridin-2-yl)-allyl | H | Cl | H | Cl |
| I-689 | 3-pyridin-4-yl-allyl | H | Cl | H | Cl |
| I-690 | 3-(2-Chloro-pyridin-4-yl)-allyl | H | Cl | H | Cl |
| I-691 | 4-chlorobenzyl | H | F | H | F |
| I-692 | Cinnamyl | H | F | H | F |
| I-693 | 4-chlorocinnamyl | H | F | H | F |
| I-694 | 4-fluorocinnamyl | H | F | H | F |
| I-695 | 4-bromocinnamyl | H | F | H | F |
| I-696 | 4-trifluoromethylcinnamyl | H | F | H | F |
| I-697 | 4-trifluoromethoxycinnamyl | H | F | H | F |
| I-698 | 4-pentafluoroethoxycinnamyl | H | F | H | F |
| I-699 | 4-methoxycinnamyl | H | F | H | F |
| I-700 | 4-ethoxycinnamyl | H | F | H | F |
| I-701 | 4-cyanocinnamyl | H | F | H | F |
| I-702 | 3-(6-chloro-pyridin-3-yl)-allyl | H | F | H | F |
| I-703 | 3-(4-chlorophenyl)-but-2-enyl | H | F | H | F |
| I-704 | 3-(4-chlorophenyl)-3-fluoro-allyl | H | F | H | F |
| I-705 | 3-chloro-4-fluoro-cinnamyl | H | F | H | F |
| I-706 | 3,5-dichloro-cinnamyl | H | F | H | F |
| I-707 | 5-phenyl-penta-2,4-dienyl | H | F | H | F |
| I-708 | 4-isopropyloxycarbonylamino-cinnamyl | H | F | H | F |
| I-709 | 3-naphthalen-2-yl-allyl | H | F | H | F |
| I-710 | 3-(5-trifluoromethyl-pyridin-2-yl)-allyl | H | F | H | F |
| I-711 | 3-(5-chloro-pyridin-2-yl)-allyl | H | F | H | F |
| I-712 | 3-pyridin-4-yl-allyl | H | F | H | F |
| I-713 | 3-(2-Chloro-pyridin-4-yl)-allyl | H | F | H | F |
| I-714 | 4-chlorobenzyl | F | H | F | H |
| I-715 | Cinnamyl | F | H | F | H |
| I-716 | 4-chlorocinnamyl | F | H | F | H |
| I-717 | 4-fluorocinnamyl | F | H | F | H |
| I-718 | 4-bromocinnamyl | F | H | F | H |
| I-719 | 4-trifluoromethylcinnamyl | F | H | F | H |
| I-720 | 4-trifluoromethoxycinnamyl | F | H | F | H |
| I-721 | 4-pentafluoroethoxycinnamyl | F | H | F | H |
| I-722 | 4-methoxycinnamyl | F | H | F | H |
| I-723 | 4-ethoxycinnamyl | F | H | F | H |
| I-724 | 4-cyanocinnamyl | F | H | F | H |
| I-725 | 3-(6-chloro-pyridin-3-yl)-allyl | F | H | F | H |
| I-726 | 3-(4-chlorophenyl)-but-2-enyl | F | H | F | H |
| I-727 | 3-(4-chlorophenyl)-3-fluoro-allyl | F | H | F | H |
| I-728 | 3-chloro-4-fluoro-cinnamyl | F | H | F | H |
| I-729 | 3,5-dichloro-cinnamyl | F | H | F | H |
| I-730 | 5-phenyl-penta-2,4-dienyl | F | H | F | H |
| I-731 | 4-isopropyloxycarbonylamino-cinnamyl | F | H | F | H |
| I-732 | 3-naphthalen-2-yl-allyl | F | H | F | H |
| I-733 | 3-(5-trifluoromethyl-pyridin-2-yl)-allyl | F | H | F | H |
| I-734 | 3-(5-chloro-pyridin-2-yl)-allyl | F | H | F | H |
| I-735 | 3-pyridin-4-yl-allyl | F | H | F | H |
| I-736 | 3-(2-Chloro-pyridin-4-yl)-allyl | F | H | F | H |
| I-737 | 4-chlorobenzyl | F | F | H | H |
| I-738 | Cinnamyl | F | F | H | H |
| I-739 | 4-chlorocinnamyl | F | F | H | H |
| I-740 | 4-fluorocinnamyl | F | F | H | H |

TABLE 1-continued

| Compound No | R⁸ | R⁴ᵃ | R⁴ᵇ | R⁴ᶜ | R⁴ᵈ |
|---|---|---|---|---|---|
| I-741 | 4-bromocinnamyl | F | F | H | H |
| I-742 | 4-trifluoromethylcinnamyl | F | F | H | H |
| I-743 | 4-trifluoromethoxycinnamyl | F | F | H | H |
| I-744 | 4-pentafluoroethoxycinnamyl | F | F | H | H |
| I-745 | 4-methoxycinnamyl | F | F | H | H |
| I-746 | 4-ethoxycinnamyl | F | F | H | H |
| I-747 | 4-cyanocinnamyl | F | F | H | H |
| I-748 | 3-(6-chloro-pyridin-3-yl)-allyl | F | F | H | H |
| I-749 | 3-(4-chlorophenyl)-but-2-enyl | F | F | H | H |
| I-750 | 3-(4-chlorophenyl)-3-fluoro-allyl | F | F | H | H |
| I-751 | 3-chloro-4-fluoro-cinnamyl | F | F | H | H |
| I-752 | 3,5-dichloro-cinnamyl | F | F | H | H |
| I-753 | 5-phenyl-penta-2,4-dienyl | F | F | H | H |
| I-754 | 4-isopropyloxycarbonylamino-cinnamyl | F | F | H | H |
| I-755 | 3-naphthalen-2-yl-allyl | F | F | H | H |
| I-756 | 3-(5-trifluoromethyl-pyridin-2-yl)-allyl | F | F | H | H |
| I-757 | 3-(5-chloro-pyridin-2-yl)-allyl | F | F | H | H |
| I-758 | 3-pyridin-4-yl-allyl | F | F | H | H |
| I-759 | 3-(2-Chloro-pyridin-4-yl)-allyl | F | F | H | H |
| I-760 | 4-chlorobenzyl | Cl | F | H | H |
| I-761 | Cinnamyl | Cl | F | H | H |
| I-762 | 4-chlorocinnamyl | Cl | F | H | H |
| I-763 | 4-fluorocinnamyl | Cl | F | H | H |
| I-764 | 4-bromocinnamyl | Cl | F | H | H |
| I-765 | 4-trifluoromethylcinnamyl | Cl | F | H | H |
| I-766 | 4-trifluoromethoxycinnamyl | Cl | F | H | H |
| I-767 | 4-pentafluoroethoxycinnamyl | Cl | F | H | H |
| I-768 | 4-methoxycinnamyl | Cl | F | H | H |
| I-769 | 4-ethoxycinnamyl | Cl | F | H | H |
| I-770 | 4-cyanocinnamyl | Cl | F | H | H |
| I-771 | 3-(6-chloro-pyridin-3-yl)-allyl | Cl | F | H | H |
| I-772 | 3-(4-chlorophenyl)-but-2-enyl | Cl | F | H | H |
| I-773 | 3-(4-chlorophenyl)-3-fluoro-allyl | Cl | F | H | H |
| I-774 | 3-chloro-4-fluoro-cinnamyl | Cl | F | H | H |
| I-775 | 3,5-dichloro-cinnamyl | Cl | F | H | H |
| I-776 | 5-phenyl-penta-2,4-dienyl | Cl | F | H | H |
| I-777 | 4-isopropyloxycarbonylamino-cinnamyl | Cl | F | H | H |
| I-778 | 3-naphthalen-2-yl-allyl | Cl | F | H | H |
| I-779 | 3-(5-trifluoromethyl-pyridin-2-yl)-allyl | Cl | F | H | H |
| I-780 | 3-(5-chloro-pyridin-2-yl)-allyl | Cl | F | H | H |
| I-781 | 3-pyridin-4-yl-allyl | Cl | F | H | H |
| I-782 | 3-(2-Chloro-pyridin-4-yl)-allyl | Cl | F | H | H |

Table II provides 782 compounds of formula Ib

Table III provides 782 compounds of formula Ic

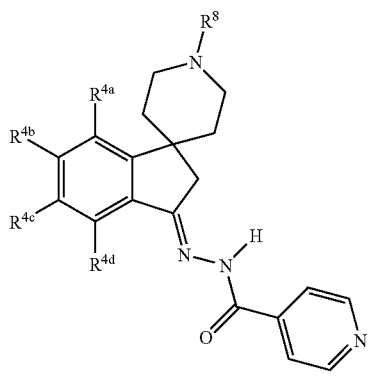

(1b)

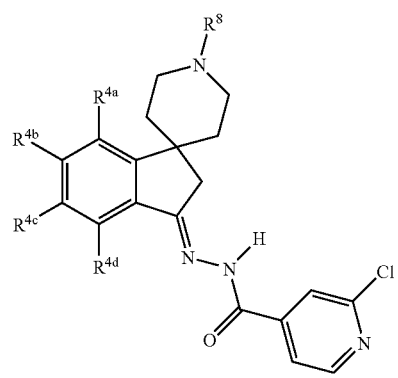

(Ic)

wherein the values of $R^8$, $R^{4a}$, $R^{4b}$, $R^{4c}$ and $R^{4d}$ are given in Table 1 wherein the values of $R^8$, $R^{4a}$, $R^{4b}$, $R^{4c}$ and $R^{4d}$ are given in Table 1

Table IV provides 782 compounds of formula Id

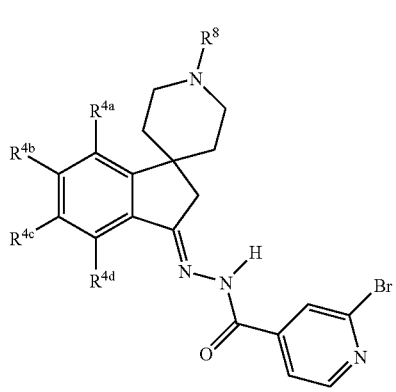

wherein the values of $R^8$, $R^{4a}$, $R^{4b}$, $R^{4c}$ and $R^{4d}$ are given in Table 1

Table V provides 782 compounds of formula Ie

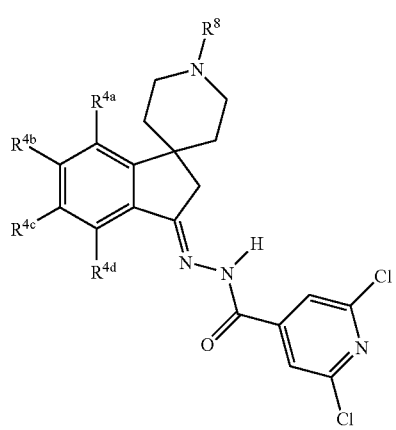

wherein the values of $R^8$, $R^{4a}$, $R^{4b}$, $R^{4c}$ and $R^{4d}$ are given in Table 1

Table VI provides 782 compounds of formula If

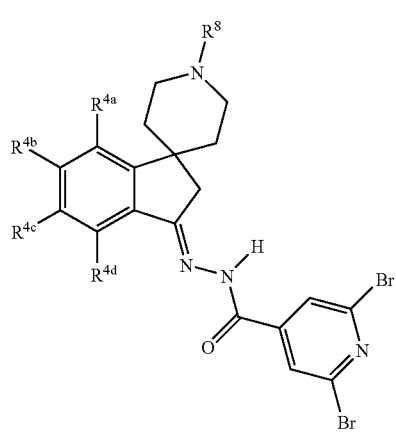

wherein the values of $R^8$, $R^{4a}$, $R^{4b}$, $R^{4c}$ and $R^{4d}$ are given in Table 1

Table VII provides 782 compounds of formula Ig

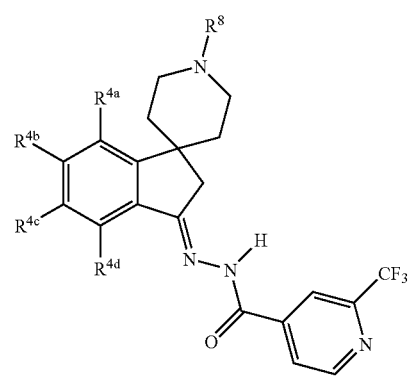

wherein the values of $R^8$, $R^{4a}$, $R^{4b}$, $R^{4c}$ and $R^{4d}$ are given in Table 1

Table VIII provides 782 compounds of formula Ih

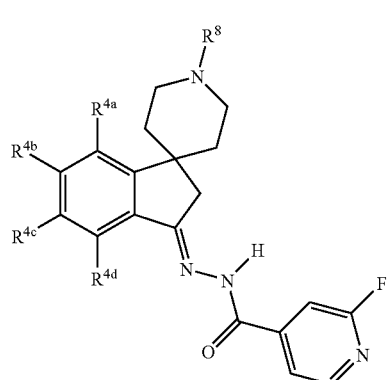

wherein the values of $R^8$, $R^{4a}$, $R^{4b}$, $R^{4c}$ and $R^{4d}$ are given in Table 1

Table IX provides 782 compounds of formula Ii

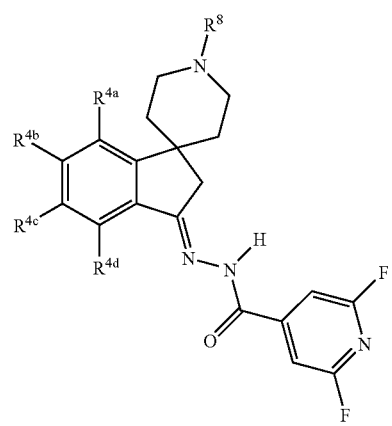

wherein the values of $R^8$, $R^{4a}$, $R^{4b}$, $R^{4c}$ and $R^{4d}$ are given in Table 1

Table X provides 782 compounds of formula Ij

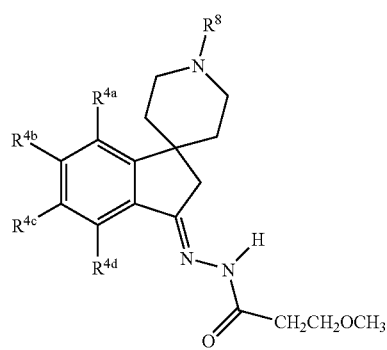

wherein the values of $R^8$, $R^{4a}$, $R^{4b}$, $R^{4c}$ and $R^{4d}$ are given in Table 1

Table XI provides 782 compounds of formula Ik

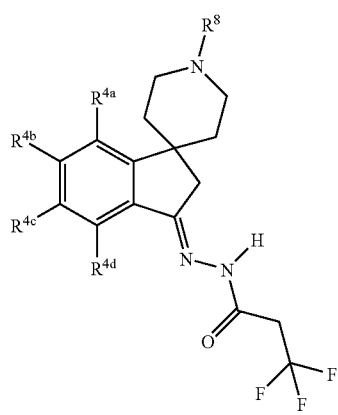

wherein the values of $R^8$, $R^{4a}$, $R^{4b}$, $R^{4c}$ and $R^{4d}$ are given in Table 1

Table XII provides 782 compounds of formula Il

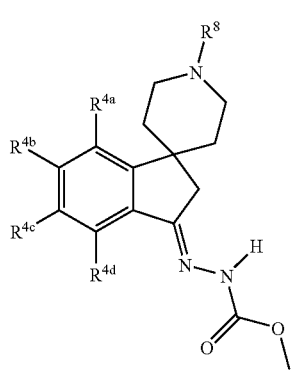

wherein the values of $R^8$, $R^{4a}$, $R^{4b}$, $R^{4c}$ and $R^{4d}$ are given in Table 1

Table XIII provides 782 compounds of formula Im

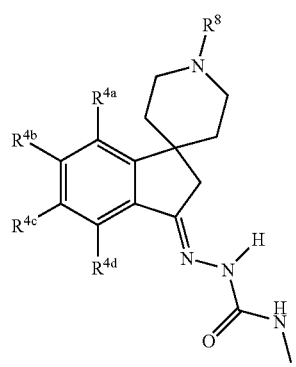

wherein the values of $R^8$, $R^{4a}$, $R^{4b}$, $R^{4c}$ and $R^{4d}$ are given in Table 1

Table XIV provides 782 compounds of formula In

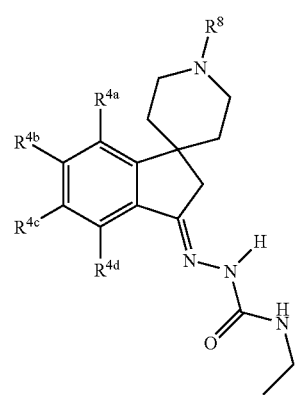

wherein the values of $R^8$, $R^{4a}$, $R^{4b}$, $R^{4c}$ and $R^{4d}$ are given in Table 1

Table XV provides 782 compounds of formula Io

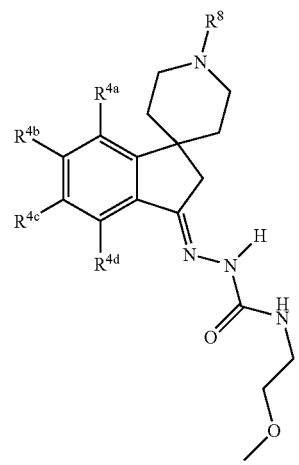

wherein the values of $R^8$, $R^{4a}$, $R^{4b}$, $R^{4c}$ and $R^{4d}$ are given in Table 1

Table XVI provides 782 compounds of formula Ip

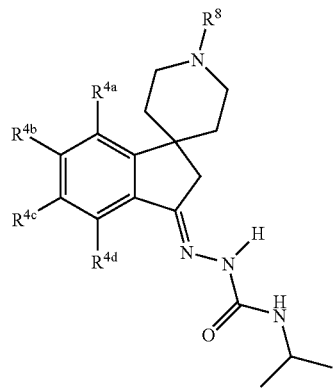

(Ip)

wherein the values of $R^8$, $R^{4a}$, $R^{4b}$, $R^{4c}$ and $R^{4d}$ are given in Table 1

Table XVII provides 782 compounds of formula Iq

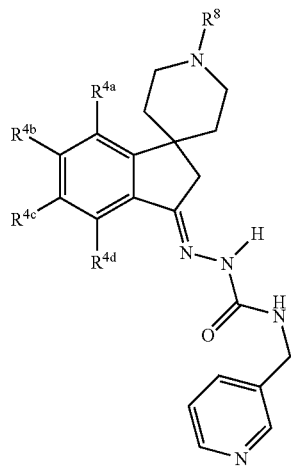

(Iq)

wherein the values of $R^1$, $R^{4a}$, $R^{1b}$, $R^{4c}$ and $R^{4d}$ are given in Table 1

Table XVIII provides 782 compounds of formula Ir

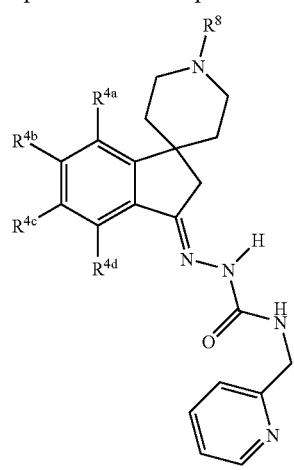

(Ir)

wherein the values of $R^1$, $R^{4a}$, $R^{4b}$, $R^{4c}$ and $R^{4d}$ are given in Table 1

Table XX provides 782 compounds of formula It

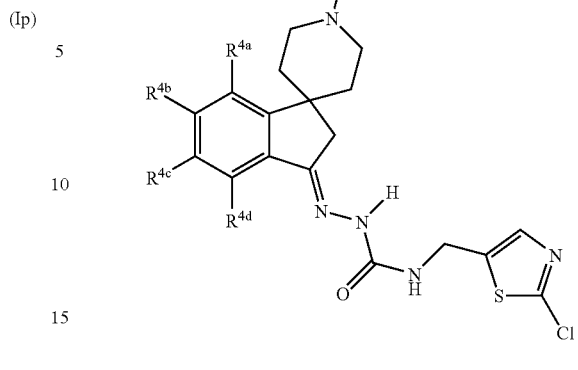

(It)

wherein the values of $R^8$, $R^{4a}$, $R^{4b}$, $R^{4c}$ and $R^{4d}$ are given in Table 1

Table XXI provides 782 compounds of formula Iu

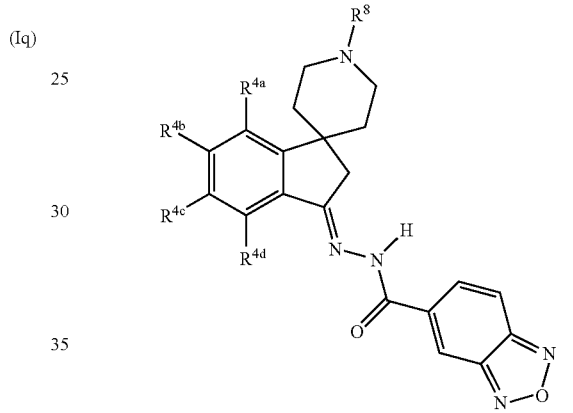

(Iu)

wherein the values of $R^8$, $R^{4a}$, $R^{4b}$, $R^{4c}$ and $R^{4d}$ are given in Table 1

Table XXII provides 782 compounds of formula Iv

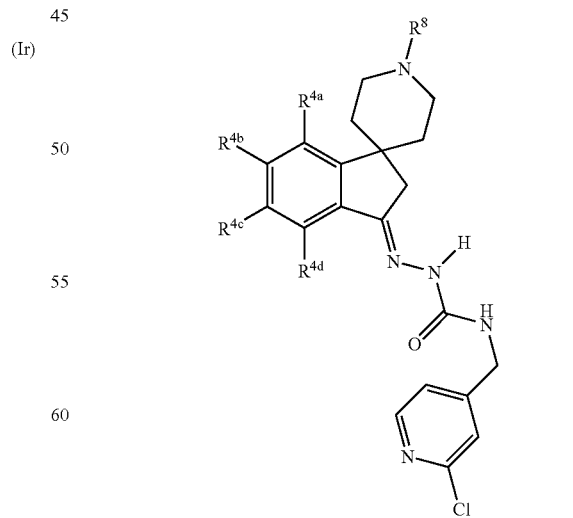

(Iv)

wherein the values of $R^8$, $R^{4a}$, $R^{4b}$, $R^{4c}$ and $R^{4d}$ are given in Table 1

Table XXIII provides 782 compounds of formula Iw

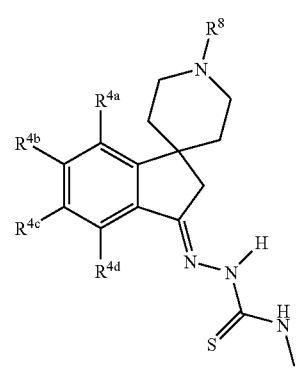

(Iw)

wherein the values of $R^1$, $R^{4a}$, $R^{4b}$, $R^{4c}$ and $R^{4d}$ are given in Table 1

Table XXIV provides 782 compounds of formula Ix

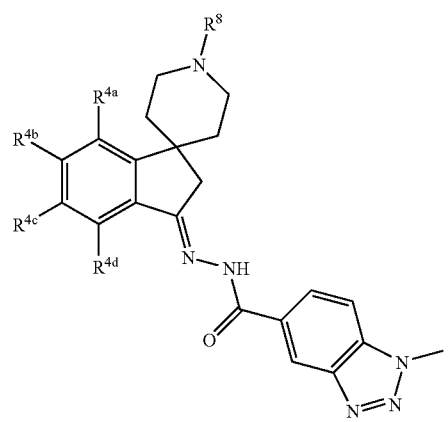

(Ix)

wherein the values of $R^8$, $R^{4a}$, $R^{4b}$, $R^{4c}$ and $R^{4d}$ are given in Table 1

Table XXV provides 782 compounds of formula Iy

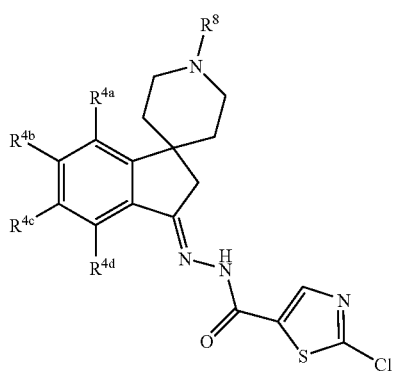

(Iy)

wherein the values of $R^8$, $R^{4a}$, $R^{4b}$, $R^{4c}$ and $R^{4d}$ are given in Table 1

Table XXVI provides 782 compounds of formula Iz

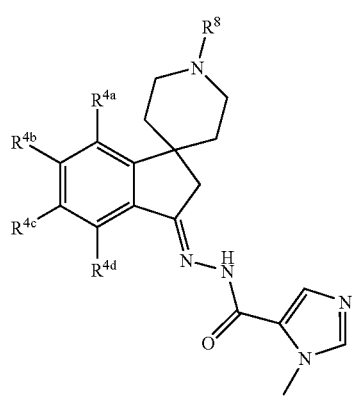

(Iz)

wherein the values of $R^8$, $R^{4a}$, $R^{4b}$, $R^{4c}$ and $R^{4d}$ are given in Table 1

Table XXVII provides 782 compounds of formula Iaa

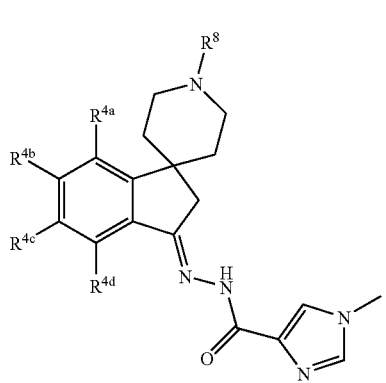

(Iaa)

wherein the values of $R^8$, $R^{4a}$, $R^{4b}$, $R^{4c}$ and $R^{4d}$ are given in Table 1

Table XXVIII provides 782 compounds of formula Iab

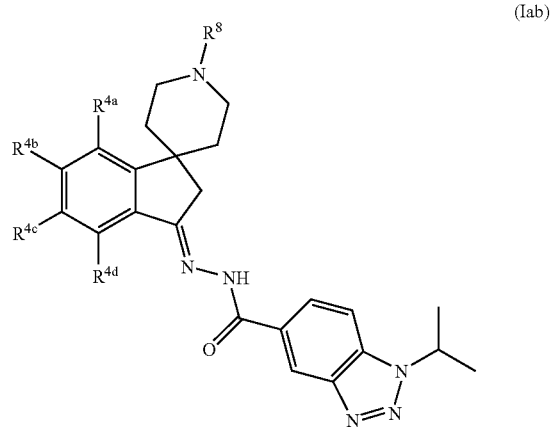

(Iab)

wherein the values of $R^8$, $R^{4a}$, $R^{4b}$, $R^{4c}$ and $R^{4d}$ are given in Table 1

Table XXIX provides 782 compounds of formula Iac

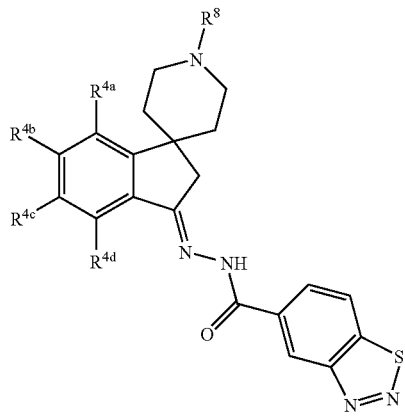

wherein the values of $R^8$, $R^{4a}$, $R^{4b}$, $R^{4c}$ and $R^{4d}$ are given in Table 1

Table XXX provides 782 compounds of formula Iad

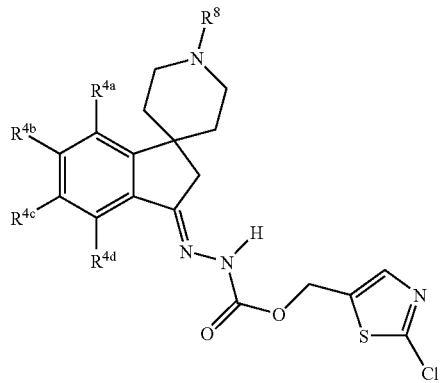

wherein the values of $R^8$, $R^{4a}$, $R^{4b}$, $R^{4c}$ and $R^{4d}$ are given in Table 1

Table XXXI provides 782 compounds of formula Iae

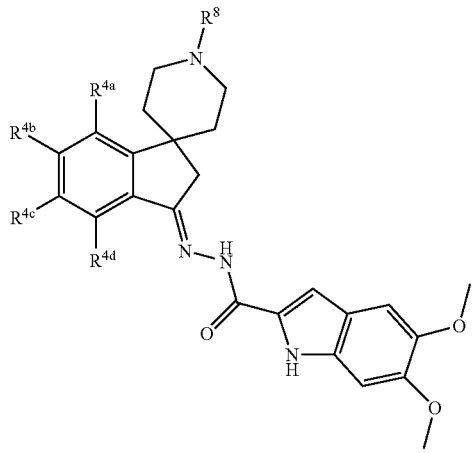

wherein the values of $R^8$, $R^{4a}$, $R^{4b}$, $R^{4c}$ and $R^{4d}$ are given in Table 1

Table XXXII provides 782 compounds of formula Iaf

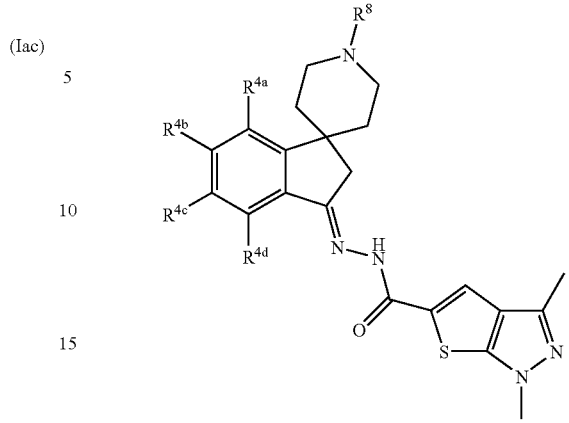

wherein the values of $R^8$, $R^{4a}$, $R^{4b}$, $R^{4c}$ and $R^{4d}$ are given in Table 1

Table XXXIV provides 782 compounds of formula Iah

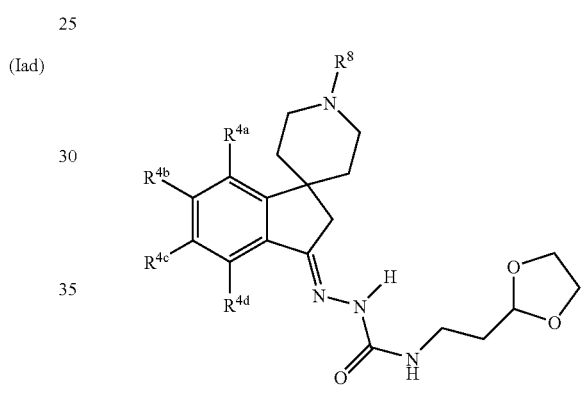

wherein the values of $R^8$, $R^{4a}$, $R^{4b}$, $R^{4c}$ and $R^{4d}$ are given in Table 1

Table XXXV provides 782 compounds of formula Iai

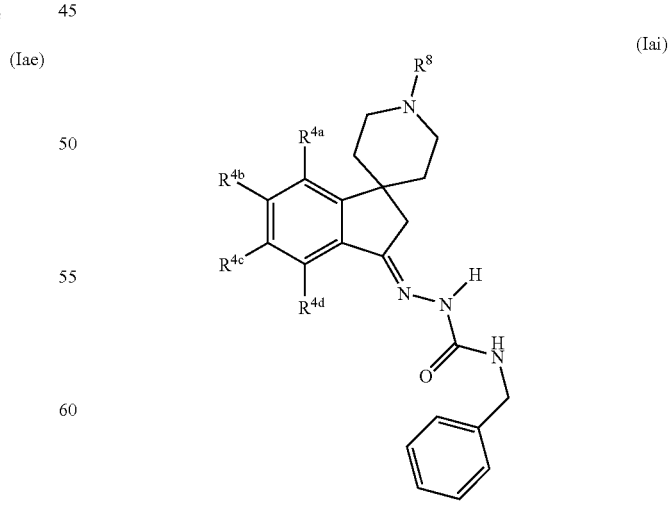

wherein the values of $R^8$, $R^{4a}$, $R^{4b}$, $R^{4c}$ and $R^{4d}$ are given in Table 1

Table XXXVI provides 782 compounds of formula Iaj

Table XXXIX provides 782 compounds of formula Iam

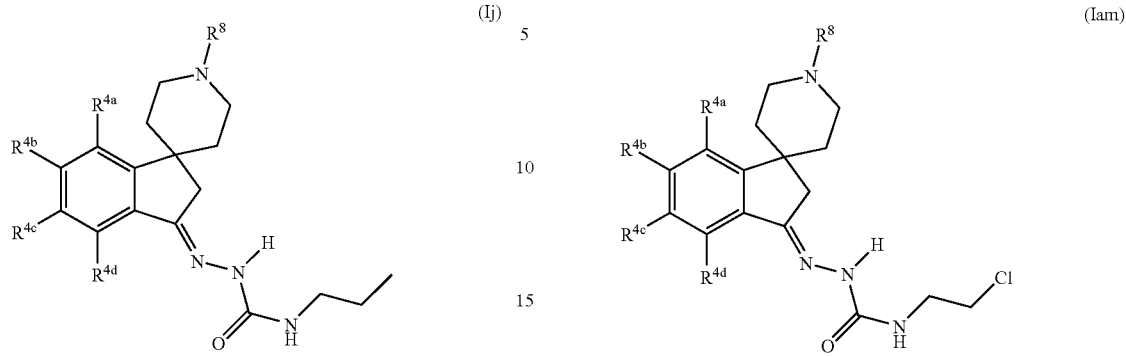

wherein the values of $R^8$, $R^{4a}$, $R^{4b}$, $R^{4c}$ and $R^{4d}$ are given in Table 1 wherein the values of $R^8$, $R^{4a}$, $R^{4b}$, $R^{4c}$ and $R^{4d}$ are given in Table 1

Table XXXVII provides 782 compounds of formula Iak

Table XL provides 782 compounds of formula Ian

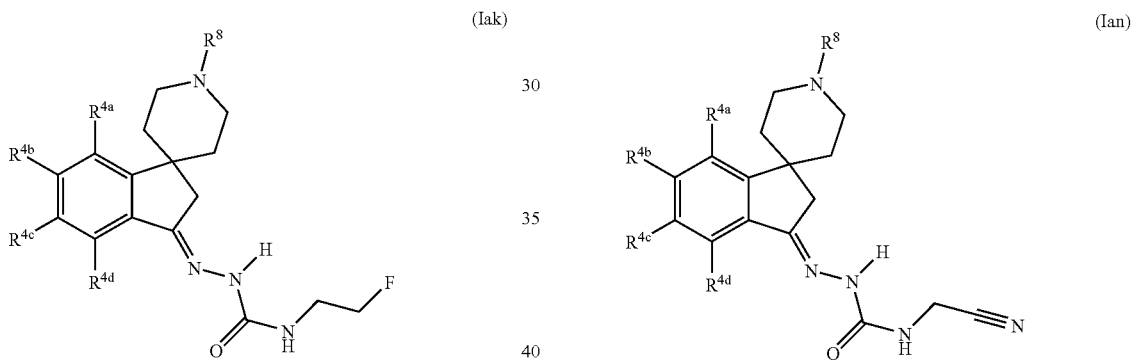

wherein the values of $R^8$, $R^{4a}$, $R^{4b}$, $R^{4c}$ and $R^{4d}$ are given in Table 1 wherein the values of $R^8$, $R^{4a}$, $R^{4b}$, $R^{4c}$ and $R^{4d}$ are given in Table 1

Table XXXVIII provides 782 compounds of formula Ial

Table XLI provides 782 compounds of formula Iao

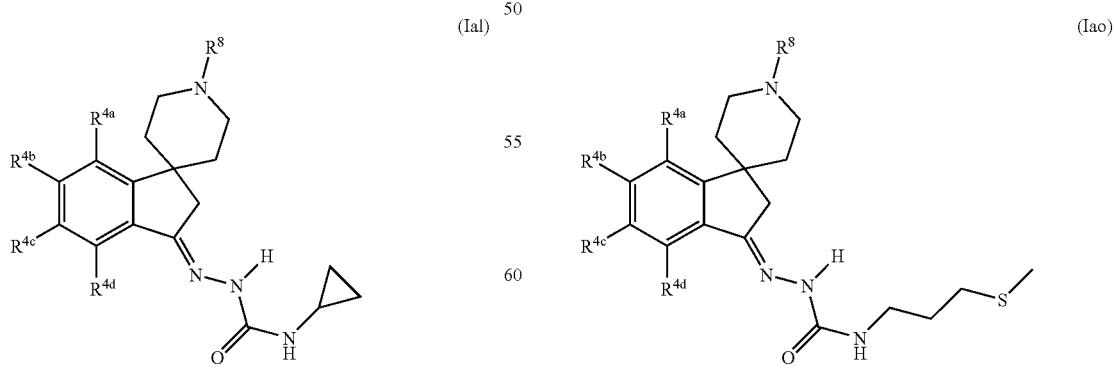

wherein the values of $R^8$, $R^{4a}$, $R^{4b}$, $R^{4c}$ and $R^{4d}$ are given in Table 1 wherein the values of $R^8$, $R^{4a}$, $R^{4b}$, $R^{4c}$ and $R^{4d}$ are given in Table 1

Table XLII provides 782 compounds of formula Iap

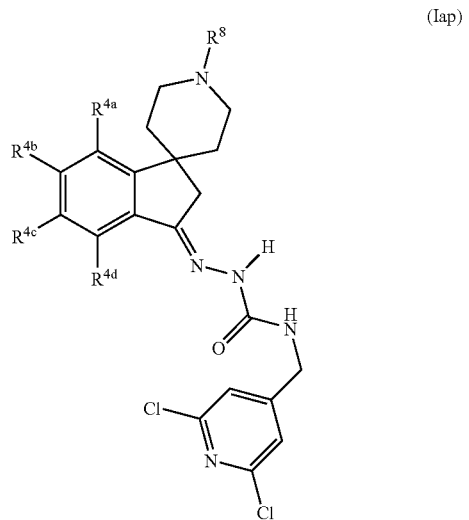

wherein the values of $R^8$, $R^{4a}$, $R^{4b}$, $R^{4c}$ and $R^{4d}$ are given in Table 1

Table XLIII provides 782 compounds of formula Iaq

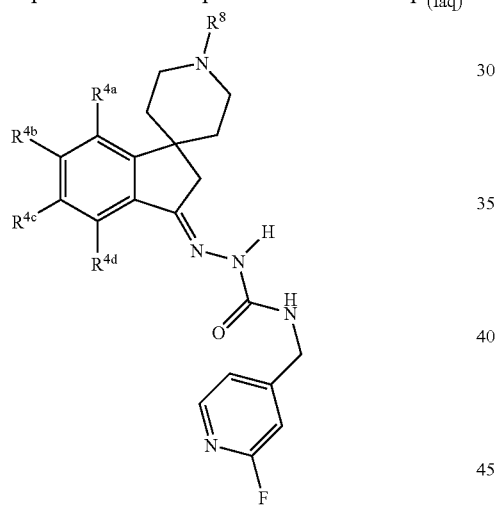

wherein the values of $R^8$, $R^{4a}$, $R^{4b}$, $R^{4c}$ and $R^{4d}$ are given in Table 1.

Table XLIV provides 782 compounds of formula Iar

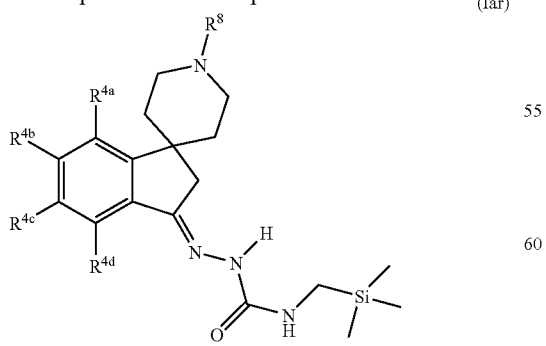

wherein the values of $R^8$, $R^{4a}$, $R^{4b}$, $R^{4c}$ and $R^{4d}$ are given in Table 1.

Table XLV provides 782 compounds of formula Ias

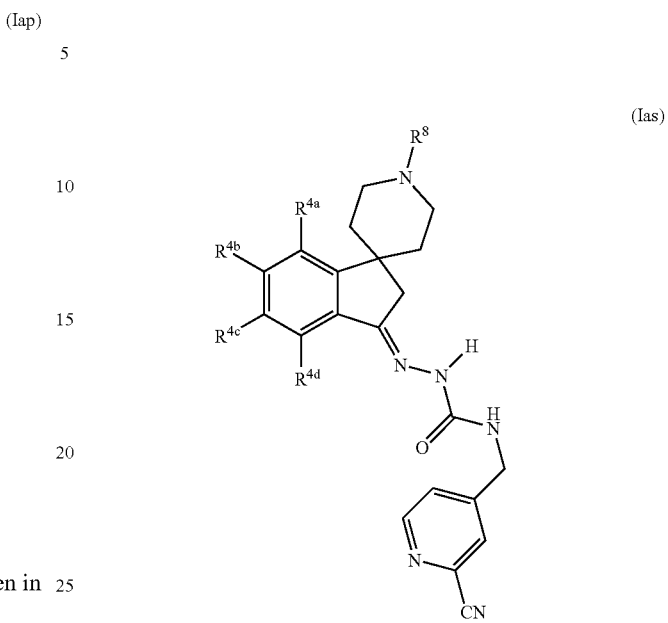

wherein the values of $R^8$, $R^{4a}$, $R^{4b}$, $R^{4c}$ and $R^{4d}$ are given in Table 1.

Table XLVI provides 782 compounds of formula Iat

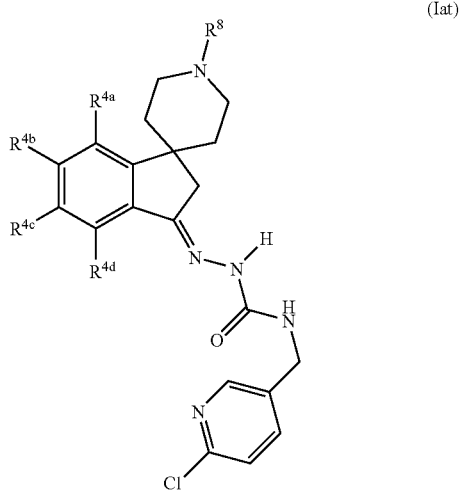

wherein the values of $R^8$, $R^{4a}$, $R^{4b}$, $R^{4c}$ and $R^{4d}$ are given in Table 1.

Table XLVII provides 782 compounds of formula Iau

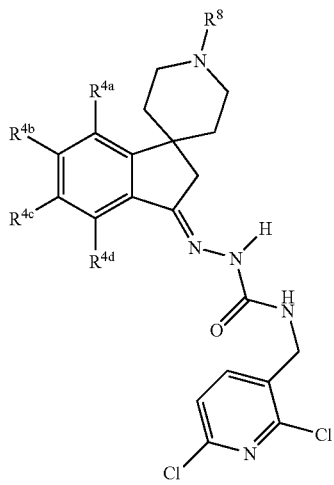
(Iau)

wherein the values of $R^8$, $R^{4a}$, $R^{4b}$, $R^{4c}$ and $R^{4d}$ are given in Table 1.

Table XLVIII provides 782 compounds of formula Iav

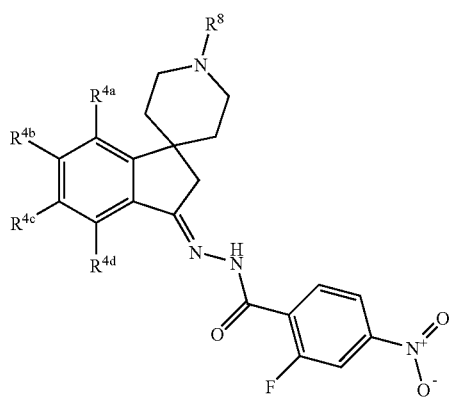
(Iav)

wherein the values of $R^8$, $R^{4a}$, $R^{4b}$, $R^{4c}$ and $R^{4d}$ are given in Table 1.

Table XLIX provides 782 compounds of formula Iaw

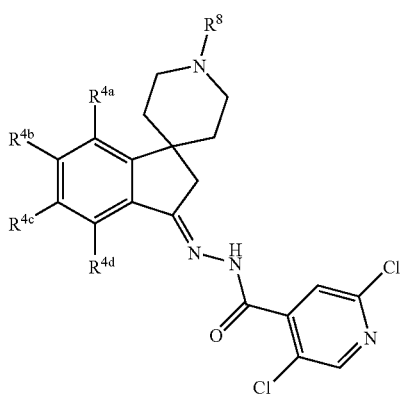
(Iaw)

wherein the values of $R^8$, $R^{4a}$, $R^{4b}$, $R^{4c}$ and $R^{4d}$ are given in Table 1.

Table L provides 782 compounds of formula Iax

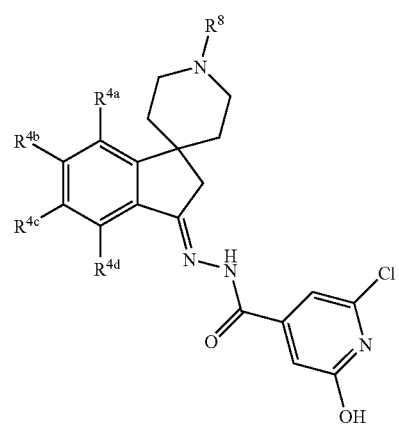
(Iax)

wherein the values of $R^8$, $R^{4a}$, $R^{4b}$, $R^{4c}$ and $R^{4d}$ are given in Table 1.

Table LI provides 782 compounds of formula Iay

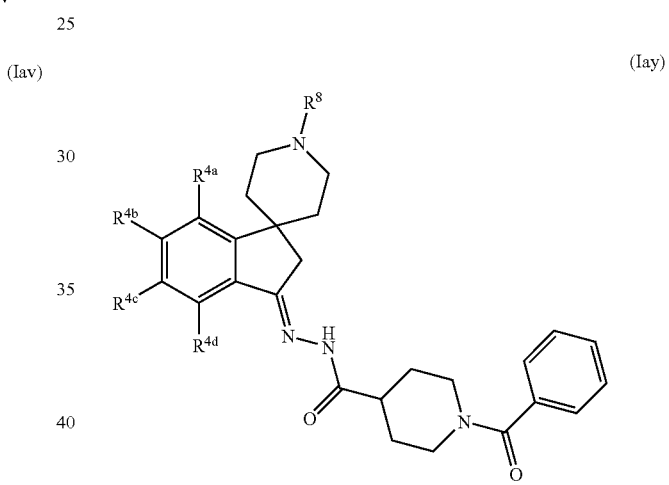
(Iay)

wherein the values of $R^8$, $R^{4a}$, $R^{4b}$, $R^{4c}$ and $R^{4d}$ are given in Table 1.

Table LII provides 782 compounds of formula Iaz

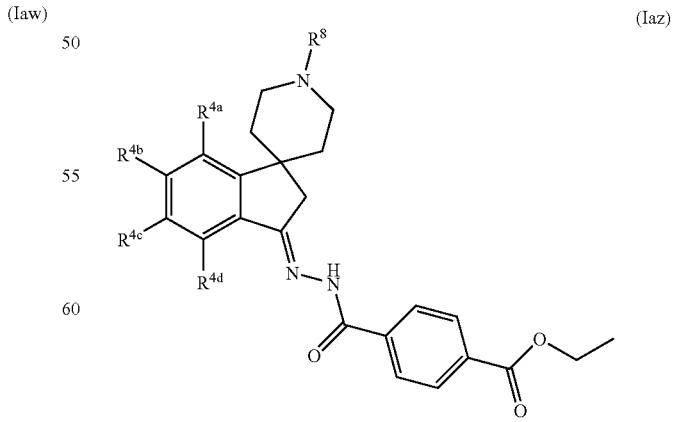
(Iaz)

wherein the values of $R^8$, $R^{4a}$, $R^{4b}$, $R^{4c}$ and $R^{4d}$ are given in Table 1.

Table LEI provides 782 compounds of formula Iba

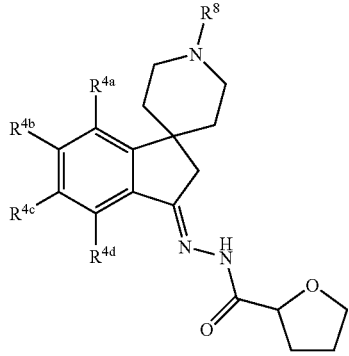
(Iba)

wherein the values of $R^8$, $R^{4a}$, $R^{4b}$, $R^{4c}$ and $R^{4d}$ are given in Table 1.

Table LIV provides 782 compounds of formula Ibb

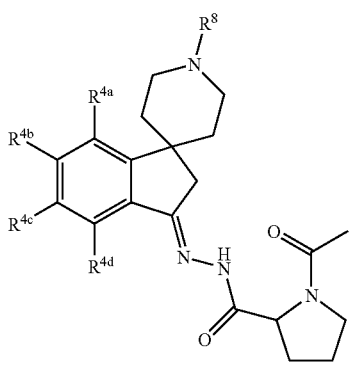
(Ibb)

wherein the values of $R^8$, $R^{4a}$, $R^{4b}$, $R^{4c}$ and $R^{4d}$ are given in Table 1.

Table LV provides 782 compounds of formula Ibc

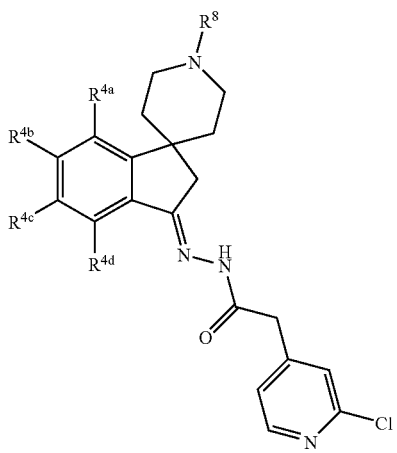
(Ibc)

wherein the values of $R^8$, $R^{4a}$, $R^{4b}$, $R^{4c}$ and $R^{4d}$ are given in Table 1.

Table LVI provides 782 compounds of formula Ibd

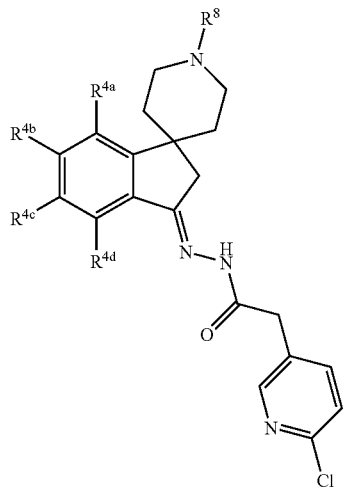
(Ibd)

wherein the values of $R^8$, $R^{4a}$, $R^{4b}$, $R^{4c}$ and $R^{4d}$ are given in Table 1.

Table LVII provides 782 compounds of formula Ibe

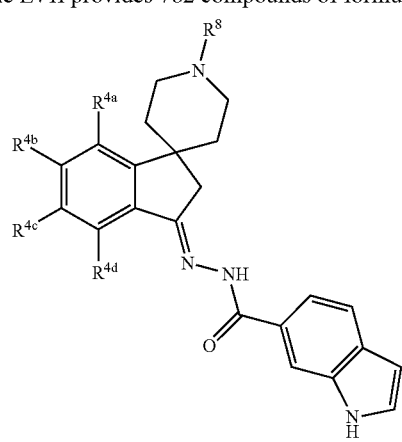
(Ibe)

wherein the values of $R^8$, $R^{4a}$, $R^{4b}$, $R^{4c}$ and $R^{4d}$ are given in Table 1.

Table LVIII provides 782 compounds of formula Ibf

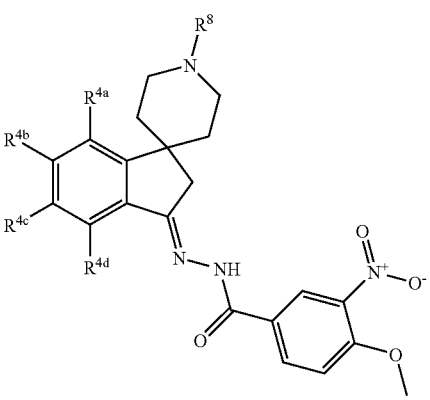
(Ibf)

wherein the values of $R^8$, $R^{4a}$, $R^{4b}$, $R^{4c}$ and $R^{4d}$ are given in Table 1.

Table LIX provides 782 compounds of formula Ibg

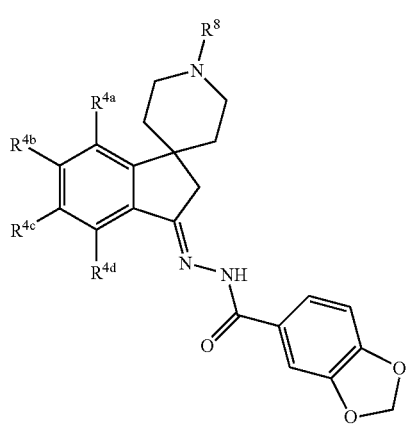
(Ibg)

wherein the values of $R^8$, $R^{4a}$, $R^{4b}$, $R^{4c}$ and $R^{4d}$ are given in Table 1.

Table LX provides 782 compounds of formula Ibh

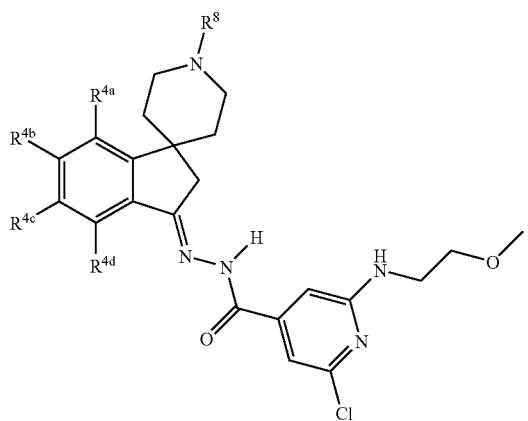
(Ibh)

wherein the values of $R^8$, $R^{4a}$, $R^{4b}$, $R^{4c}$ and $R^{4d}$ are given in Table 1.

Table LXI provides 782 compounds of formula Ibi

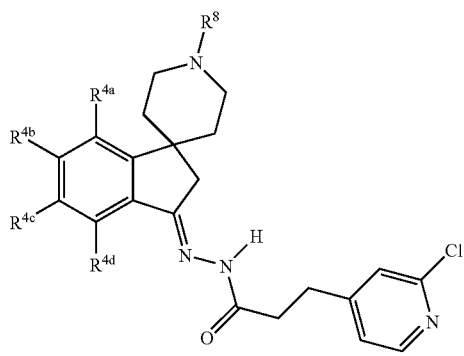
(Ibi)

wherein the values of $R^8$, $R^{4a}$, $R^{4b}$, $R^{4c}$ and $R^{4d}$ are given in Table 1.

Table LXIII provides 782 compounds of formula Ibk

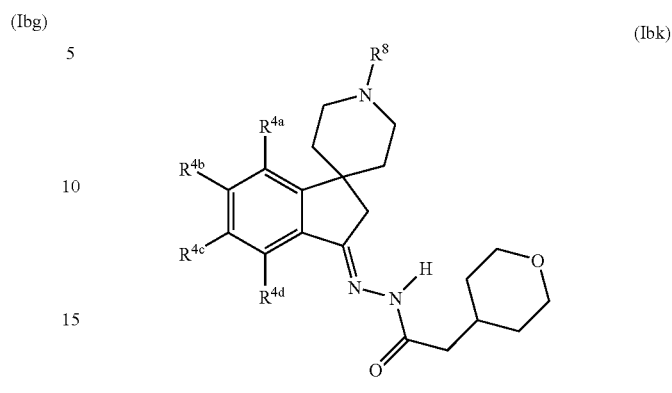
(Ibk)

wherein the values of $R^8$, $R^{4a}$, $R^{4b}$, $R^{4c}$ and $R^{4d}$ are given in Table 1.

Table LXIV provides 782 compounds of formula Ibl

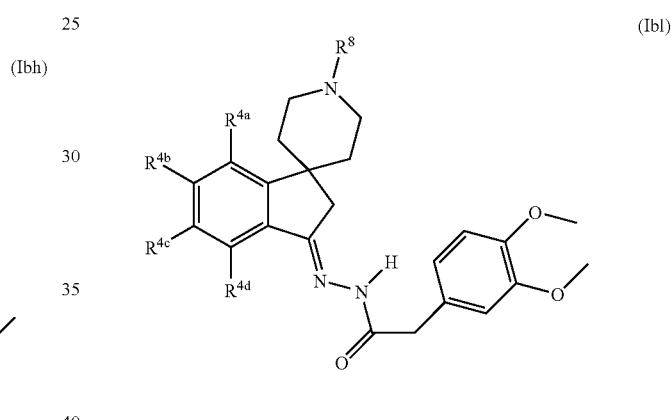
(Ibl)

wherein the values of $R^8$, $R^{4a}$, $R^{4b}$, $R^{4c}$ and $R^{4d}$ are given in Table 1.

Table LXV provides 782 compounds of formula Ibm

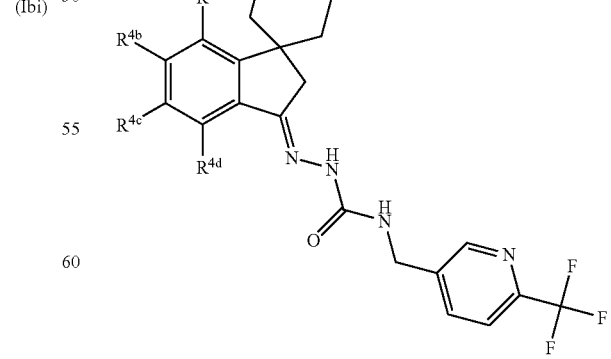
(Ibm)

wherein the values of $R^8$, $R^{4a}$, $R^{4b}$, $R^{4c}$ and $R^{4d}$ are given in Table 1.

Table LXVI provides 782 compounds of formula Ibn

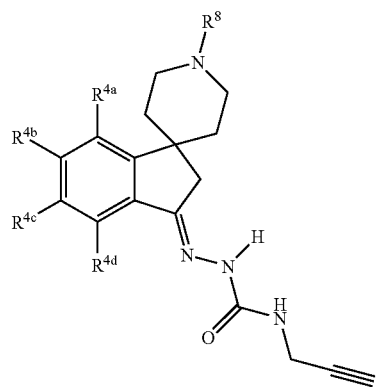

(Ibn)

wherein the values of $R^8$, $R^{4a}$, $R^{4b}$, $R^{4c}$ and $R^{4d}$ are given in Table 1.

Table LXVII provides 782 compounds of formula Ibo

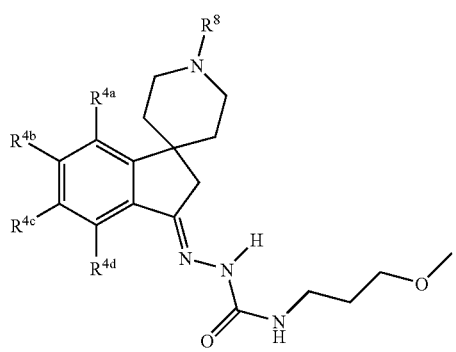

(Ibo)

wherein the values of $R^8$, $R^{4a}$, $R^{4b}$, $R^{4c}$ and $R^{4d}$ are given in Table 1.

Table LXVIII provides 15 compounds of formula Ica

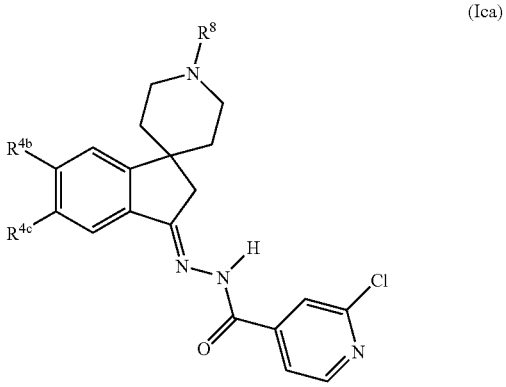

(Ica)

wherein the values of $R^{4b}$, $R^{4c}$ and $R^8$ are given in Table 2 together with LCMS/MS data obtained as for the data in Table 5 below.

TABLE 2

| Compound | $R^{4b}$ | $R^{4c}$ | $R^8$ | M.p. | LCMS (Ret. Time, min) | MS data |
|---|---|---|---|---|---|---|
| LXVIII.1 | H | H | H | 175-180 | 1'35 | 355 |
| LXVIII.2 | H | H | t-butoxycarbonyl | 90-95 | 3'38 | 455 |
| LXVIII.3 | H | H | 4-trifluoromethoxybenzyl | | 2'06 | 529 |
| LXVIII.4 | H | H | 4-trifluoromethylbenzyl | | 2'01 | 513 |
| LXVIII.5 | H | H | 4-isopropyloxycarbonylamino-benzyl | | 1'91 | 546 |
| LXVIII.6 | H | H | 4-(2-Ethyl-2H-tetrazol-5-yl)-benzyl | | 1'88 | 541 |
| LXVIII.7 | H | H | 4-cyanobenzyl | | 1'71 | 470 |
| LXVIII.8 | H | H | 4-fluorobenzyl | | 1'74 | 463 |
| LXVIII.9 | H | H | benzyl | | 1'67 | 445 |
| LXVIII.10 | H | H | 2,6-difluorobenzyl | | 1'70 | 481 |
| LXVIII.11 | H | H | 3-chlorobenzyl | | 1'88 | 479 |
| LXVIII.12 | H | H | 1-phenyl-ethyl | | 1'74 | 459 |
| LXVIII.13 | H | H | methyl | | 1'32 | 369 |
| LXVIII.14 | Cl | H | t-butoxycarbonyl | 165 | 3'68 | 433, 473 |
| LXVIII.15 | H | Cl | t-butoxycarbonyl | 165 | 3'65 | 433, 473 |

Table LXIX provides 23 compounds of formula Icb

Table LXX provides 3 compounds of formula Icc together with LCMS/MS data obtained as for the data in Table 5 below.

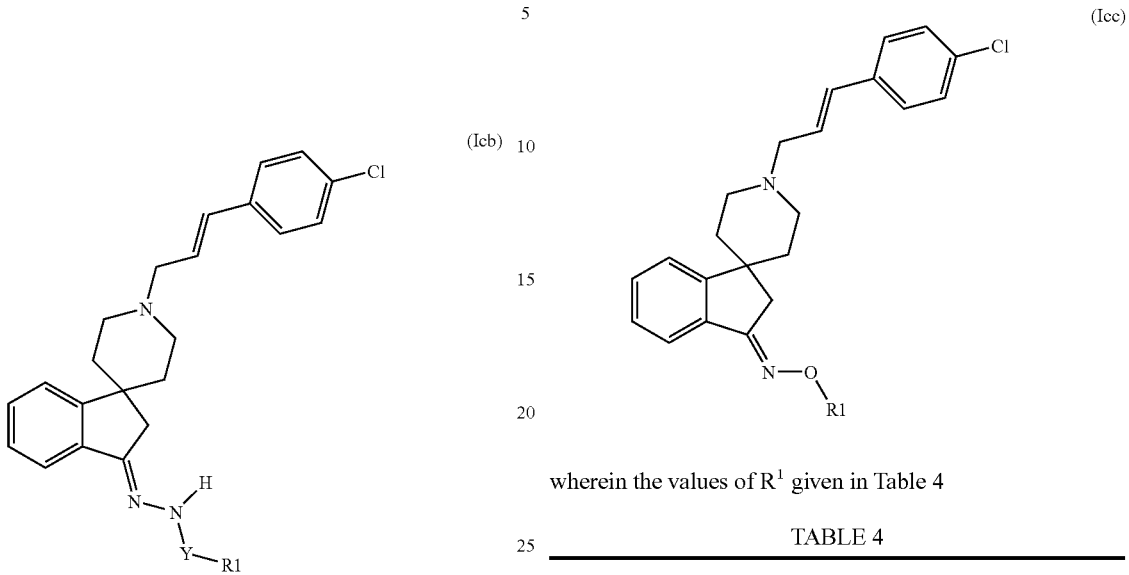

(Icb)

(Icc)

wherein the values of R¹ given in Table 4

TABLE 4

| Compound | R¹ | M.p. | LCMS (Ret. Time, min) | MS data |
|---|---|---|---|---|
| LXX.1 | H | 203 | 1'76 | 367/369 | wherein the values of Y and R¹ are given in Table 3 together with LCMS/MS data obtained as for the data in Table 5 below.

Mass spectra data were obtained for selected compounds of Tables I to LXVII using LCMS: LC5: 254 nm—gradient 10% A to 100% B A=H2O+0.01% HCOOH

TABLE 3

| Compound | Y | R¹ | M.p. | LCMS (Ret. Time, min) | LCMS (M + H) |
|---|---|---|---|---|---|
| LXIX.1 | bond | H | 140-142 | 1'70 | 366 |
| LXIX.2 | C=O | phenyl | | 2'00 | 470 |
| LXIX.3 | C=O | 2-furyl | | 1'91 | 460 |
| LXIX.4 | C=O | 3-pyridyl | | 1'82 | 471 |
| LXIX.5 | C=O | 4-trifluoromethoxyphenylamino | 225 | 2'65 | 569 |
| LXIX.6 | C=O | 2,4-dichlorophenylamino | 215-220 | 2'81 | 554 |
| LXIX.7 | C=O | 4-methoxyphenylamino | 270 | 2'38 | 515 |
| LXIX.8 | C=O | 3-methoxyphenylamino | 230 | 2'45 | 515 |
| LXIX.9 | C=O | 2-chlorophenylamino | | 2'62 | 519 |
| LXIX.10 | C=O | 3-chlorophenylamino | | 2'58 | 519 |
| LXIX.11 | C=O | 4-chlorophenylamino | 235 | 2'59 | 519 |
| LXIX.12 | C=O | 3-trifluoromethyl-phenylamino | 230 | 2'67 | 553 |
| LXIX.13 | C=O | 4-trifluoromethylphenyl | 200 | 2'37 | 538 |
| LXIX.14 | C=O | 4-chlorophenyl | 200 | 2'28 | 504 |
| LXIX.15 | C=O | phenylamino | 230 | 2'35 | 485 |
| LXIX.16 | C=O | 2-chlorophenyl | 180 | 2'19 | 504 |
| LXIX.17 | C=O | 2-hydroxyphenyl | 230 | 2'10 | 486 |
| LXIX.18 | C=O | 4-nitrophenyl | 190 | 2'16 | 515 |
| LXIX.19 | C=O | 3,5-di(trifluoromethyl)phenyl | 190 | 2'60 | 506 |
| LXIX.20 | C=O | 2-chloro-6-methoxy-pyrid-4-yl | 210 | 2'31 | 535 |
| LXIX.21 | C=O | 2-chloro-6-methyl-pyrid-4-yl | 209 | 2'15 | 519 |
| LXIX.22 | C=O | 2-amino-pyrid-3-yl | 225 | 1'61 | 486 |
| LXIX.23 | C=O | 4-trifluoromethyl-phenylamino | | 2'62 | 553 |

B=CH3CN/CH3OH+0.01% HCOOH positive electrospray 150-1000 m/z.

The data are shown in Table 5.

TABLE 5

| Compound | M.p. | LCMS (Ret. Time, min) | MS data |
|---|---|---|---|
| I.3 | | 1'81 | 408 |
| II.3 | | 1'79 | 471 |
| III.1 | 198-200 | 1'88 | 479 |
| III.3 | 240 | 2'07 | 505 |
| III.6 | 235 | 2'13 | 539 |
| III.7 | 113 | 2'30 | 555 |
| III.26 | 205 | 2'18 | 523 |
| III.29 | 230 | 2'27 | 557 |
| III.30 | 205 | 2'28 | 573 |
| III.49 | 212 | 2'28 | 540 |
| III.52 | | 2'36 | 573 |
| III.53 | | 2'43 | 589 |
| III.210 | 210 | 2'28 | 540 |
| III.213 | | 2'36 | 573 |
| III.214 | | 2'48 | 589 |
| III.233 | 180 | 2'18 | 523 |
| III.236 | 210 | 2'22 | 557 |
| III.237 | | 2'26 | 573 |
| V.3 | 185 | 2'33 | 540 |
| XII.3 | | 1'84 | 424 |

The compounds of the invention may be made in a variety of ways. Thus for example they may be made by the reactions summarised in Scheme I.

Thus a compound of formula I may be synthesised from compounds of formula 2a by reaction with a compound of formula $R_1YXNH2$ where X is O or NH at a temperature of between ambient temperature and 120° C., in an organic solvent such as methanol, ethanol, isopropanol, 1,4-dioxan, benzene or toluene in the presence of an acid such as sulphuric acid or a base such as sodium hydroxide or sodium acetate.

A compound of formula 1 may also be synthesised from compounds of formula 3a by reaction with an alkylating agent of the formula R8-L, where L is chloride, bromide, iodide or a sulfonate (e.g. mesylate or tosylate) or similar leaving group at a temperature of between ambient temperature and 100° C., typically ambient temperature, in an organic solvent such as acetonitrile, dimethylformamide, dichloromethane, chloroform or 1,2-dichloroethane in the presence of a tertiary amine base such as triethylamine or diisopropylethylamine and optionally catalysed by halide salts such as sodium iodide, potassium iodide or tetrabutylammonium iodide.

Alternatively, a compound of formula 3a may be reacted with an aldehyde of the formula RCHO at a temperature between ambient temperature and 100° C. in an organic solvent such as tetrahydrofuran or ethanol or mixtures of solvents in the presence of a reducing agent such as borane-pyridine complex, sodium borohydride, sodium (triacetoxy) borohydride, sodium cyanoborohydride or such like, to produce a compound of formula 1 where R8 is $CH_2$—R.

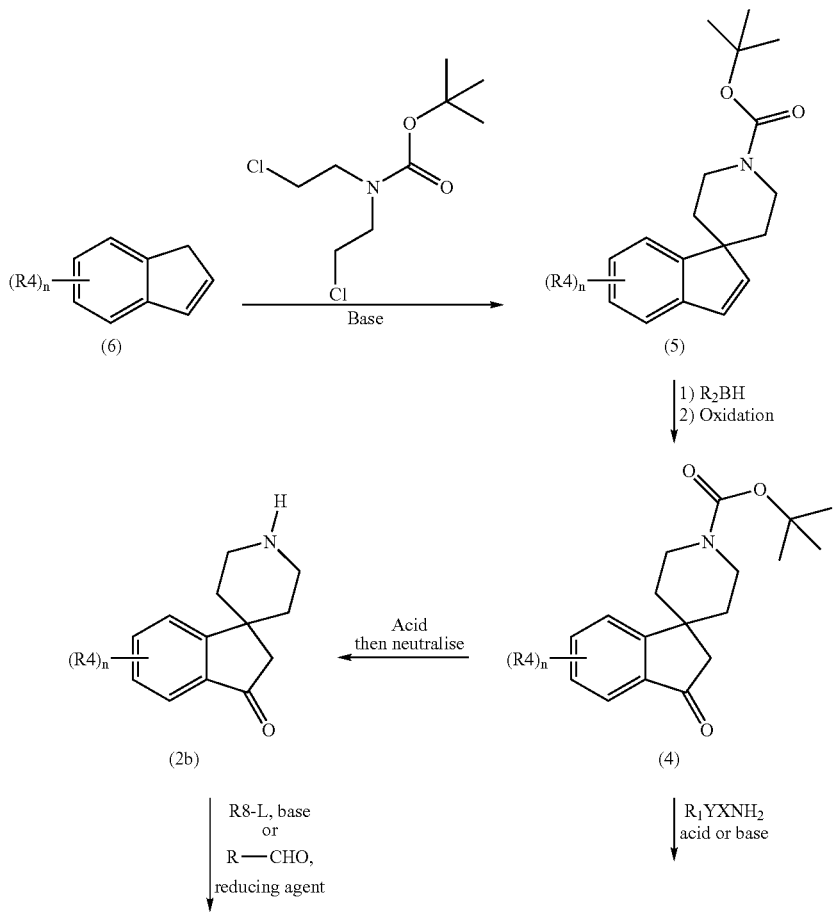

SCHEME I

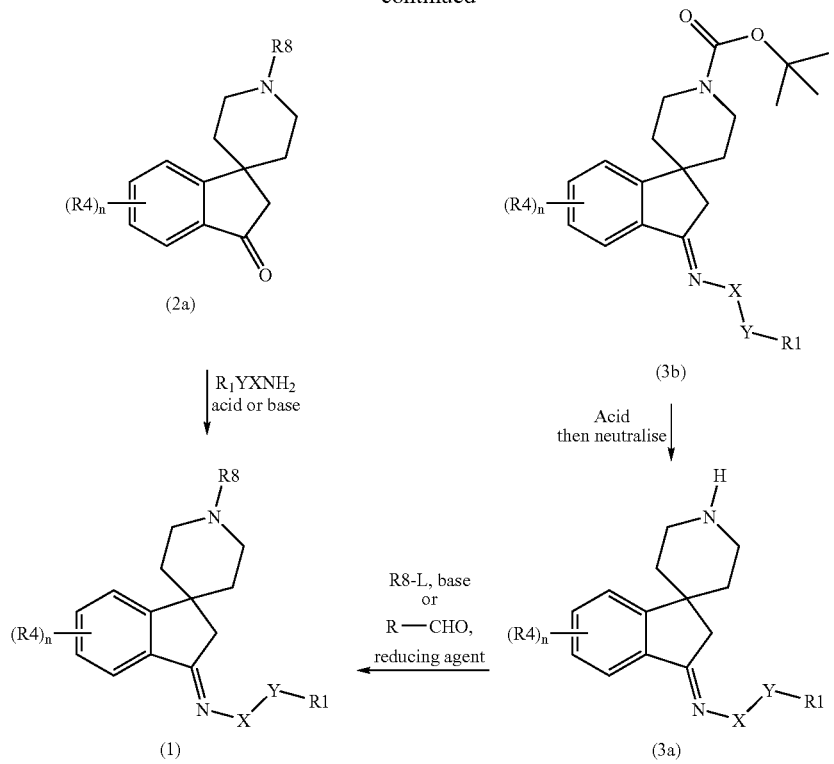

Similarly, a compound of formula 2a may be obtained from a compound of formula 2b by the methods described above for 3a.

A compound of formula 2b (or 3a) may be formed by reaction of a compound of formula 4 (or 3b) with an acid such as trifluoroacetic acid at ambient temperature in an organic solvent such as dichloromethane, chloroform or 1,2-dichloroethane followed by neutralisation with a base such as sodium bicarbonate.

A compound of formula 3b may be formed by reaction of a compound of formula 4 with a compound of formula $R_1YXNU2$ where X is O or NH at a temperature of between ambient temperature and 120° C., in an organic solvent such as methanol, ethanol, isopropanol, 1,4-dioxan, benzene or toluene in the presence of an acid such as sulphuric acid or a base such as sodium hydroxide or sodium acetate.

Compounds of formula 4 may be obtained from compounds of formula 5 by the methods described by Tata et al. in *Biorg. Med. Chem. Lett.* 1997, 663-668.

Compounds of formula 5 may be obtained from indenes of formula 6 by the methods described by Chambers et al. in *J. Med. Chem.* 1992, 35, 2033-2039.

Certain compounds of formula 2a, 2b, 3a, 3b, 4 and 5 are novel and as such form a further aspect of the invention.

Indenes of formula 6 are either known compounds or may be prepared by known methods by a person skilled in the art. An example of those methods is given in *Bull. Soc. Chim. Fr.* 1973, 11, 3092.

Compounds of formula I where $R^2$ and $R^3$ are other than hydrogen may be made by routes described in WO03/106457. Thus for example a compound of formula 4 may be converted to compound of formula 4'

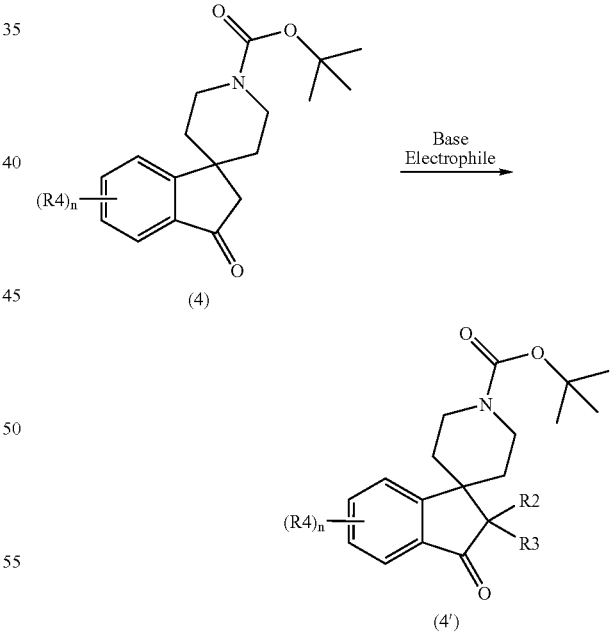

by reaction with an electrophile in the presence of a base and thus to compounds of formula I by the methods outlined above for converting compounds of formula 4 to formula I.

The skilled person will readily recognise that it is possible to interconvert one compound of formula I to other compounds of formula I and examples of such procedures are given in scheme II.

SCHEME II

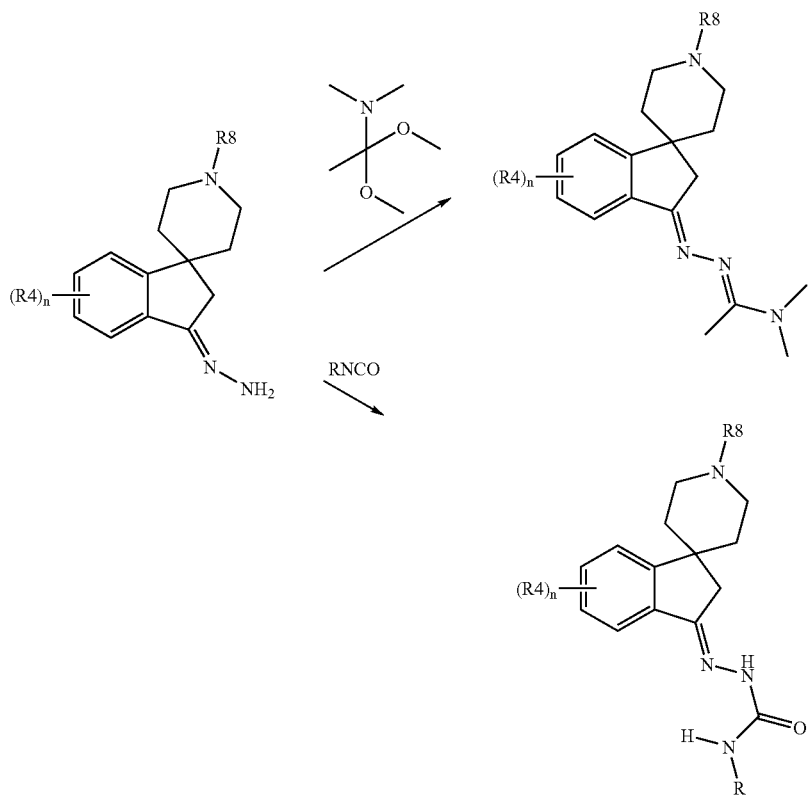

The compounds of formula (I) can be used to combat and control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are hereinafter collectively referred to as pests. The pests which may be combated and controlled by the use of the invention compounds include those pests associated with agriculture (which term includes the growing of crops for food and fibre products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies).

Examples of pest species which may be controlled by the compounds of formula (I) include: *Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (*thrips*), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis*, (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the Mastotermitidae (for example *Mastotermes* spp.), the Kalotermitidae (for example *Neoterines* spp.), the Rhinotermitidae (for example *Coptotermes formosanus*, *Reticulitermes flavipes*, *R. speratu*, *R. virginicus*, *R. hesperus*, and *R. santonensis*) and the Termitidae (for example *Globitermes sulphureus*), *Solenopsis geminata* (fire ant), *Monomoriumn pharaonis* (pharaoh's ant), *Damalinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans* (vinegar eelworm), *Trichostrongylus* spp. (gastro intestinal nematodes) and *Deroceras reticulatum* (slug).

The invention therefore provides a method of combating and controlling insects, acarines, nematodes or molluscs which comprises applying an insecticidally, acaricidally, nematicidally or molluscicidally effective amount of a compound of formula (I), or a composition containing a compound of formula (I), to a pest, a locus of pest, or to a plant susceptible to attack by a pest, The compounds of formula (I) are preferably used against insects, acarines or nematodes.

The term "plant" as used herein includes seedlings, bushes and trees.

In order to apply a compound of formula (I) as an insecticide, acaricide, nematicide or molluscicide to a pest, a locus of pest, or to a plant susceptible to attack by a pest, a compound of formula (I) is usually formulated into a composition which includes, in addition to the compound of formula (I), a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (I). The composition is generally used for the control of pests such that a compound of formula (I) is applied at a rate of from 0.1 g to 10 kg per hectare, preferably from 1 g to 6 kg per hectare, more preferably from 1 g to 1 kg per hectare.

When used in a seed dressing, a compound of formula (I) is used at a rate of 0.0001 g to 10 g (for example 0.001 g or 0.05 g), preferably 0.005 g to 10 g, more preferably 0.005 g to 4 g, per kilogram of seed.

In another aspect the present invention provides an insecticidal, acaricidal, nematicidal or molluscicidal composition comprising an insecticidally, acaricidally, nematicidally or molluscicidally effective amount of a compound of formula (I) and a suitable carrier or diluent therefor. The composition is preferably an insecticidal, acaricidal, nematicidal or molluscicidal composition.

In a still further aspect the invention provides a method of combating and controlling pests at a locus which comprises treating the pests or the locus of the pests with an insecticidally, acaricidally, nematicidally or molluscicidally effective amount of a composition comprising a compound of formula (I). The compounds of formula (I) are preferably used against insects, acarines or nematodes.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (I).

Dustable powders (DP) may be prepared by mixing a compound of formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (I) and one or more powdered solid diluents or carriers, or from pre-formed blank granules by absorbing a compound of formula (I) (or a solution thereof, in a suitable agent) in a porous granular material (such as pumice, attapulgite clays, fuller's earth, kieselguhr, diatomaceous earths or ground corn cobs) or by adsorbing a compound of formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula (I) is present initially in either the water or the solvent/SFA blend. Suitable solvents for use in MEs include those hereinbefore described for use in in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (I). SCs may be prepared by ball or bead milling the solid compound of formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (I) may be dry milled and added to water, containing agents hereinbefore described, to produce the desired end product.

Aerosol formulations comprise a compound of formula (I) and a suitable propellant (for example n-butane). A compound of formula (I) may also be dissolved or dispersed in a suitable medium (for example water or a water miscible liquid, such as n-propanol) to provide compositions for use in non-pressurised, hand-actuated spray pumps.

A compound of formula (I) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of formula (I) and, optionally, a carrier or diluent therefor. The polymeric shell may be produced by either an interfacial polycondensation reaction or by a coacervation procedure. The compositions may provide for controlled release of the compound of formula (I) and they may be used for seed treatment. A compound of formula (I) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (I)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (I)).

A compound of formula (I) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (I) may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapour or applied through distribution or incorporation of a composition (such as a granular composition or a composition packed in a water-soluble bag) in soil or an aqueous environment.

A compound of formula (I) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (I) (for example 0.0001 to 10%, by weight) depending upon the purpose for which they are to be used.

A compound of formula (I) may be used in mixtures with fertilisers (for example nitrogen-, potassium- or phosphorus-containing fertilisers). Suitable formulation types include granules of fertiliser. The mixtures suitably contain up to 25% by weight of the compound of formula (I).

The invention therefore also provides a fertiliser composition comprising a fertiliser and a compound of formula (I).

The compositions of this invention may contain other compounds having biological activity, for example micronutrients or compounds having fungicidal activity or which possess plant growth regulating, herbicidal, insecticidal, nematicidal or acaricidal activity.

The compound of formula (I) may be the sole active ingredient of the composition or it may be admixed with one or more additional active ingredients such as a pesticide, fungicide, synergist, herbicide or plant growth regulator where appropriate. An additional active ingredient may: provide a composition having a broader spectrum of activity or increased persistence at a locus; synergise the activity or complement the activity (for example by increasing the speed of effect or overcoming repellency) of the compound of formula (I); or help to overcome or prevent the development of resistance to individual components. The particular additional active ingredient will depend upon the intended utility of the composition. Examples of suitable pesticides include the following:

a) Pyrethroids, such as permethrin, cypermethrin, fenvalerate, esfenvalerate, deltamethrin, cyhalothrin (in particular lambda-cyhalothrin), bifenthrin, fenpropathrin, cyfluthrin, tefluthrin, fish safe pyrethroids (for example ethofenprox), natural pyrethrin, tetramethrin, s-bioallethrin, fenfluthrin, pralletluin or 5-benzyl-3-furylmethyl-(E)-(1R,3S)-2,2- dimethyl-3- (2-oxothiolan-3-ylidenemethyl)cyclopropane carboxylate;
b) Organophosphates, such as, profenofos, sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate or diazinon;
c) Carbamates (including aryl carbamates), such as pirimicarb, triazamate, cloethocarb, carbofuran, furathiocarb, ethiofencarb, aldicarb, thiofurox, carbosulfan, bendiocarb, fenobucarb, propoxur, methomyl or oxamyl;
d) Benzoyl ureas, such as diflubenzuron, triflumuron, hexaflumuron, flufenoxuron or chlorfluazuron;
e) Organic tin compounds, such as cyhexatin, fenbutatin oxide or azocyclotin;
f) Pyrazoles, such as tebufenpyrad and fenpyroximate;
g) Macrolides, such as avermectins or milbemycins, for example abamectin, emamectin benzoate, ivermectin, milbemycin, spinosad or azadirachtin;
h) Hormones or pheromones;
i) Organochlorine compounds such as endosulfan, benzene hexachloride, DDT, chlordane or dieldrin;
j) Amidines, such as chlordimeform or amitraz;
k) Fumigant agents, such as chloropicrin, dichloropropane, methyl bromide or metam;
l) Chloronicotinyl compounds such as imidacloprid, thiacloprid, acetamiprid, nitenpyram or thiamethoxam;
m) Diacylhydrazines, such as tebufenozide, chromafenozide or methoxyfenozide;
n) Diphenyl ethers, such as diofenolan or pyriproxifen;
o) Indoxacarb;
p) Chlorfenapyr; or
q) Pymetrozine.

In addition to the major chemical classes of pesticide listed above, other pesticides having particular targets may be employed in the composition, if appropriate for the intended utility of the composition. For instance, selective insecticides for particular crops, for example stemborer specific insecticides (such as cartap) or hopper specific insecticides (such as buprofezin) for use in rice may be employed. Alternatively insecticides or acaricides specific for particular insect species/stages may also be included in the compositions (for example acaricidal ovo-larvicides, such as clofentezine, flubenzimine, hexythiazox or tetradifon; acaricidal motilicides, such as dicofol or propargite; acaricides, such as bromopropylate or chlorobenzilate; or growth regulators, such as hydramethylnon, cyromazine, methoprene, chlorfluazuron or diflubenzuron).

Examples of fungicidal compounds which may be included in the composition of the invention are (E)-N-methyl-2-[2-(2,5-dimethylphenoxymethyl)phenyl]-2-methoxyiminoacetamide (SSF-129), 4-bromo-2-cyano-N,N-dimethyl-6-trifluoromethylbenzimidazole-1-sulphonamide, α-[N-(3-chloro-2,6-xylyl)-2-methoxyacetamido]-γ-butyrolactone, 4-chloro-2-cyano-N,N-dimethyl-5-p-tolylimidazole-1-sulfonamide (IKF-916, cyamidazosulfamid), 3-5-dichloro-N-(3-chloro-1-ethyl-1-methyl-2-oxopropyl)-4-methylbenzamide (RH-7281, zoxamide), N-allyl-4,5,-dimethyl-2-trimethylsilylthiophene-3-carboxamide (MON65500), N-(1-cyano-1,2-dimethylpropyl)-2-(2,4-dichlorophenoxy)propionamide (AC382042), N-(2-methoxy-5-pyridyl)-cyclopropane carboxamide, acibenzolar (CGA245704), alanycarb, aldimorph, anilazine, azaconazole, azoxystrobin, benalaxyl, benomyl, biloxazol, bitertanol, blasticidin S, bromuconazole, bupirimate, captafol, captan, carbendazim, carbendazim chlorhydrate, carboxin, carpropamid, carvone, CGA41396, CGA41397, chinomethionate, chlorothalonil, chlorozolinate, clozylacon, copper containing compounds such as copper oxychloride, copper oxyquinolate, copper sulphate, copper tallate and Bordeaux mixture, cymoxanil, cyproconazole, cyprodinil, debacarb, di-2-pyridyl disulphide 1,1'-dioxide, dichlofluanid, diclomezine, dicloran, diethofencarb, difenoconazole, difenzoquat, diflumetorim, O,O-di-iso-propyl-S-benzyl thiophosphate, dimefluazole, dimetconazole, dimethomorph, dimethirimol, diniconazole, dinocap, dithianon, dodecyl dimethyl ammonium chloride, dodemorph, dodine, doguadine, edifenphos, epoxiconazole, ethirimol, ethyl(Z)-N-benzyl-N([methyl(methyl-thioethylideneaminooxycarbonyl)amino]thio)-β-alaninate, etridiazole, famoxadone, fenamidone (RPA407213), fenarimol, fenbuconazole, fenfuram, fenhexamid (KBR2738), fenpiclonil, fenpropidin, fenpropimorph, fentin acetate, fentin hydroxide, ferbam, ferimzone, fluazinam, fludioxonil, flumetover, fluoroimide, fluquinconazole, flusilazole, flutolanil, flutriafol, folpet, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb (SZX0722), isopropanyl butyl carbamate, isoprothiolane, kasugamycin, kresoxim-methyl, LY186054, LY211795, LY248908, mancozeb, maneb, mefenoxam, mepanipyrim, mepronil, metalaxyl, metconazole, metiram, metiram-zinc, metominostrobin, myclobutanil, neoasozin, nickel dimethyldithiocarbamate, nitrothal-isopropyl, nuarimol, ofurace, organomercury compounds, oxadixyl, oxasulfuron, oxolinic acid, oxpoconazole, oxycarboxin, pefurazoate, penconazole, pencycuron, phenazin oxide, phosetyl-Al, phosphorus acids, phthalide, picoxystrobin (ZA1963), polyoxin D, polyram, probenazole, prochloraz, procymidone, propamocarb, propiconazole, propineb, propionic acid, pyrazophos, pyrifenox, pyrimethanil, pyroquilon, pyroxyfur, pyrrolnitrin, quaternary ammonium compounds, quinomethionate, quinoxyfen, quintozene, sipconazole (F-155), sodium pentachlorophenate, spiroxamine, streptomycin, sulphur, tebuconazole, tecloftalam, tecnazene, tetraconazole, thiabendazole, thifluzamid, 2-(thiocyanomethylthio)benzothiazole, thiophanate-methyl, thiram, timibenconazole, tolclofos-methyl, tolylfluanid, triadimefon, triadimenol, triazbutil, triazoxide, tricyclazole, tridemorph, trifloxystrobin (CGA279202), triforine, triflumizole, triticonazole, validamycin A, vapam, vinclozolin, zineb and ziram.

The compounds of formula (I) may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The invention is illustrated by the following Examples:

EXAMPLE 1

This Example illustrates the preparation of compound LXX.1, 1'-[trans-3-(4-chlorophenyl)allyl]spiro[(indan-1-one)oxime-3,4'-piperidine]

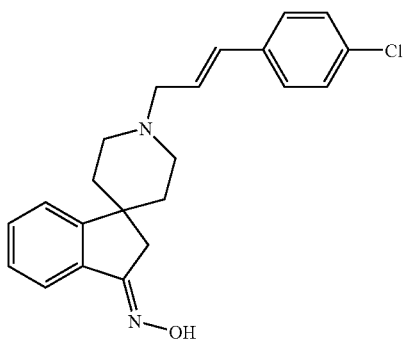 [SMILES: O/N=C1\CC2(CCN(C/C=C/c3ccc(Cl)cc3)CC2)c2ccccc21]

Step A:
Trifluoroacetic acid (27 ml) was added to a stirred solution of spiro[indan-1-one-3,4'-piperidine]-1'-carboxylic acid tert-butyl ester (3.5 g, prepared according to WO 9736873) in anhydrous dichloromethane (90 ml). The reaction mixture was stirred at room temperature for 1 hour, the washed with saturated bicarbonate solution, dried over sodium sulphate and concentrated in vacuo to yield 2.3 g of spiro[indan-1-one-3,4'-piperidine] as a brown oil, which was used directly in the next step.

Step B:
Potassium carbonate (15.5 g) and 4-chlorocinnamyl chloride (2.1 g) were added to a solution of spiro[indan-1-one-3,4'-piperidine] (2.3 g) in acetonitrile (50 ml) under argon, and the yellow mixture was stirred at 70° C. for 2 hours. The reaction mixture was filtered and the solvent evaporated in vacuo. The residue was partitioned between ethyl acetate and water, the organic layer was dried (sodium sulphate), filtered and concentrated in vacuo. The crude product was purified by chromatography [SiO$_2$; ethyl acetate-cyclohexane:triethylamine (1:1:0.1)] to give 1.65 g of 1'-[trans-3-(4-chlorophenyl)allyl]spiro[indan-1-one-3,4'-piperidine] as a yellow oil; $^1$H NMR (400 MHz, CDCl$_3$) 1.50 (m, 2H), 2.08 (m, 4H), 2.53 (s, 2H), 3.01 (d, J=8 Hz, 2H), 3.16 (d, J=6.8 Hz, 2H), 6.23 (dt, J=16 Hz, 6.8 Hz, 1H), 6.45 (d, J=16 Hz, 1H), 7.19-7.71 (m, 8H); MS (ES+) 352/354 (M+H$^+$).

Step C:
To a solution of 1'-[trans-3-(4-chlorophenyl)allyl]spiro[indan-1-one-3,4'-piperidine] (50 mg) in methanol (5 ml) were added sodium acetate (28 mg) and hydroxylamine hydrochloride (22 mg). The reaction mixture was refluxed for 2 hours and concentrated in vacuo. The residue was dissolved in dichloromethane, washed with water, dried (sodium sulphate) and concentrated in vacuo. Silica gel chromatography of the residue (eluent EtOH: ethyl acetate 9:1) afforded 40 mg of 1'-[trans-3-(4-chlorophenyl)allyl]spiro[indan-1-one-(E)-oxime-3,4'-piperidine] and 7 mg of 1'-[trans-3-(4-chlorophenyl)allyl]spiro[indan-1-one-(Z)-oxime-3,4'-piperidine] which were characterised by mass and NMR spectra. 1'-[trans-3-(4-chlorophenyl)allyl]spiro[indan-1-one-(E)-oxime-3,4'-piperidine]: M.p. 203° C.; $^1$H NMR (400 MHz, CDCl$_3$) 1.60 (m, 2H), 2.14 (m, 4H), 2.80 (s, 2H), 3.01 (d, J=10 Hz, 2H), 3.19 (d, J=6.4 Hz, 2H), 6.26 (dt, J=16 Hz, 6.4 Hz, 1H), 6.45 (d, J=16 Hz, 1H), 7.19-7.33 (m, 7H); 7.57 (d, J=7.6 Hz), 1H); MS (ES+) 367/369 (M+H$^+$). 1'-[trans-3-(4-chlorophenyl)allyl]spiro[indan-1-one-(Z)-oxime-3,4'-piperidine]: $^1$H NMR (400 MHz, CDCl$_3$) 1.60 (m, 2H), 2.20 (m, 4H), 2.70 (s, 2H), 3.03 (d, J=8.7 Hz, 2H), 3.22 (d, J=6.0 Hz, 2H), 6.26 (dt, J=16 Hz, 6.0 Hz, 1H), 6.45 (d, J=16 Hz, 1H), 7.15-7.34 (m, 7H); 8.32 (d, J=7.7 Hz), 1H); MS (ES+) 367/369 (M+H$^+$).

EXAMPLE 2

This Example illustrates the preparation of compound LXIX.1, 1'-[trans-3-(4-chlorophenyl)allyl]spiro[(indan-1-ylidene)hydrazine-3,4'-piperidine]

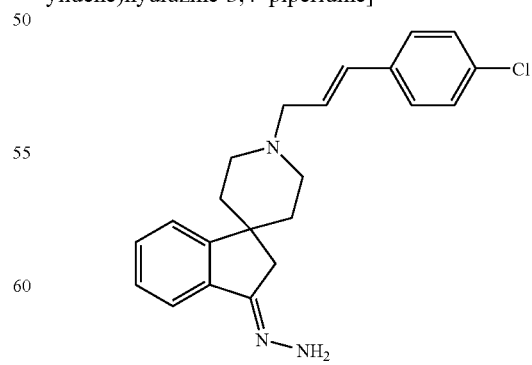

To a solution of 1'-[trans-3-(4-chlorophenyl)allyl]spiro[indan-1-one-3,4'-piperidine] (Example 1, step B) (2.49 g) in ethanol (75 ml) was added hydrazine monohydrate (0.4 ml)

and one drop of acetic acid. The reaction mixture was stirred at room temperature for 12 hours and concentrated in vacuo. The residue was dissolved in dichloromethane, washed with saturated aqueous sodium bicarbonate, dried (sodium sulphate) and concentrated in vacuo. The solid residue was recrystallised from ethyl acetate to give 2.2 g (88%) of a white solid. M.p. 140-142° C.; 1'-[trans-3-(4-chlorophenyl)allyl]spiro[(indan-1-(E)-ylidene)hydrazine-3,4'-piperidine]: $^1$H NMR (400 MHz, CDCl$_3$) 1.45 (m, 2H), 2.15 (m, 4H), 2.34 (s, 2H), 3.03 (d, J=10 Hz, 2H), 3.22 (d, J=6 Hz, 2H), 6.26 (dt, J=16 Hz, 6 Hz, 1H), 6.45 (d, J=16 Hz, 1H), 7.05-7.37 (m, 7H); 7.57 (d, J=7.2 Hz, 1H); MS (ES+) 366/368 (M+H$^+$).

EXAMPLE 3

This Example illustrates the preparation of compound III.3, 2-chloroisonicotinic acid [1'-[trans-3-(4-chlorophenyl)allyl]spiro[indan-1-ylidene-3,4'-piperidine]]hydrazide

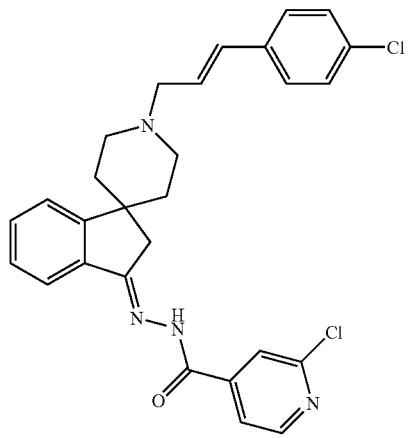 [SMILES: O=C(N/N=C1\CC2(CCN(C/C=C/c3ccc(Cl)cc3)CC2)c2ccccc21)c1ccnc(Cl)c1]

To a solution of 1'-[trans-3-(4-chlorophenyl)allyl]spiro[indan-1-one-3,4'-piperidine] (example 1, step B) (20 mg) in ethanol (3 ml) was added 2-chloro-isonicotinic acid hydrazide (15 mg) and one drop of sulphuric acid. The reaction mixture was refluxed for 12 hours and concentrated in vacuo. The residue was dissolved in dichloromethane, washed with saturated aqueous sodium bicarbonate, dried (sodium sulphate) and concentrated in vacuo. The solid residue was purified by preparative HPLC to give 22 mg of 2-chloroisonicotinic acid [1'-[trans-3-(4-chlorophenyl)allyl]spiro[indan-1-ylidene-3,4'-piperidine]]hydrazide; M.p. 240° C. $^1$H NMR (400 MHz, CDCl$_3$) 1.5 (m, 2H), 2.15 (m, 4H), 2.70 (s, 2H), 3.03 (m, 2H), 3.21 (m, 2H), 6.26 (dt, J=15.8 Hz, 5.8 Hz, 1H), 6.45 (d, J=15.8 Hz, 1H), 7.1-7.9 (m, 10H); 8.50 (d, J=4.7 Hz, 1H), 9.42 (br s, 1H); MS (ES+) 505/507 (M+H$^+$).

Compounds I.3, II.3, V.3, XII.3, LXVIII.14, LXVIII.15, LXIX.2, LXIX.3, LXIX.4, LXIX.13, LXIX.14, LXIX.16, LXIX.17, LXIX.18, LXIX.19, LXIX.20, LXIX.21 and LXIX.22 were prepared according to procedures analogous to those described in Example 3.

EXAMPLE 4

This Example illustrates the preparation of compound III.49, 2-chloroisonicotinic acid [5-chloro-1'-[trans-3-(4-chlorophenyl)allyl]spiro[indan-1-ylidene-3,4'-piperidine]]hydrazide

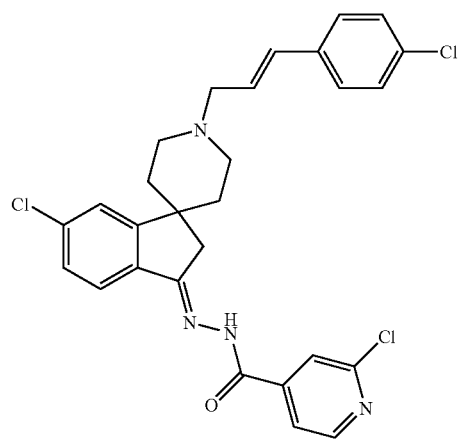 [SMILES: O=C(N/N=C1\CC2(CCN(C/C=C/c3ccc(Cl)cc3)CC2)c2cc(Cl)ccc21)c1ccnc(Cl)c1]

Step A:
To a solution of 5-chloroindene (4.2 g) in tetrahydrofuran (30 ml) at 0° C. was added dropwise lithium bis(trimethylsilyl)amide (1M in tetrahydrofuran, 70 ml) over 30 min. The resulting solution was stirred at 0° C. for 1 hour then transferred by cannula into a solution of bis-(2-chloro-ethyl)-carbamic acid tert-butyl ester (6.8 g) in tetrahydrofuran at 0° C. The resulting solution was stirred at 0° C. for 2 hours then at room temperature overnight. The solvent was evaporated in vacuo then the residue dissolved in dichloromethane, filtered over Hyflo, and concentrated in vacuo. Silica gel chromatography of the residue (eluent cyclohexane:ethyl acetate 8:2) afforded 7.3 g (82%) of a 1:1 regioisomeric mixture of 5-chloro-spiro[indene-3,4'-piperidine]-1'-carboxylic acid tert-butyl ester and 6-chloro-spiro[indene-3,4'-piperidine]-1'-carboxylic acid tert-butyl ester. $^1$H NMR (400 MHz, CDCl$_3$) 1.16 (m, 2H), 1.32 (s, 9H), 1.81 (m, 2H), 2.92 (m, 2H), 4.00 (m, 2H), 6.55 (6.56 for the isomer) (d, J=5.6 Hz, 1H), 6.67 (6.72 for the isomer) (d, J=5.6 Hz, 1H), 6.98-7.12 (m, 3H); MS (ES+) 220/222 (M-isobutene-CO$_2$+H$^+$).

Step B:
To a solution of the regioisomeric mixture obtained in Step A (7 g) in tetrahydrofuran (90 ml) at 70° C. under argon was added dropwise 9-borabicyclo[3.3.1]nonane (0.5M in tetrahydrofuran, 132 ml); the solution was heated at 70° C. for 30 min and concentrated in vacuo. The residue was dissolved in dichloromethane (440 ml), cooled to 0° C. and pyridinium chlorochromate (14.2 g) was added portionwise over 15 min. The resulting mixture was refluxed for 30 min, cooled to room temperature, diluted with ether (150 ml) and filtered on Hyflo. Concentration in vacuo followed by silica gel chromatography of the residue (eluent cyclohexane:ethyl acetate 9:1) afforded 0.43 g of 6-chloro-spiro[indan-1-one-3,4'-piperidine]-1'-carboxylic acid tert-butyl ester and 0.8 g of 5-chloro-spiro[indan-1-one-3,4'-piperidine]-1'-carboxylic acid tert-butyl ester. 5-chloro-spiro[indan-1-one-3,4'-piperidine]-1'-carboxylic acid tert-butyl ester: $^1$H NMR (400 MHz, CDCl$_3$) 1.39 (s, 9H), 1.70 (m, 2H), 1.92 (m, 2H), 2.65 (s, 2H), 2.87 (m, 2H), 4.26 (m, 2H), 7.39 (d, J=8.1 Hz, 1H), 7.45 (s, 1H), 7.71 (d, J=8.1 Hz); MS (ES+) 236 (M-isobutene-CO$_2$+H$^+$).

Step C: By analogy to the procedure described in Example 1, step A, 5-chloro-spiro[indan-1-one-3,4'-piperidine]-1'-carboxylic acid tert-butyl ester (1 g) was converted into 5-chloro-spiro[indan-1-one-3,4'-piperidine] (0.75 g).

Step D: By analogy to the procedure described in Example 1, step B, 5-chloro-spiro[indan-1-one-3,4'-piperidine] (118 mg)

was converted into 5-chloro-1'-[trans-3-(4-chlorophenyl)allyl]spiro[indan-1-one-3,4'-piperidine] (70 mg). MS (ES+) 386/388 (M+H+).
Step E: By analogy to the procedure described in Example 3,5-chloro-1'-[trans-3-(4-chlorophenyl)allyl]spiro[indan-1-one-3,4'-piperidine] (70 mg) was converted into the title compound (46 mg). M.p. 212° C.; MS (ES+) 540 (M+H+).
Compounds III.26, III.29, III.30, III.52, III.53, III.210, III.213, III.214, III.233, III.236 and III.237 were prepared according to procedures analogous to those described in Example 4.

EXAMPLE 5

This Example illustrates the preparation of compound III.1,2-chloroisonicotinic acid [1'-(4-chlorobenzyl)spiro[indan-1-ylidene-3,4'-piperidine]]hydrazide

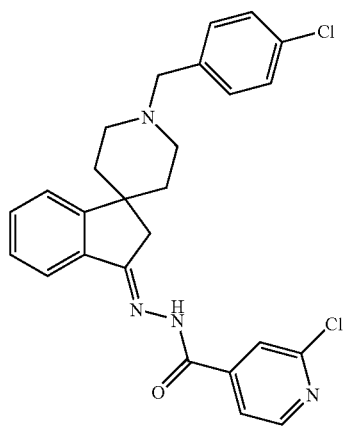 [SMILES: O=C(N/N=C1\CC2(CCN(Cc3ccc(Cl)cc3)CC2)c2ccccc21)c1ccnc(Cl)c1]

Step A: To a solution of spiro[indan-1-one-3,4'-piperidine]-1'-carboxylic acid tert-butyl ester (1.5 g) and 2-chloro-isonicotinic acid hydrazide (858 mg) in ethanol (50 ml) was added one drop of sulphuric acid, and the mixture was refluxed for 5 hours. The solvent was evaporated then the residue was dissolved in dichloromethane, the organic layer washed with saturated aqueous sodium bicarbonate, dried (sodium sulphate) and concentrated in vacuo. The residue was purified by silica gel chromatography (eluent ethyl acetate:cyclohexane 6:4) to give 1.6 g (70%) of the hydrazide LXVIII.2 as a yellowish solid; M.p. 90-95° C. MS (ES+) 455 (M+H+), 399 (M-isobutene+H+).
Step B:
Trifluoroacetic acid (7.3 ml) was added to a stirred solution of the hydrazide obtained in Step A (1.46 g) in anhydrous dichloromethane (30 ml). The reaction was stirred at room temperature for 1 h. The reaction was washed with saturated bicarbonate solution, dried over sodium sulphate and concentrated in vacuo to yield 1.1 g (98%) of 2-chloroisonicotinic acid [spiro(indan-1-ylidene-3,4'-piperidine)]hydrazide LXVHIII.1 as a yellow solid, which was used directly in the next step. M.p. 175-180° C. MS (ES+) 355 (M+H+).
Step C:
Diisopropylethylamine (0.07 ml) and 4-chlorobenzyl chloride-(32 mg) were added to a solution of 2-chloroisonicotinic acid [spiro(indan-1-ylidene-3,4'-piperidine)]hydrazide (71 mg) in acetonitrile (3 ml) under argon, and the mixture was refluxed for 1 hour. The reaction mixture was diluted with ethyl acetate and washed with saturated bicarbonate solution. The organic layer was dried (sodium sulphate), filtered and the solvents removed in vacuo. The crude product was purified by column chromatography [SiO2; ethyl acetate-triethylamine (100:0.1)] to give 33 mg (35%) of the title compound as a white solid; M.p. 198-200° C. 1H NMR (400 MHz, CDCl3) 1.43 (m, 2H), 2.08 (m, 4H), 2.68 (s, 2H), 2.86 (m, 2H), 3.46 (s, 2H), 7.04-7.91 (m, 10H), 8.48 (d, J=4.8 Hz, 1H), 9.44 (br s, 1H); MS (ES+) 352/354 (M+H+).
Compounds III.6, III.7, LXVIII.3, LXVIII, LXVIII.5, LXVIII.6, LXVIII.7, LXVIII.8, LXVIII.9, LXVIII.10, LXVIII.11, LXVIII.12 and LXVIII.13 were prepared according to procedures analogous to those described in Example 5.

EXAMPLE 6

This Example illustrates the preparation of compound LXIX.5

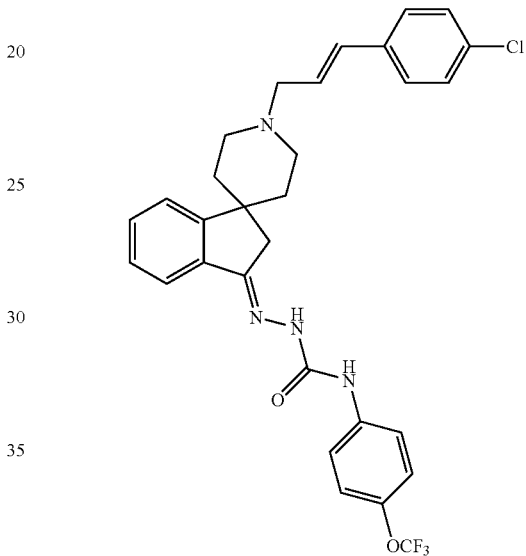

To a solution of 1'-[trans-3-(4-chlorophenyl)allyl]spiro[indan-1-ylidene-3,4'-piperidine]hydrazine (Example 2) (150 mg) in tetrahydrofuran (2 ml) was added 4-trifluoromethoxyphenyl isocyanate (38 mg) and the reaction mixture was stirred at room temperature for 20 min. The solution was concentrated in vacuo to give 136 mg of a solid which was washed with cold dichloromethane to afford 70 mg (50%) of the title compound as a white solid; M.p. 225° C. 1H NMR (400 MHz, CDCl3) 1.63 (m, 2H), 1.95 (m, 4H), 2.61 (s, 2H), 2.97 (m, 2H), 3.11 (d, J=6.4 Hz, 2H), 6.25 (dt, J=16 Hz, 6.0 Hz, 1H), 6.45 (d, J=16 Hz, 1H), 7.1-7.7 (m, 2H); 8.17 (s, 1H), 9.30 (s, 1H); MS (ES+) 569 (M+H+).
Compounds LXIX.6 to LXIX.12 inclusive, LXIX.15 and LXIX.23 were prepared according to procedures analogous to those described in Example 6.

EXAMPLE 7

This Example illustrates the pesticidal/insecticidal properties of compounds of formula (I). Test against were performed as follows:
*Spodoptera littoralis* (Egyptian Cotton Leafworm)
Cotton leaf discs were placed on agar in a 24-well microtiter plate and sprayed with test solutions at an application rate of 200 ppm. After drying, the leaf discs were infested with 5 L1 larvae. The samples were checked for mortality, repellent effect, feeding behaviour, and growth regulation 3 days after treatment (DAT). The following compounds gave at least 80% control of *Spodoptera littoralis:*
II.3, III.1, III.3, III.7, III.26, III.29, III.30, III.49, III.52, III.53, III.214, III.233, III.236, III.237, V.3, XVII.3, LXVIII.3, LXVIII.4, LXVIII.8, LXVIII.9, LXVIII.11, LXVIII.12, LXIX.1, LXIX.13, LXIX.16, LXIX.20, LXIX.21, LXIX.22.

*Heliothis virescens* (Tobacco Budworm):
Eggs (0-24 h old) were placed in 24-well microtiter plate on artificial diet and treated with test solutions at an application rate of 200 ppm by pipetting. After an incubation period of 4 days, samples were checked for egg mortality, larval mortality, and growth regulation. The following compounds gave at least 80% control of *Heliothis virescen:*
II.3, III.1, III.3, III.6, III.7, III.26, III.29, III.30, III.49, III.52, III.53, III.210, III.213, III.214, III233, III.236, III.237, V.3, XII.3, LXVIII.4, LXVIII.6, LXVIII.7, LXVIII.8, LXVIII.9, LXVI11.1, LXVI11.12, LXIX.2, LXIX.3, LXIX.13, LXIX.16, LXIX.19, LXIX.20, LXIX.21, LXIX.22.

*Plutella xylostella* (Diamond Back Moth):
24-well microtiter plate (MTP) with artificial diet was treated with test solutions at an application rate of 18.2 ppm by pipetting. After drying, the MTP's were infested with larvae (L2)(10-15 per well). After an incubation period of 5 days, samples were checked for larval mortality, antifeedant and growth regulation. The following compounds gave at least 80% control of *Plutella xylostella:*
II.3, III.3, III.6, III.7, III.26, III.29, III.30, III.49, III.52, III.53, III.210, III.213, III.214, III233, III.236, III.237, V.3, XII.3, LXV III.8, LXIX.1, LXIX.2, LXIX.3, LXIX.12, LXIX.13, LXIX.16, LXIX.19, LXIX.20, LXIX1.21, LXIX.22, LXX.1.

*Tetranychus urticae* (Two-Spotted Spider Mite):
Bean leaf discs on agar in 24-well microtiter plates were sprayed with test solutions at an application rate of 200 ppm: After drying, the leaf discs are infested with mite populations of mixed ages. 8 days later, discs are checked for egg mortality, larval mortality, and adult mortality. The following compounds gave at least 80% control of *Tetranychus urticae:* III.26, LXIX.21.

*Aedes aegypti* (Yellow Fever Mosquito):
10-15 *Aedes* larvae (L2) together with a nutrition mixture are placed in 96-well microtiter plates. Test solutions at an application rate of 2 ppm are pipetted into the wells. 2 days later, insects were checked for mortality and growth inhibition. The following compounds gave at least 80% control of *Aedes aegypti*
II.3, III.3, III.7, III.26, III.29, III.30, III.49, III.52, III.53, III.213, III.214, III233, III.236, V.3, LXVIII.12, LXIX.21, LXIX.22.

The invention claimed is:
1. A compound of formula I:

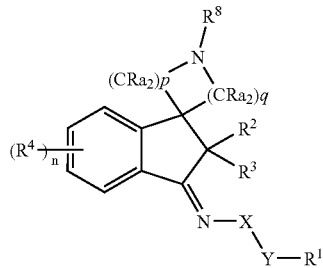

(I)

wherein
X is $NR^{11}$;
$R^{11}$ is hydrogen or $C_{1-6}$ alkyl;
Y is C=O;
$R^1$ is hydrogen,
$C_{1-6}$ alkyl,
$C_{1-6}$ haloalkyl,
heteroaryl($C_{1-3}$)alkyl wherein the heteroaryl group may be optionally substituted by halogen, cyano, $C_{1-6}$ alkyl, or $C_{1-6}$ haloalkyl and where the heteroaryl group is a thiazole, pyridine, pyrimidine, pyrazine or pyridazine ring,
heteroaryl optionally substituted by halogen, cyano, $C_{1-6}$ alkyl, or $C_{1-6}$ haloalkyl and where the heteroaryl group is a pyridine, pyrimidine, 2,1,3-benzoxadiazole, pyrazine or pyridazine ring,
$C_{1-6}$ alkoxy,
$C_{1-6}$ alkylamino, or
heteroaryl($C_{1-3}$)alkylamino wherein the heteroaryl group may be optionally substituted by halogen, cyano, $C_{1-6}$ alkyl, or $C_{1-6}$ haloalkyl and where the heteroaryl group is a thiazole, pyridine, pyrimidine, pyrazine or pyridazine ring;
$R^2$ and $R^3$ are both hydrogen;
each $R^4$ is independently fluoro, chloro, bromo, cyano, cyano, $C_{1-4}$ alkyl, $C_{1-4}$ haloalkyl, $C_{1-4}$ cyanoalkyl or $C_{1-3}$ alkoxy ($C_{1-3}$) alkyl;
n is 0, 1 or 2;
each Ra is hydrogen;
p and q are both 2;
$R^8$ is phenyl($C_{1-4}$)alkyl wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino,
heteroaryl($C_{1-6}$)alkyl wherein the heteroaryl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino,
phenyl($C_{2-6}$)alkenyl wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino,
heteroaryl($C_{2-6}$)alkenyl wherein the heteroaryl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino, or
—C($R^{51}$)($R^{52}$)—[$CR^{53}$=$CR^{54}$]z-$R^{55}$;
z is 1 or 2;
$R^{51}$ and $R^{52}$ are each independently H, halogen or $C_{1-2}$ alkyl;
$R^{53}$ and $R^{54}$ are each independently H, halogen, $C_{1-4}$ alkyl or $C_{1-4}$ haloalkyl; and
$R^{55}$ is optionally substituted aryl or optionally substituted heteroaryl;
wherein the heteroaryl group of $R^8$ is selected from a pyridine, pyrimidine, triazine, thienyl, furyl, oxazoline, isoxazole, 2,1,3-benzoxadiazole or thiazole ring; or salts thereof.

2. A compound according to claim 1 wherein X is NH.

3. A compound of formula III

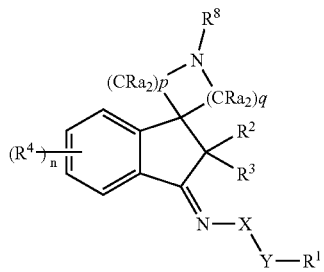

(III)

wherein X is $NR^{11}$, Y, $R^1$, $R^2$, $R^3$, Ra, n, p, q and $R^{11}$ are as defined in claim 1 and $R^8$ is hydrogen or tert-butoxycarbonyl.

4. An insecticidal acaricidal and nematicidal composition comprising an insecticidally, acaricidally or nematicidally effective amount of a compound of claim 1.

5. A method of combating and controlling insects, acarines, nematodes or molluscs which comprises applying to a pest, to a locus of a pest, or to a plant susceptible to attack by a pest an insecticidally, acaricidally, nematicidally or molluscicidally effective amount of a compound of claim 1.

6. A compound according to claim 1 wherein n is 0.

7. A compound according to claim 6 wherein $R^1$ is heteroaryl optionally substituted by halogen, cyano, $C_{1-6}$ alkyl, or $C_{1-6}$ haloalkyl and where the heteroaryl group is a pyridine, pyrimidine, 2,1,3-benzoxadiazole, pyrazine or pyridazine ring.

8. A compound according to claim 7 wherein $R^8$ is $-C(R^{51})(R^{52})-[CR^{53}=CR^{54}]z-R^{55}$.

9. A compound according to claim 8 wherein z is 1; $R^{51}$ and $R^{52}$ are each independently H; $R^{53}$ and $R^{54}$ are each independently H; and $R^{55}$ is optionally substituted aryl.

10. A compound according to claim 9 having a formula:

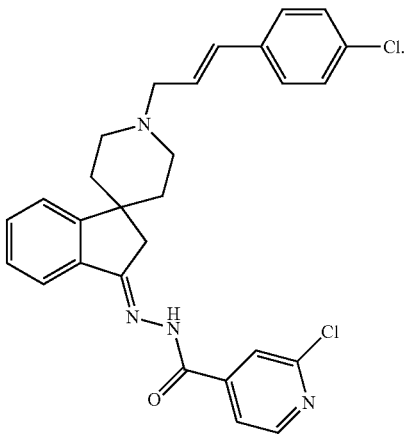 [SMILES: O=C(N/N=C1\CC2(CCN(C/C=C/c3ccc(Cl)cc3)CC2)c2ccccc21)c1ccnc(Cl)c1]

11. An insecticidal acaricidal and nematicidal composition comprising an insecticidally, acaricidally or nematicidally effective amount of a compound of claim 10.

12. An insecticidal acaricidal and nematicidal composition comprising an insecticidally, acaricidally or nematicidally effective amount of a compound of claim 7.

13. A compound according to claim 1 wherein $R^1$ is pyridyl optionally substituted by halogen, $C_{1-3}$ alkyl or $C_{1-3}$ haloalkyl.

14. A compound according to claim 2 wherein $R^1$ is pyridyl optionally substituted by halogen, $C_{1-3}$ alkyl or $C_{1-3}$ haloalkyl.

15. A compound according to claim 1 wherein each $R^4$ is independently fluoro, chloro, bromo, $C_{1-4}$ alkyl or $C_{1-4}$ haloalkyl; and n is 1 or 2.

16. A compound according to claim 1 wherein $R^8$ is $-C(R^{51})(R^{52})-[CR^{53}=CR^{54}]z-R^{55}$, and $R^{55}$ is phenyl substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino; or $R^{55}$ is heteroaryl substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino.

17. A compound according to claim 16 wherein z is 1, $R^{51}$ and $R^{52}$ are both hydrogen, $R^{53}$ and $R^{54}$ are both hydrogen, and $R^{55}$ is phenyl substituted with one to three substituents selected from halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino.

* * * * *